(12) United States Patent
Park et al.

(10) Patent No.: US 7,576,222 B2
(45) Date of Patent: Aug. 18, 2009

(54) ALKYNYL-CONTAINING TRYPTOPHAN DERIVATIVE INHIBITORS OF TACE/MATRIX METALLOPROTEINASE

(75) Inventors: Kaapjoo Park, Congers, NY (US); Jeremy I. Levin, New City, NY (US); Ariamala Gopalsamy, Mahwah, NJ (US)

(73) Assignee: Wyeth, Madison, NJ (US)

( * ) Notice: Subject to any disclaimer, the term of this patent is extended or adjusted under 35 U.S.C. 154(b) by 234 days.

(21) Appl. No.: 11/318,701

(22) Filed: Dec. 27, 2005

(65) Prior Publication Data

US 2006/0160884 A1 Jul. 20, 2006

Related U.S. Application Data

(60) Provisional application No. 60/639,452, filed on Dec. 28, 2004.

(51) Int. Cl.
C07D 209/14 (2006.01)
(52) U.S. Cl. ...................................... 548/496
(58) Field of Classification Search .................. 548/496
See application file for complete search history.

(56) References Cited

U.S. PATENT DOCUMENTS

| | | | |
|---|---|---|---|
| 5,756,546 A | 5/1998 | Pirotte | |
| 5,962,529 A | 10/1999 | Miller | |
| 6,022,898 A | 2/2000 | Miller | |
| 6,124,332 A | 9/2000 | Miller | |
| 6,124,333 A | 9/2000 | Miller | |
| 6,150,394 A | 11/2000 | Wantanabe | |
| 6,197,770 B1 | 3/2001 | Natchus | |
| 6,225,311 B1 | 5/2001 | Levin | |
| 6,235,768 B1 | 5/2001 | Wantanabe | |
| 6,277,987 B1 | 8/2001 | Kukkola | |
| 6,326,516 B1 | 12/2001 | Levin | |
| 6,340,691 B1 | 1/2002 | Levin | |
| 6,358,980 B1 | 3/2002 | Levin | |
| 6,423,729 B1 * | 7/2002 | Kurihara et al. ............. 514/364 |
| 6,441,021 B1 | 8/2002 | Wantanabe | |

FOREIGN PATENT DOCUMENTS

| | | |
|---|---|---|
| EP | 0757037 | 2/1997 |
| EP | 0877018 | 11/1998 |
| EP | 0877019 | 11/1998 |
| EP | 0878467 | 11/1998 |
| EP | 0967201 | 12/1999 |
| EP | 1233016 | 8/2002 |
| FR | 2508444 | 12/1982 |
| JP | 11246527 | 9/1999 |
| JP | 11343279 | 12/1999 |
| WO | WO 92/04320 | 3/1992 |
| WO | WO 97/27174 | 7/1997 |
| WO | WO 99/04780 | 2/1999 |
| WO | WO 99/51572 | 10/1999 |
| WO | WO 00/15213 | 3/2000 |
| WO | WO 00/27808 | 5/2000 |
| WO | WO 00/58280 | 5/2000 |
| WO | WO 00/44709 | 8/2000 |
| WO | WO 00/44723 | 8/2000 |
| WO | WO 00/51975 | 9/2000 |
| WO | WO 00/58304 | 10/2000 |
| WO | WO 01/10827 | 2/2001 |
| WO | WO 01/27084 | 4/2001 |
| WO | WO 01/55133 | 8/2001 |
| WO | WO 01/70682 | 9/2001 |
| WO | WO 01/70690 | 9/2001 |
| WO | WO 01/70691 | 9/2001 |
| WO | WO 01/70693 | 9/2001 |
| WO | WO 01/70720 | 9/2001 |
| WO | WP 01/83463 | 11/2001 |
| WO | WO 02/067866 | 9/2002 |
| WO | WO 02/088115 | 11/2002 |
| WO | WO 03/035610 | 5/2003 |
| WO | WO 03/091250 | 11/2003 |

OTHER PUBLICATIONS

Metastasis [onlone] {retrieved on Apr. 12, 2008 from the Internet} {URL: http://www.healthline.com/adamcontent/metastasis?utm+medium=ask&utm_source=smart.*
Diabetes Mellitus [online], [retrieved on Apr. 17, 2007]. Retrieved from the Internet, URL: http://www.merck.com/mmpe/print/sec/2/ch 158/ch 158b.html>.*
Cancer and Metastasis Reviews (1998), 17(1 ), 91-106.*
Science (1999), vol. 286, 531-537.*
Cancer [online], [retrieved on Jul. 6, 2007]. Retrieved from the Internet, URL: http://www.nlm.nih.gov/medlineplus/cancer.html>.*

(Continued)

*Primary Examiner*—Rebecca L Anderson
*Assistant Examiner*—Shawquia Young
(74) *Attorney, Agent, or Firm*—Pepper Hamilton LLP

(57) ABSTRACT

This invention provides compounds of Formula I, having the structure:

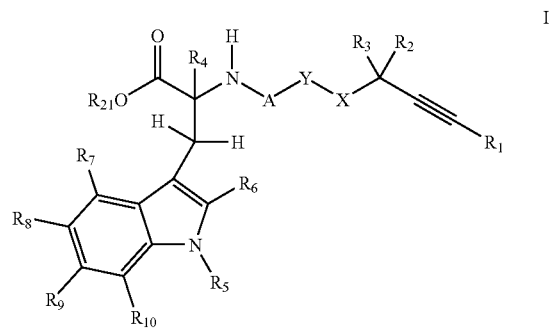

that are useful in treating diseases or disorders mediated by TNF-α. The invention further provides methods for use of the compounds for treating such a disease or disorder or for alleviating symptoms thereof.

25 Claims, No Drawings

OTHER PUBLICATIONS

Cancer [online], [retrieved on Jul. 6, 2007]. Retrieved from the Internet, URL: http://en.wikipedia.org/wiki/Cancer>.*

Beutler et al., "Tumour necrosis, cachexia, shock, and inflammation: a common mediator," *Ann Rev Biochem* (1988) 57:505-518.

Camussi et al., "The Future Role of Anti-Tumour Necrosis Factor (TNF) Products in the Treatment of Rheumatoid Arthritis," *Drugs* (1998) 55(5):613-620.

Ferrari et al., "Tumor necrosis factor soluble receptors in patients with various degrees of congestive heart failure," *Circulation* (1995) 92(6):1479.

Gilchrist et al., "Addition and cycloaddition reactions of the electrophilic vinyl nitroso compounds 3-nitrosobut-3-en-2-one, 2-nitrosopropenal, and ethyl 2-nitrosopropenoate," *J Chem Soc Perkin, Trans 1* (1983) 1283-1292.

Grossman et al., "Rheumatoid arthritis: current clinical and research directions," *J. Women's Health* (1997) 6(6):627.

Hotamisligil et al., "Adipose expression of tumor necrosis factor-alpha: direct role in obesity-linked insulin resistance," *Science* (1993) 259:87.

Isomaki et al., "Pro- and anti-inflammatory cytokines in rheumatoid arthritis," *Ann Med* (1997) 29:499.

Jin et al., "Crystal structure of the catalytic domain of a human thioredoxin-like protein," *Analytical Biochemistry* (2002) 302:269-275.

Knight et al., "A novel coumarin-labelled peptide for sensitive continuous assays of the matrix metalloproteinases," *FEBS Lett* (1992) 296:263-266.

Ksontini et al., "Revisiting the role of tumor necrosis factor alpha and the response to surgical injury and inflammation," *Arch Surg* (1998) 133:558.

Li et al., "The genetic study of retinoblastoma," *Synthesis* (1988) 73-76.

Mathison et al., "Participation of tumor necrosis factor in the mediation of gram negative bacterial lipopolysaccharide-induced injury in rabbits," *J Clin Invest* (1988) 81:1925.

McGeehan et al., "TNF-alpha in human diseases," *Current Pharmaceutical Design* (1996) 2(6):662-667.

Miethke et al., "T cell-mediated lethal shock triggered in mice by the superantigen staphylococcal enterotoxin B: critical role of tumor necrosis factor," *J Exp Med* (1992) 175:91.

Newton et al., "Biology of TACE inhibition," *Ann Rheum Dis* (2001) 60:iii25-iii32.

Old "Tumor necrosis factor (TNF)," *Science* (1985) 230:630.

Pallares-Trujillo et al., "TNF and AIDS: two sides of the same coin?," *Med Res Reviews* (1995) 15(6):533-546.

Packer "Is tumor necrosis factor an important neurohormonal mechanism in chronic heart failure?," *Circulation* (1995) 92(6):1379.

Peterson et al., "Human cytomegalovirus-stimulated peripheral blood mononuclear cells induce HIV-1 replication via a tumor necrosis factor-alpha-mediated mechanism," *J Clin Invest* (1992) 89:574.

Piguet et al., "Tumor necrosis factor/cachectin is an effector of skin and gut lesions of the acute phase of graft-vs.-host disease," *J Exp Med* (1987) 166:1280.

Rankin et al., "The therapeutic effects of an engineered human anti-tumour necrosis factor alpha antibody (CDP571) in rheumatoid arthritis," *Br J Rheumatol* (1995) 34:334.

Shire et al., "TNF-α inhibitors and rheumatoid arthritis," *Exp Opin Ther. Patents* (1998) 8(5):531-544.

Zhang et al., "Identification and characterization of 4-[[4-(2-butynyloxy)phenyl]sulfonyl]-N-hydroxy-2,2-dimethyl-(3S)thiomorpholinecarboxamide (TMI-1), a novel dual tumor necrosis factor-alpha-converting enzyme/matrix metalloprotease inhibitor for the treatment of rheumatoid arthritis," *Journal of Pharmacology and Experimental Therapeutics* (2004) 309:348-355.

*Pharmaprojects* (1996), Therapeutic Updates 17(Oct.), au197-au198.

*Scrip* (1998) 2349:2.

Brynskov, J. et al., "Tumor necrosis factor alpha converting enzyme (TACE) activity in the colonic mucosa of patients with inflammatory bowel disease", Gut, 2002, 51: 37-43.

Rutgeerts, P. and Baert, F., "Novel therapies for Crohn's disease", Drugs of Today, 2000, 36 (Suppl. G), 59-68.

Lovell, D.J. et al., "Long-Term Efficacy and Safety of Etanercept in Children With Polyarticular-Course Juvenile Rheumatoid Arthritis", Arthritis & Rheumatism, 2003, 48(1): 218-226.

Calamia, K.T., "Current and future use of anti-TNF agents in the treatment of autoimmune, inflammatory disorders", Advances in Experimental Medicine and Biology, 2003, 528 (Adamantiades-Behcet's Disease), 545-549.

* cited by examiner

ALKYNYL-CONTAINING TRYPTOPHAN DERIVATIVE INHIBITORS OF TACE/MATRIX METALLOPROTEINASE

CROSS REFERENCE TO RELATED APPLICATIONS

This application claims priority to U.S. Provisional Application Ser. No. 60/639,452 filed on Dec. 28, 2004, which is incorporated herein by reference in its entirety.

FIELD OF THE INVENTION

This invention relates to acetylenic aryl carboxylic acid inhibitors of TNF-α converting enzyme (TACE)/matrix metalloproteinase (MMP). The compounds of the present invention are useful in disease conditions mediated by TNF-α, such as rheumatoid arthritis (RA), juvenile RA, psoriatic arthritis, ankylosing spondylitis, psoriasis, osteoarthritis, tumor metastasis, sepsis, AIDS, ulcerative colitis, multiple sclerosis, diabetes (insulin resistance), Crohn's disease, degenerative cartilage loss, asthma, idiopathic pulmonary fibrosis, vasculitis, systemic lupus erythematosus, irritable bowel syndrome, acute coronary syndrome, hepatitis C, cachexia, COPD (chronic obstructive pulmonary disease), and type 2 diabetes.

BACKGROUND OF THE INVENTION

TNF-α converting enzyme (TACE) catalyzes the formation of TNF-α from membrane bound TNF-α precursor protein. TNF-α is a pro-inflammatory cytokine that is believed to have a role in rheumatoid arthritis [Shire, M. G.; Muller, G. W. *Exp. Opin. Ther. Patents* 1998, 8(5): 531; Grossman, J. M.; Brahn, E. *J. Women's Health* 1997, 6(6): 627; Isomaki, P.; Punnonen, J. *Ann. Med.* 1997, 29: 499; Camussi, G.; Lupia, E. *Drugs,* 1998, 55(5): 3] septic shock [Mathison et al. *J. Clin. Invest.* 1988, 81: 1925; Miethke et al. *J. Exp. Med.* 1992, 175: 91], graft rejection [Piguet, P. F. et al. *J. Exp. Med.* 1987, 166: 1280], cachexia [Beutler, B.; Cerami, A. *Ann. Rev. Biochem.* 1988, 57: 505], anorexia, inflammation [Ksontini, R. et al. *Arch. Surg.* 1998, 133: 558], congestive heart failure [Packer, M. *Circulation,* 1995, 92(6): 1379; Ferrari, R. et al. *Circulation,* 1995, 92(6): 1479], post-ischaemic reperfusion injury, inflammatory disease of the central nervous system, inflammatory bowel disease, insulin resistance [Hotamisligil, G. S. et al. *Science,* 1993, 259: 87] and HIV infection [Peterson, P. K. et al. *J. Clin. Invest.* 1992, 89: 574; Pallares-Trujillo, J. et al. *Med. Res. Reviews,* 1995, 15(6): 533], in addition to its well-documented antitumor properties [Old, L. *Science,* 1985, 230: 630]. For example, research with anti-TNF-α antibodies and transgenic animals has demonstrated that blocking the formation of TNF-α inhibits the progression of arthritis [Rankin, E. C. et al. *Br. J. Rheumatol.* 1995, 34: 334; *Pharmaprojects,* 1996, Therapeutic Updates 17(Oct.), au197-M2Z]. This observation has recently been extended to humans as well ["TNF-α in Human Diseases", *Current Pharmaceutical Design,* 1996, 2: 662].

Because of the link between TNF-α and various disease states, it is expected that small molecule inhibitors of TACE/MMP would have the potential for treating such diseases. However, although a variety of TACE inhibitors are known, many of these molecules are peptidic and peptide-like, which suffer from bioavailability and pharmacokinetic problems. In addition, many of these molecules are non-selective, being potent inhibitors of matrix metalloproteinases and, in particular, MMP-1. Inhibition of MMP-1 (collagenase 1) has been postulated to cause joint pain in clinical trials of MMP inhibitors [*Scrip,* 1998, 2349: 20]. Long acting, selective, orally bioavailable non-peptide inhibitors of TACE would thus be highly desirable for the treatment of the disease states discussed above. The present invention is directed to these, as well as other, important ends

SUMMARY OF THE INVENTION

In some embodiments, the present invention provides compounds having the Formula I:

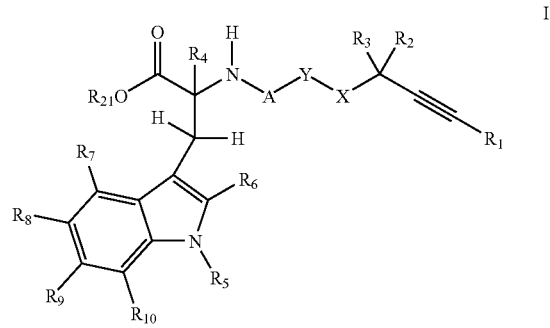

wherein:

$R_1$ is H, aryl, heteroaryl, $C_{1-8}$ alkyl, $C_{2-8}$ alkenyl, $C_{2-8}$ alkynyl, $C_{3-8}$ cycloalkyl, aralkyl, heteroalkyl, halogen, hydroxyalkyl, alkoxy, alkenyloxy, alkynyloxy, perfluoroalkoxy, alkoxy-alkyl, or $C_{4-8}$-cycloheteroalkyl having from 1-2 heteroatoms selected from N, $NR_5$, S and O;

wherein each of said aryl, heteroaryl, $C_{1-8}$ alkyl, $C_{2-8}$ alkenyl, $C_{2-8}$ alkynyl, $C_{3-8}$ cycloalkyl or aralkyl can be optionally substituted with up to four independently selected $R_{14}$ groups;

$R_2$, $R_3$ and $R_4$ are each independently, H, $C_{1-8}$ alkyl, halogen, CN, CCH, OH, or $OR_1$;

$R_5$, $R_6$, $R_7$, $R_8$, $R_9$ and $R_{10}$ are each independently, H, aryl, heteroaryl, $C_{1-8}$ alkyl, $C_{2-8}$ alkenyl, $C_{2-8}$ alkynyl, $C_{3-8}$ cycloalkyl, aralkyl, heteroalkyl, heteroarylalkyl, halogen, CN, hydroxyalkyl, alkoxy, alkenyloxy, alkynyloxy, perfluoroalkoxy, alkoxy-alkyl, $NR_{11}R_{11}$, $COOR_{11}$, $OR_{11}$, or $C_{4-8}$ cycloheteroalkyl having from 1-2 heteroatoms selected from N, $NR_{11}$, S and O;

wherein each of said aryl, heteroaryl, heteroalkyl, heteroarylalkyl, $C_{4-8}$ cycloheteroalkyl, $C_{1-8}$ alkyl, $C_{2-8}$ alkenyl, $C_{2-8}$ alkynyl, $C_{3-8}$ cycloalkyl, or aralkyl can be optionally substituted with up to four independently selected $R_{15}$ groups;

wherein one or more than one of the pairs $R_4$ and $R_6$, $R_4$ and $R_7$, $R_5$ and $R_6$, $R_5$ and $R_{10}$, $R_7$ and $R_8$, $R_8$ and $R_9$ or $R_9$ and $R_{10}$, together with the carbon atom or atoms to which they are attached, can form a cycloalkyl ring having 3-8 carbon atoms, or a $C_{4-8}$ cycloheteroalkyl ring;

$R_{11}$ is H, aryl, heteroaryl, aralkyl, $C_{1-8}$ alkyl, $C_{3-8}$ cycloalkyl, oxy, halogen, hydroxyalkyl, alkoxy, alkoxy-alkyl, alkenyloxy, alkynyloxy, perfluoroalkoxy, alkoxy-alkyl, $C_{1-8}$ alkanoyl, $COOR_1$, $COR_1$, $SO_2$—$C_{1-8}$ alkyl, $SO_2$-aryl, $SO_2$-heteroaryl, or CO—$NHR_1$;

wherein each of said aryl, heteroaryl, aralkyl, $C_{1-8}$ alkyl, $C_{3-8}$ cycloalkyl, $SO_2$—$C_{1-8}$ alkyl, $SO_2$-aryl and $SO_2$-heteroaryl can be optionally substituted with up to four independently selected $R_{16}$ groups;

each $R_{14}$, $R_{15}$ and $R_{16}$ is, independently, halogen, $C_{1-6}$ alkyl, $C_{2-8}$ alkenyl, $C_{2-8}$ alkynyl, $C_{3-8}$ cycloalkyl, —$OR_{17}$, CN, $COR_{12}$, $C_{1-6}$ haloalkyl, $C_{1-6}$ perhaloalkyl, $C_{1-6}$ haloalkoxy, $C_{1-6}$ perhaloalkoxy, $C_{1-6}$ perfluoroalkyl, —O—$C_{1-6}$ perfluoroalkyl, $CONR_{12}R_{13}$, —$OPO(OR_{12a})OR_{13a}$, —$PO(OR_{12a})R_{13}$, —$OC(O)OR_{12a}$, —O—$C_{1-6}$alkyl-$NR_{12}R_{13}$, —$OC(O)NR_{12}R_{13}$, —$C(O)NR_{12}OR_{13a}$, —$COOR_{12a}$, —$SO_3H$, —$NR_{12}R_{13}$, —$N(R_{20})(C_{1-6}$ alkyl)$NR_{12}$, —$N(R_{20})COR_{13}$, —$N(R_{20})COOR_{13a}$, —$SO_2NR_{12}R_{13}$, $NO_2$, —$N(R_{20})SO_2R_{13}$, —$N(R_{20})CONR_{12}R_{13}$, —$N(R_{20})C(=NR_{13})NR_{12}R_{13}$, —$N(R_{20})C(=NR_{13})N(SO_2R_{12})R_{13}$, —$N(R_{20})C(=NR_{13})N(C=OR_{12})R_{13}$, -tetrazol-5-yl, —$SO_2NHCN$, —$SO_2NHCONR_{12}R_{13}$, aryl, phenyl, heteroaryl, —$C_{5-8}$ cycloheteroalkyl, $CH_2$—$OR_{22}$, —$SR_{22}$, —$CH_2$—$SR_{22}$, —$SO_2NR_{12}R_{13}$, —$C(=NR_{22})$—, —$C(NCN)R_{22}$—, —$CSN(R_{22})_2$, —$C(NH)N(R_{22})_2$, $NO_2$, $NO_3$, azido, hydrazino, hydroxylamino, disulfide, urea, guanidine or —$S(O)_nR_{12}$ wherein n is 0, 1 or 2;

or any two $R_{14}$, $R_{15}$ or $R_{16}$ groups when attached to an aryl, aralkyl, heteroaryl or heteroarylalkyl group can together form a group of formula —O—$(CH_2)_k$—O— wherein k is 1 or 2;

each $R_{12}$ and $R_{13}$ is, independently, H, OH, $C_{1-8}$ alkyl, $C_{3-8}$ cycloalkyl, aryl, heteroaryl, alkoxy, alkenyloxy, alkynyloxy, perfluoroalkoxy, alkoxy-alkyl, aralkyl, or $C_{4-8}$ cycloheteroalkyl; or —$NR_{12}R_{13}$ may form a pyrrolidine, piperidine, morpholine, thiomorphohne, oxazolidine, thiazolidine, pyrazolidine, piperazine, or azetidine ring;

each $R_{12a}$ and $R_{13a}$ is, independently, H, $C_{1-8}$ alkyl, $C_{2-8}$ alkenyl, $C_{2-8}$ alkynyl, $C_{1-3}$ perfluoroalkyl, $C_{3-8}$ cycloalkyl, aryl, heteroaryl, alkoxy-alkyl, aralkyl, or $C_{4-8}$ cycloheteroalkyl;

each $R_{20}$ is, independently, H or $C_{1-6}$ alkyl;

each $R_{17}$ is, independently, H, $C_{1-8}$ alkyl, $C_{2-8}$ alkenyl, $C_{2-8}$ alkynyl, $C_{3-8}$ cycloalkyl, aryl, heteroaryl, alkoxy-alkyl, aralkyl or $C_{4-8}$ cycloheteroalkyl;

$R_{21}$ is H or $C_{1-8}$ alkyl;

each $R_{22}$ is, independently, H or $C_{1-3}$ alkyl;

A is $SO_2$ or —P(O)—$R_{10}$;

X is O, NH, $CH_2$ or S; and

Y is aryl or heteroaryl;

with the proviso that A and X are not bonded to adjacent atoms of Y;

or a pharmaceutically acceptable salt or prodrug thereof.

In some embodiments, compounds are provided having the Formula II:

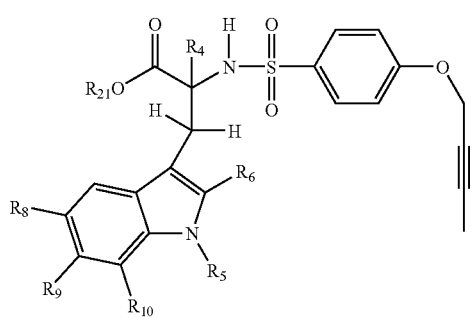

wherein the constituent variables are as described above, or a pharmaceutically acceptable salt or prodrug thereof.

The compounds of the present invention are useful for the treatment of disease conditions mediated by TNF-α, such as rheumatoid arthritis (RA), juvenile RA, psoriatic arthritis, ankylosing spondylitis, psoriasis, osteoarthritis, tumor metastasis, sepsis, AIDS, ulcerative colitis, multiple sclerosis, diabetes (insulin resistance), Crohn's disease, degenerative cartilage loss, asthma, idiopathic pulmonary fibrosis, vasculitis, systemic lupus erythematosus, irritable bowel syndrome, acute coronary syndrome, hepatitis C, cachexia, COPD, and type 2 diabetes and for the alleviation of symptoms thereof.

The present invention further provides methods of using the compounds described herein. In some embodiments, the methods include identifying a mammal having a disease or disorder mediated by TNF-α, and providing to the mammal an effective amount of a compound as described herein.

In further embodiments, the methods include identifying a mammal having a symptom of a disease or disorder mediated by TNF-α, and providing to the mammal an amount of a compound as described herein effective to ameliorate the symptom.

DESCRIPTION OF THE INVENTION

In one aspect, the present invention is directed to compounds that are inhibitors of TNF-α converting enzyme (TACE) and matrix metalloproteinases (MMPs). In some embodiments, the compounds have the Formula I:

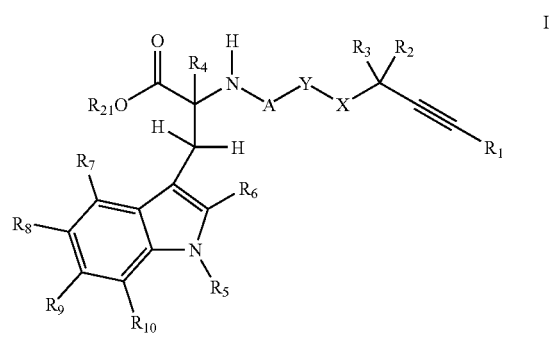

wherein:

$R_1$ is H, aryl, heteroaryl, $C_{1-8}$ alkyl, $C_{2-8}$ alkenyl, $C_{2-8}$ alkynyl, $C_{3-8}$ cycloalkyl, aralkyl, heteroalkyl, halogen, hydroxyalkyl, alkoxy, alkenyloxy, alkynyloxy, perfluoroalkoxy, alkoxy-alkyl, or $C_{4-8}$-cycloheteroalkyl having from 1-2 heteroatoms selected from N, $NR_5$, S and O; wherein each of said aryl, heteroaryl, $C_{1-8}$ alkyl, $C_{2-8}$ alkenyl, $C_{2-8}$ alkynyl, $C_{3-8}$ cycloalkyl or aralkyl can be optionally substituted with up to four independently selected $R_{14}$ groups;

$R_2$, $R_3$ and $R_4$ are each, independently, H, $C_{1-8}$ alkyl, halogen, CN, CCH, OH, or $OR_1$;

$R_5$, $R_6$, $R_7$, $R_8$, $R_9$ and $R_{10}$ are each, independently, H, aryl, heteroaryl, $C_{1-8}$ alkyl, $C_{2-8}$ alkenyl, $C_{2-8}$ alkynyl, $C_{1-8}$ cycloalkyl, aralkyl, heteroalkyl, heteroarylalkyl, halogen, CN, hydroxyalkyl, alkoxy, alkenyloxy, alkynyloxy, perfluoroalkoxy, alkoxy-alkyl, $NR_{11}R_{11}$, $COOR_{11}$, $OR_{11}$, or $C_{4-8}$ cycloheteroalkyl having from 1-2 heteroatoms selected from N, $NR_{11}$, S and O;

wherein each of said aryl, heteroaryl, heteroalkyl, heteroarylalkyl, $C_{4-8}$ cycloheteroalkyl, $C_{1-8}$ alkyl, $C_{2-8}$ alkenyl, $C_{2-8}$ alkynyl, $C_{3-8}$ cycloalkyl, or aralkyl can be optionally substituted with up to four independently selected $R_{15}$ groups;

wherein one or more than one of the pairs $R_4$ and $R_6$, $R_4$ and $R_7$, $R_5$ and $R_6$, $R_5$ and $R_{10}$, $R_7$ and $R_8$, $R_8$ and $R_9$ or $R_9$ and $R_{10}$, together with the carbon atom or atoms to which they attached, can form a cycloalkyl ring having 3-8 carbon atoms, or a $C_{4-8}$ cycloheteroalkyl ring;

$R_{11}$ is H, aryl, heteroaryl, aralkyl, $C_{1-8}$ alkyl, $C_{3-8}$ cycloalkyl, oxy, halogen, hydroxyalkyl, alkoxy, alkoxy-alkyl, alkenyloxy, alkynyloxy, perfluoroalkoxy, alkoxy-alkyl, $C_{1-8}$ alkanoyl, $COOR_1$, $COR_1$, $SO_2$—$C_{1-8}$ alkyl, $SO_2$-aryl, $SO_2$-heteroaryl, or CO—$NHR_1$;

wherein each of said aryl, heteroaryl, aralkyl, $C_{1-8}$ alkyl, $C_{3-8}$ cycloalkyl, $SO_2$—$C_{1-8}$ alkyl, $SO_2$-aryl and $SO_2$-heteroaryl can be optionally substituted with up to four independently selected $R_{16}$ groups;

each $R_{14}$, $R_{15}$ and $R_{16}$ is, independently, halogen, $C_{1-6}$ alkyl, $C_{2-8}$ alkenyl, $C_{2-8}$ alkynyl, $C_{3-8}$ cycloalkyl, —$OR_{17}$, CN, $COR_{12}$, $C_{1-6}$ haloalkyl, $C_{1-6}$ perhaloalkyl, $C_{1-6}$ haloalkoxy, $C_{1-6}$ perhaloalkoxy, $C_{1-6}$ perfluoroalkyl, —O—$C_{1-6}$ perfluoroalkyl, $CONR_{12}R_{13}$, —$OPO(OR_{12a})OR_{13a}$, —$PO(OR_{12a})R_{13}$, —$OC(O)OR_{12a}$, —O—$C_{1-6}$ alkyl-$NR_{12}R_{13}$, —$OC(O)NR_{12}R_{13}$, —$C(O)NR_{12}OR_{13a}$, —$COOR_{12a}$, —$SO_3H$, —$NR_{12}R_{13}$, —$N(R_{20})(C_{1-6}$ alkyl)$NR_{12}$, —$N(R_{20})COR_{13}$, —$N(R_{20})COOR_{13a}$, —$SO_2NR_{12}R_{13}$, $NO_2$, —$N(R_{20})SO_2R_{13}$, —$N(R_{20})CONR_{12}R_{13}$, —$N(R_{20})C(=NR_{13})NR_{12}R_{13}$, —$N(R_{20})C(=NR_{13})N(SO_2R_{12})R_{13}$, —$N(R_{20})C(=NR_{13})N(C=OR_{12})R_{13}$, -tetrazol-5-yl, —$SO_2NHCN$, —$SO_2NHCONR_{12}R_{13}$, aryl, phenyl, heteroaryl, —$C_{5-8}$ cycloheteroalkyl, $CH_2$—$OR_{22}$, —$SR_{22}$, —$CH_2$—$SR_{22}$, —$SO_2NR_{12}R_{13}$, —$C(=NR_{22})$—, —$C(NCN)R_{22}$—, —$CSN(R_{22})_2$, —$C(NH)N(R_{22})_2$, $NO_2$, $NO_3$, azido, hydrazino, hydroxylamino, disulfide, urea, guanidine, or —$S(O)_nR_{12}$ wherein n is 0, 1 or 2;

or any two $R_{14}$, $R_{15}$ or $R_{16}$ groups when attached to an aryl, aralkyl, heteroaryl or heteroarylalkyl group can together form a group of formula —O—$(CH_2)_k$—O— wherein k is 1 or 2;

each $R_{12}$ and $R_{13}$ is, independently, H, OH, $C_{1-8}$ alkyl, $C_{3-8}$ cycloalkyl, aryl, heteroaryl, alkoxy, alkenyloxy, alkynyloxy, perfluoroalkoxy, alkoxy-alkyl, aralkyl, or $C_{4-8}$ cycloheteroalkyl; or —$NR_{12}R_{13}$ may form a pyrrolidine, piperidine, morpholine, thiomorphohne, oxazolidine, thiazolidine, pyrazolidine, piperazine, or azetidine ring;

each $R_{12a}$ and $R_{13a}$ is, independently, H, $C_{1-8}$ alkyl, $C_{2-8}$ alkenyl, $C_{2-8}$ alkynyl, $C_{1-3}$ perfluoroalkyl, $C_{3-8}$ cycloalkyl, aryl, heteroaryl, alkoxy-alkyl, aralkyl, or $C_{4-8}$ cycloheteroalkyl;

each $R_{20}$ is, independently, H or $C_{1-6}$ alkyl;

each $R_{17}$ is, independently, H, $C_{1-8}$ alkyl, $C_{2-8}$ alkenyl, $C_{2-8}$ alkynyl, $C_{3-8}$ cycloalkyl, aryl, heteroaryl, alkoxy-alkyl, aralkyl or $C_{4-8}$ cycloheteroalkyl;

$R_{21}$ is H or $C_{1-8}$ alkyl;

each $R_{22}$ is, independently, H or $C_{1-3}$ alkyl;

A is $SO_2$ or —$P(O)$—$R_{10}$;

X is O, NH, $CH_2$ or S; and

Y is aryl or heteroaryl;

with the proviso that A and X are not bonded to adjacent atoms of Y;

or a pharmaceutically acceptable salt or prodrug thereof.

In some embodiments, A is $SO_2$. In some further embodiments, X is O. In some further embodiments, Y is aryl, preferably phenyl.

In some further embodiments, Y is heteroaryl, preferably pyridyl, thienyl, furanyl, imidazolyl, triazolyl or thiadiazolyl.

In some embodiments, $R_1$ is H or $C_{1-6}$ alkyl. In some further embodiments, $R_2$ and $R_3$ are each H. In still further embodiments, $R_7$ is H. In some embodiments, $R_2$, $R_3$ and $R_7$ are each H.

In some embodiments, $R_1$ is H or $C_{1-6}$ alkyl; $R_2$, $R_3$ and $R_7$ are each H; A is $SO_2$; X is O; and Y aryl, preferably phenyl.

In some preferred embodiments, the compounds of the invention have the Formula II:

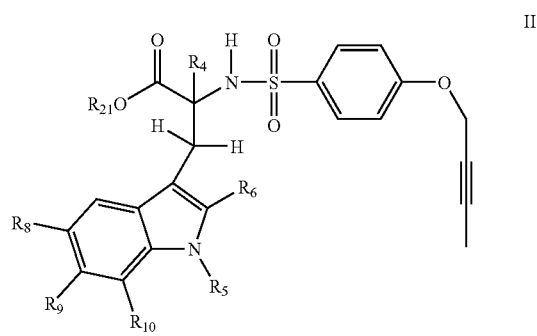

II wherein the constituent variables are as described above.

In some embodiments of the compounds having Formula II, $R_5$ is H, $C_{1-6}$ alkyl, $C_{2-8}$ alkenyl, arylalkyl, cycloalkylalkyl, $CO_2R_{11}$, aryloxyalkyl or heteroarylalkyl, wherein said arylalkyl is optionally substituted with up to four substituents independently selected from the group consisting of $C_{1-6}$ alkyl, halogen, $C_{1-8}$ alkoxy, aryl, phenyl, $C_{1-3}$ haloalkyl, $C_{1-3}$ perhaloalkyl, $C_{1-3}$ haloalkoxy, $C_{1-3}$ perhaloalkoxy, CN, alkenyloxy, $CO_2H$ and OH, wherein any two adjacent hydroxyl groups attached to the aryl moiety of said arylalkyl can be joined together to form a 1,3-dioxolane group; $R_6$ is H or $C_{1-6}$ alkyl; $R_8$ is H, $C_{1-6}$ alkyl, $C_{1-6}$ alkoxy, OH, arylalkoxy, halogen, $CO_2H$ or CN; $R_9$ is H, halogen or $C_{1-6}$ alkyl; $R_{10}$ is H or $C_{1-6}$ alkyl; and $R_{11}$ is $C_{1-6}$ alkyl.

In some embodiments of the compounds of Formula II, $R_4$ is H. In further embodiments of the compounds of Formula II, $R_5$ is H or arylalkyl, wherein said arylalkyl is optionally substituted with up to three $C_{1-3}$ alkoxy groups. In further embodiments of the compounds of Formula II, $R_6$ is H or methyl. In further embodiments of the compounds of Formula II, $R_8$ is H, halogen, $C_{1-3}$ alkyl, or $C_{1-3}$ alkoxy. In still further embodiments of the compounds of Formula II, $R_9$ is H, or $R_{10}$ is H, or $R_9$ and $R_{10}$ are each H. In further embodiments of the compounds of Formula II, $R_4$, $R_9$ and $R_{10}$ are each H.

In further embodiments of the compounds of Formula II, $R_4$, $R_9$ and $R_{10}$ are each H; $R_5$ is H or arylalkyl, wherein said arylalkyl is preferably benzyl, which is optionally substituted with up to three $C_{1-3}$ alkoxy groups, preferably methoxy groups; $R_6$ is H or methyl; and $R_8$ is H, halogen, $C_{1-3}$ alkyl, preferably methyl, or $C_{1-3}$ alkoxy, preferably methoxy.

Also provided in accordance with the present invention are pharmaceutically acceptable salts, and prodrugs, of the compounds disclosed herein.

The compounds of the present invention are useful for the treatment of disease conditions mediated by TNF-α, such as rheumatoid arthritis (RA), juvenile RA, psoriatic arthritis, ankylosing spondylitis, psoriasis, osteoarthritis, tumor metastasis, sepsis, AIDS, ulcerative colitis, multiple sclerosis, diabetes (insulin resistance), Crohn's disease, degenerative cartilage loss, asthma, idiopathic pulmonary fibrosis, vasculitis, systemic lupus erythematosus, irritable bowel syndrome, acute coronary syndrome, hepatitis C, cachexia, COPD, and type 2 diabetes and for the alleviation of symptoms thereof. Accordingly, the present invention further provides methods of treating these diseases and disorders using the compounds described herein. In some embodiments, the methods include identifying a mammal having a disease or disorder mediated by TNF-α, and providing to the mammal an effective amount of a compound as described herein.

In further embodiments, the methods are provided for alleviating a symptom of a disease or disorder mediated by TNF-α. In some embodiments, the methods include identifying a mammal having a symptom of a disease or disorder mediated by TNF-α, and providing to the mammal an amount of a compound as described herein effective to ameliorate (i.e., lessen the severity of) the symptom.

Pharmaceutically acceptable salts of the compounds of Formula (I) having an acidic moiety can be formed from organic and inorganic bases. Suitable salts with bases are, for example, metal salts, such as alkali metal or alkaline earth metal salts, for example sodium, potassium, or magnesium salts; or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethyl-propylamine, or a mono-, di-, or trihydroxy lower alkylamine, for example mono-, di- or triethanolamine. Internal salts may furthermore be formed. Similarly, when a compound of the present invention contains a basic moiety, salts can be formed from organic and inorganic acids. For example salts can be formed from acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known pharmaceutically acceptable acids.

The present invention also includes prodrugs of the compounds described herein. As used herein, "prodrug" refers to a moiety that releases a compound of the invention when administered to a mammalian subject. Prodrugs can be prepared by modifying functional groups present in the compounds in such a way that the modifications are cleaved, either in routine manipulation or in vivo, to the parent compounds. Examples of prodrugs include compounds of the invention as described herein that contain one or more molecular moieties appended to a hydroxyl, amino, sulfhydryl, or carboxyl group of the compound, and that when administered to a mammalian subject, cleaves in vivo to form the free hydroxyl, amino, sulfhydryl, or carboxyl group, respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entireties.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, s-butyl, t-butyl), pentyl (e.g., n-pentyl, isopentyl, neopentyl) and the like. Alkyl groups can contain from 1 to about 20, 1 to about 10, 1 to about 8, 1 to about 6, 1 to about 4, or 1 to about 3 carbon atoms. In some embodiments, alkyl groups can be substituted with up to four substituent groups, as described below. As used herein, the term "lower alkyl" is intended to mean alkyl groups having up to six carbon atoms.

As used herein, "alkenyl" refers to an alkyl group having one or more double carbon-carbon bonds. Example alkenyl groups include ethenyl, propenyl, butenyl, pentenyl, hexenyl, butadienyl, pentadienyl, hexadienyl, and the like. In some embodiments, alkenyl groups can be substituted with up to four substituent groups, as described below.

As used herein, "alkynyl" refers to an alkyl group having one or more triple carbon-carbon bonds. Examples of alkynyl groups include ethynyl, propynyl, butynyl, pentynyl, and the like. In some embodiments, alkynyl groups can be substituted with up to four substituent groups, as described below.

As used herein, "cycloalkyl" refers to non-aromatic carbocyclic groups including cyclized alkyl, alkenyl, and alkynyl groups. Cycloalkyl groups can be monocyclic (e.g., cyclohexyl) or poly-cyclic ring (e.g., 2, 3, or 4 fused ring) systems. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo derivatives of cyclopentane (indanyl), cyclohexane (tetrahydronaphthyl), and the like.

As used herein "cycloalkylalkyl" refers to a group of formula -alkyl-cycloalkyl, for example a cyclopropylmethyl group.

As used herein, "hydroxy" or "hydroxyl" refers to OH.

As used herein, "halo" or "halogen" includes fluoro, chloro, bromo, and iodo.

As used herein, "cyano" refers to CN.

As used herein, "alkoxy" refers to an —O-alkyl group. Example alkoxy groups include methoxy, ethoxy, propoxy (e.g., n-propoxy and isopropoxy), t-butoxy, and the like. An alkoxy group can contain from 1 to about 20, 1 to about 10, 1 to about 8, 1 to about 6, 1 to about 4, or 1 to about 3 carbon atoms. In some embodiments, alkoxy groups can be substituted with up to four substituent groups, as described below.

As used herein, "alkenyloxy" refers to an —O-alkenyl group. Examples of alkenyloxy groups include prop-3-enyloxy, but-2-enyloxy, but-3-enyloxy, pent-2-enyloxy, 2-methyl-pent-3-enyloxy and the like. Alkenyloxy groups can contain from 2 to about 20, 2 to about 10, 2 to about 8, 2 to about 6, 2 to about 4, or 2 to about 3 carbon atoms.

As used herein, "alkynyloxy" refers to an —O-alkynyl group. Examples of alkenyloxy groups include prop-3-ynyloxy, but-2-ynyloxy, but-3-ynyloxy, pent-2-ynyloxy, 2-methyl-pent-3-ynyloxy and the like. Alkynyloxy groups can contain from 2 to about 20, 2 to about 10, 2 to about 8, 2 to about 6, 2 to about 4, or 2 to about 3 carbon atoms.

As used herein, the term "perfluoroalkoxy" indicates a group of formula —O-perfluoroalkyl.

As used herein, "haloalkyl" refers to an alkyl group having one or more halogen substituents. Examples of haloalkyl groups include $CF_3$, $C_2F_5$, $CHF_2$, $CCl_3$, $CHCl_2$, $C_2Cl_5$, and the like. An alkyl group in which all of the hydrogen atoms are replaced with halogen atoms can be referred to as "perhaloalkyl." Examples perhaloalkyl groups include $CF_3$ and $C_2F_5$.

As used herein, "haloalkoxy" refers to an —O-haloalkyl group.

As used herein, "aryl" refers to aromatic carbocyclic groups including monocyclic or polycyclic aromatic hydrocarbons such as, for example, phenyl, 1-naphthyl, 2-naphthyl anthracenyl, phenanthrenyl, and the like. In some embodiments, aryl groups have from 6 to about 20 carbon atoms. In some preferred embodiments, aryl groups are phenyl or naphthyl groups that optionally contain up to four, preferably up to 2, substituent groups as described below.

As used herein, "heteroaryl" is intended to refer to aromatic heterocyclic groups that have at least one heteroatom ring member selected from N, S and O. In some embodiments, one or more ring nitrogen atoms can bear a substituent as described herein. In some embodiments, heteroaryl groups can be monocyclic systems or polycyclic aromatic ring systems having from 5 to 10 ring atoms. Examples of heteroaryl groups include, without limitation, the following:

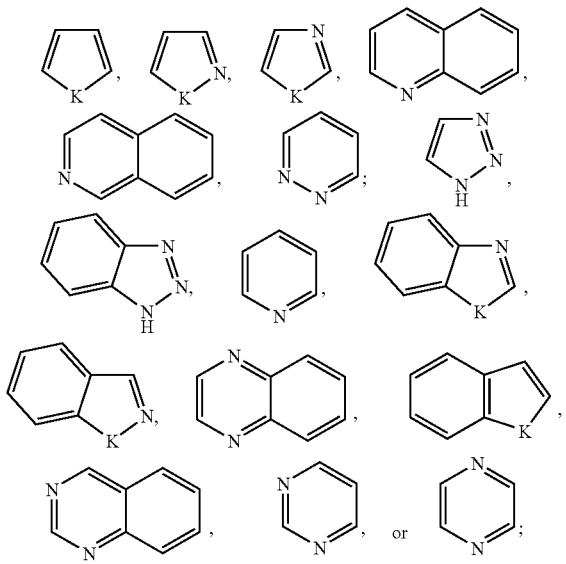

wherein K is defined as O, S, N or $NR_{11}$, where $R_{11}$ is as defined supra. Examples of some preferred heteroaryl rings include pyrrole, furan, thiophene, pyridine, pyrimidine, pyridazine, pyrazine, triazole, pyrazole, imidazole, isothiazole, thiazole, isoxazole, oxazole, indole, isoindole, benzofuran, benzothiophene, quinoline, isoquinoline, quinoxaline, quinazoline, benzotriazole, indazole, benzimidazole, benzothiazole, benzisoxazole, and benzoxazole. In some preferred embodiments, heteroaryl groups can be substituted with up to four, preferably up to 2, substituent groups as described below.

As used herein, "aryloxy" refers to an —O-aryl group, for example and not with limitation, phenoxy.

As used herein, "arylalkyl" or "aralkyl" refers to a group of formula -alkyl-aryl. Preferably, the alkyl portion of the arylalkyl group is a lower alkyl group, i.e., a $C_{1-6}$ alkyl group, more preferably a $C_{1-3}$ alkyl group. Examples of aralkyl groups include benzyl and naphthylmethyl groups. In some preferred embodiments, arylalkyl groups can be optionally substituted with up to four, preferably up to 2, substituent groups as described below.

As used herein, "heteroarylalkyl" or "heteroaralkyl" refers to a group of formula -alkyl-heteroaryl. Nonlimiting examples of heteroaralkyl groups include pyridylmethyl and pyrrolemethyl groups. In some preferred embodiments, heteroarylalkyl groups can be substituted with up to four, preferably up to 2, substituent groups as described below.

At various places in the present specification substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, propyl, isopropyl, n-butyl, sec-butyl, isobutyl, etc.

In some embodiments, the alkyl, alkenyl, alkynyl, cycloalkyl, cycloalkylalkyl, alkoxy, alkenyloxy, alkynyloxy, haloalkyl, haloalkoxy, aryl, heteroaryl, aryloxy, arylalkyl and heteroarylalkyl groups of the compounds of the invention can be substituted with one or more, preferably up to four, and more preferably one or two substituent groups. Examples of suitable substituent groups include halogen, $C_{1-6}$ alkyl, $C_{2-8}$ alkenyl, $C_{2-8}$ alkynyl, $C_{3-8}$ cycloalkyl, —$OR_{17}$, CN, $COR_{12}$, $C_{1-6}$ haloalkyl, $C_{1-6}$ perhaloalkyl, $C_{1-6}$ haloalkoxy, $C_{1-6}$ perhaloalkoxy, $C_{1-6}$ perfluoroalkyl, —O—$C_{1-6}$ perfluoroalkyl, $CONR_{12}R_{13}$, —$OPO(OR_{12a})OR_{13a}$, —$PO(OR_{12a})R_{13}$, —$OC(O)OR_{12a}$, —O—$C_{1-6}$ alkyl-$NR_{12}R_{13}$, —OC(O)$NR_{12}R_{13}$, —C(O)$NR_{12}OR_{13a}$, —$COOR_{12a}$, —$SO_3H$, —$NR_{12}R_{13}$, —$N(R_{20})(C_{1-6}$ alkyl)$NR_{12}$, —$N(R_{20})COR_{13}$, —$N(R_{20})COOR_{13a}$, —$SO_2NR_{12}R_{13}$, $NO_2$, —$N(R_{20})SO_2R_{13}$, —$N(R_{20})CONR_{12}R_{13}$, —$N(R_{20})C(=NR_{13})NR_{12}R_{13}$, —$N(R_{20})C(=NR_{13})N(SO_2R_{12})R_{13}$, —$N(R_{20})C(=NR_{13})N(C=OR_{12})R_{13}$, -tetrazol-5-yl, —$SO_2NHCN$, —$SO_2NHCONR_{12}R_{13}$, aryl, phenyl, heteroaryl, —$C_{5-8}$ cycloheteroalkyl, $CH_2$—$OR_{22}$, —$SR_{22}$, —$CH_2$—$SR_{22}$, —$SO_2NR_{12}R_{13}$, —C(=$NR_{22}$)—, —C(NCN)$R_{22}$—, —CSN$(R_{22})_2$, —C(NH)N($R_{22})_2$, $NO_2$, $NO_3$, azido, hydrazino, hydroxylamino, disulfide, urea, guanidine or —$S(O)_nR_{12}$ wherein n is 0, 1 or 2;

wherein:

each $R_{12}$ and $R_{13}$ is, independently, H, OH, $C_{1-8}$ alkyl, $C_{3-8}$ cycloalkyl, aryl, heteroaryl, alkoxy, alkenyloxy, alkynyloxy, perfluoroalkoxy, alkoxy-alkyl, aralkyl, or $C_{4-8}$ cycloheteroalkyl; or —$NR_{12}R_{13}$ can form a pyrrolidine, piperidine, morpholine, thiomorphohne, oxazolidine, thiazolidine, pyrazolidine, piperazine, or azetidine ring;

each $R_{12a}$ and $R_{13a}$ is, independently, H, $C_{1-8}$ alkyl, $C_{2-8}$ alkenyl, $C_{2-8}$ alkynyl, $C_{1-3}$ perfluoroalkyl, $C_{3-8}$ cycloalkyl, aryl, heteroaryl, alkoxy-alkyl, aralkyl, or $C_{4-8}$ cycloheteroalkyl;

each $R_{20}$ is, independently, H or $C_{1-6}$ alkyl; and each $R_{22}$ is, independently, H or $C_{1-3}$ alkyl.

Examples of some preferred substituents include halogen, $CH_3$, $C_2H_5$, vinyl, allyl, —C≡CH, —OH, $OCH_3$, $OCH_2CH_3$, SH, $SCH_3$, $SCH_2CH_3$, $CF_3$, $CF_2CF_3$, $OCF_3$, $OCF_2CF_3$, CN, COH, $CONH_2$, $SOCH_3$, $SO_2CH_3$, $SO_3H$, $CO_2H$, $CO_2CH_3$, —$OCO_2H$, —$OCO_2CH_3$, —$OCH_2NH_2$, —C(O)$NH_2$, —C(O)N($CH_3)_2$, —OC(O)$NH_2$, —OC(O)N$(CH_3)_2$, —$NH_2$, —N$(CH_3)_2$, —$NHCOCH_3$, —$SO_2NH_2$, $SO_2N(CH_3)_2$, $NO_2$, —$NHSO_2CH_3$, —$NHCONH_2$, —NHCON$(CH_3)_2$, $CH_2OH$, —SH, —$SCH_3$, —$CH_2$—SH, $CH_2$—$SCH_3$, —$SO_2NH_2$, —C(=NH)—, $NO_2$, $NO_3$, azido, hydrazino, hydroxylamino, disulfide, urea or guanidine.

As used in accordance with this invention, the term "providing," with respect to providing a compound or substance covered by this invention, means either directly administering such a compound or substance, or administering a prodrug, derivative, or analog which will form the effective amount of the compound or substance within the body. This invention also covers providing the compounds of this invention to treat the disease states disclosed herein that the compounds are useful for treating.

The compounds of the present invention can contain an asymmetric atom (also referred as a chiral center), and some of the compounds can contain one or more asymmetric atoms or centers, which can thus give rise to optical isomers (enantiomers) and diastereomers. The present invention includes such optical isomers (enantiomers) and diastereomers (geometric isomers); as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, and include, but are not limited to, diastereomeric salt formation, kinetic resolution, and asymmetric synthesis. It is also understood that this invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

The novel compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of present invention can be conveniently prepared in accordance with the procedures outlined in the schemes below, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds of the invention.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis,* 2d. Ed., Wiley & Sons, 1991, which is incorporated herein by reference in its entirety.

The reactions of the processes described herein can be carried out in suitable solvents, which can be readily selected by one of skill in the art of organic synthesis. Suitable solvents can be substantially nonreactive with the starting materials (reactants), the intermediates, or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

Although not wishing to be limited to any source, publications and literatures such as PCT Application No, WO 200044723; Li, J. P., et al. *Synthesis,* 1988, 73-76; Gilchrist, T. L. and T. G. Roberts, *J. Chem. Soc. Perkin. Trans* 1 1983, 1283-1292 are useful and recognized references of organic synthesis known to those in the art. Each of the foregoing is incorporated herein by reference in its entirety.

General Schemes for the Preparation of the Present Invention Compounds

Compounds of the invention can be prepared according to the convenient synthetic route in Scheme 1.

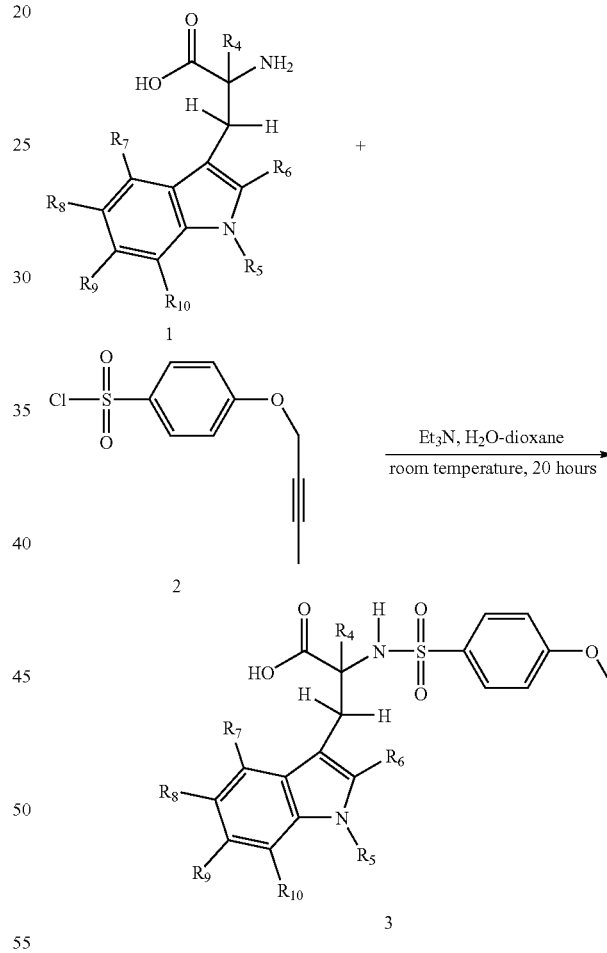

As shown in Scheme 1, a mono or poly substituted tryptophan derivative 1 is reacted with 4-but-2-ynyloxy-benzenesulfonyl chloride 2 (prepared by using the procedures described in WO 200044723, incorporated by reference herein in its entirety) in the presence of base such as triethylamine at room temperature to afford arylsulfonamido tryptophan derivative 3. Tryptophan derivatives 1 are commercially available, or can be synthesized using standard methods known to those skilled in the art.

Compounds of the present invention also can be prepared according to the synthetic route shown in Scheme 2.

Scheme 2

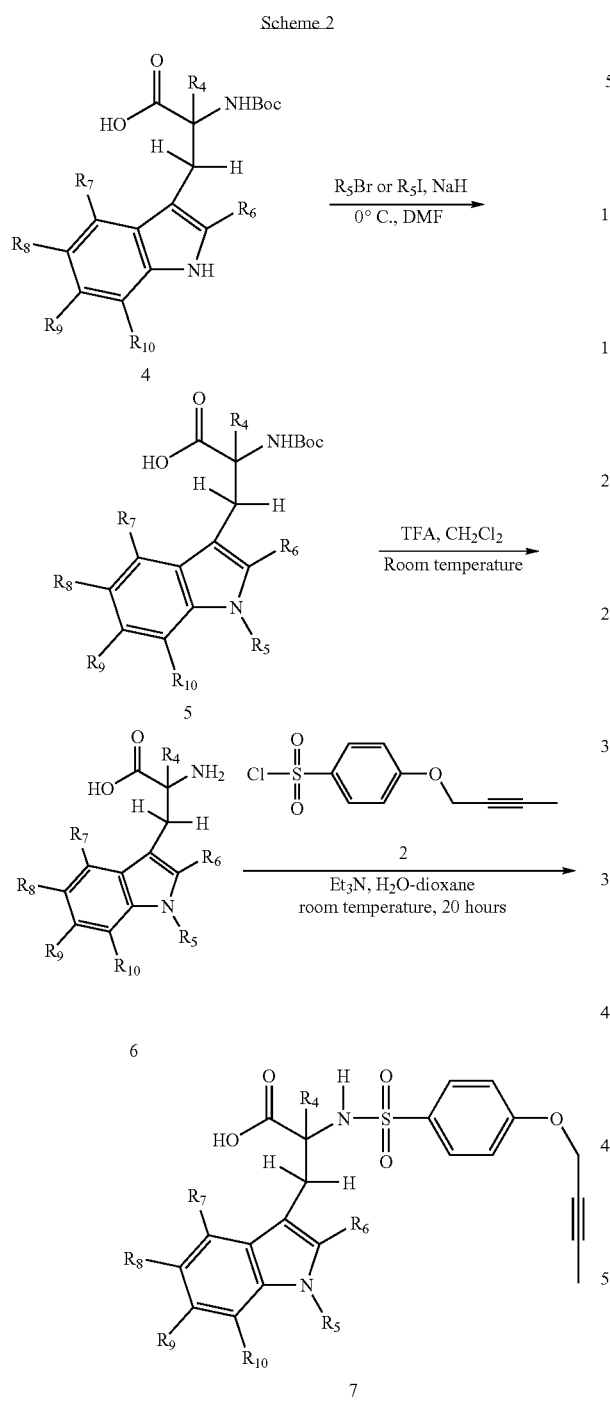

Scheme 3

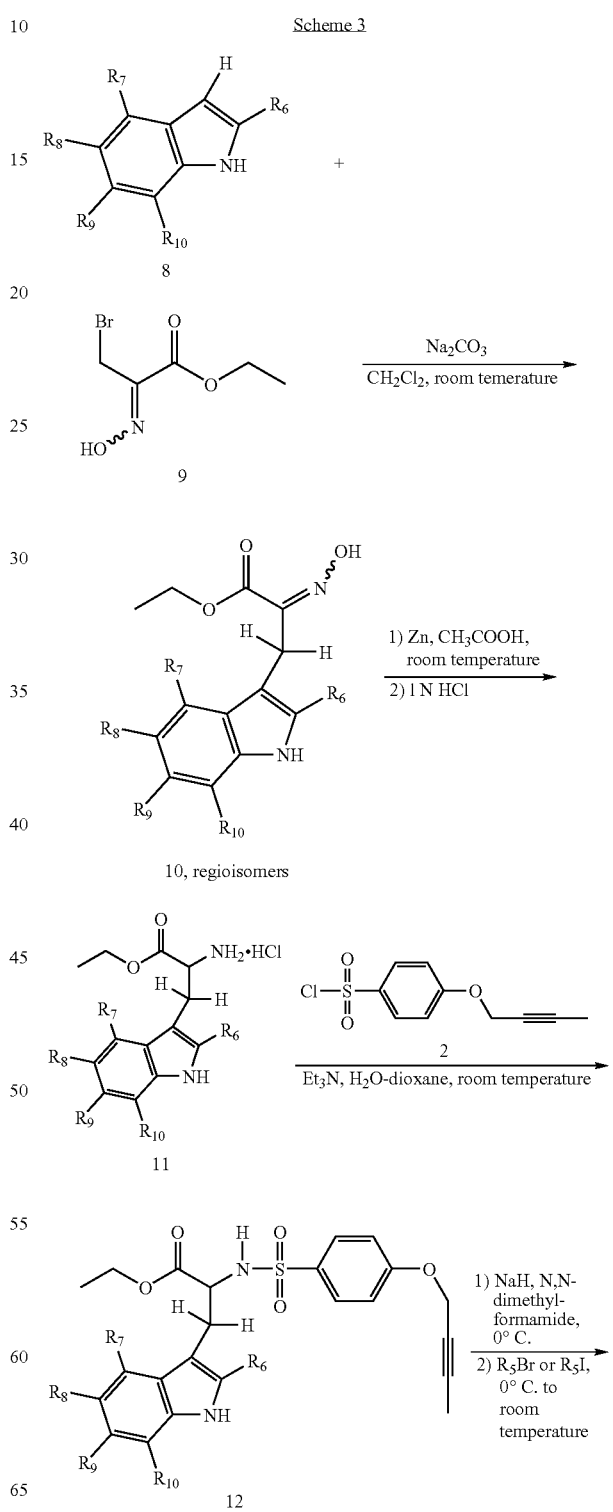

such as triethylamine at room temperature produces the arylsulfonamido tryptophan derivative 7. The overall yields from the three steps shown in Scheme 2 are generally moderate (i.e., 50%-60%) to high (i.e., 80%-90%).

Compounds of the present invention also can be prepared according to the synthetic route in Scheme 3, below.

As shown in Scheme 2, an N-Boc-protected tryptophan derivative 4 is reacted with a halide such as $R_5Br$ or $R_5I$ in the presence of base such as NaH at low temperature (0° C.) to afford a substituted N-Boc-protected tryptophan derivative 5. Tryptophan derivatives 4 are commercially available, or can be synthesized using standard methods known to those skilled in the art. The Boc protecting group is then removed under acidic conditions, for example, using trifluoroacetic acid (TFA) in a solvent such as dichloromethane, to afford a substituted tryptophan 6. Coupling of 6 with 4-but-2-ynyloxy-benzenesulfonyl chloride 2 in the presence of a base

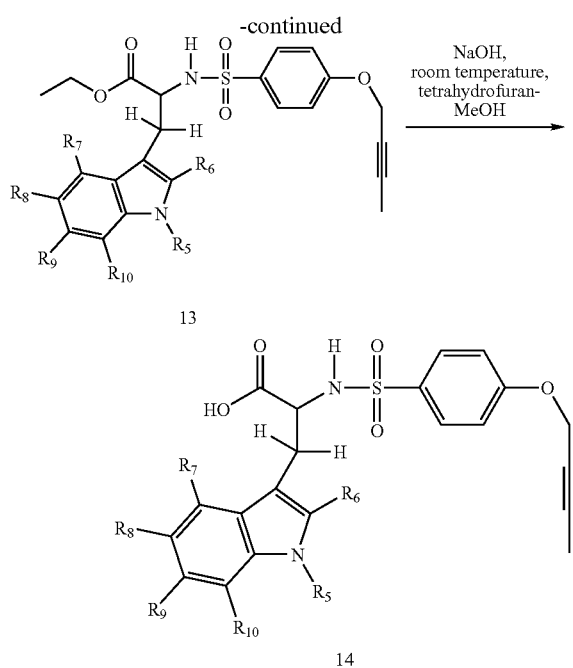

As shown in Scheme 3, an indole derivative 8 is reacted with oxime 9 in the presence of base, such as $Na_2CO_3$, in solvent, such as methylene chloride, at room temperature to afford an indole-oxime complex 10 as regioisomers. Oxime 9 is prepared by using literature procedures described in (a) Li, J. P. et al. *Synthesis*, 1988, 73-76 or (b) Gilchrist, T. L. and T. G. Roberts, *J. Chem. Soc. Perkin. Trans* 1 1983, 1283-1292, each of which is incorporated herein by reference in its entirety. The reduction of complex 10 to tryptophan ester ammonium salt 11 is achieved by 1) treating complex 10 with zinc powder in acetic acid to reduce the oxime to an amino group; followed by 2) conversion of the amino group into the ammonium salt with hydrochloric acid. Coupling of 11 with 4-but-2-ynyloxy-benzenesulfonyl chloride 2 in the presence of base such as triethylamine at room temperature produces arylsulfonamido tryptophan ester derivative 12. The arylsulfonamido tryptophan ester derivative 12 is reacted with a desired halide such as $R_5Br$ or $R_5I$ in the presence of base such as NaH at low temperature (0° C.) to afford another substituted arylsulfonamido tryptophan ester derivative 13. Hydrolysis of the ester group of 13 with base, such as a 2N aqueous NaOH solution, in solvent, such as a methanol/tetrahydrofuran mixture, at room temperature affords arylsulfonamido tryptophan derivative 14. The overall yield of the five steps from 8 to 14 is generally about 20% to about 50%.

EXAMPLES

Examples 1-224

Preparation of Compounds of the Invention

The following describes the preparation of representative compounds of this invention in greater detail. The following examples are offered for illustrative purposes, and are not intended to limit the invention in any manner. Those of skill in the art will readily recognize a variety of noncritical parameters that can be changed or modified to yield essentially the same results.

Mass spectral data is reported as the mass-to-charge ratio, m/z, and for high resolution mass spectral data, the calculated and experimentally found masses, $[M+H]^+$, for the neutral formulae M are reported. Nuclear magnetic resonance data is reported as δ in parts per million (ppm) downfield from the standard, tetramethylsilane, along with the solvent, nucleus, and field strength parameters. The spin-spin homonuclear coupling constants are reported as J values in hertz, and the multiplicities are reported as a: s, singlet; d, doublet; t, triplet; q, quartet; quintet; or br, broadened.

General Methods

1. Semi-Preparative RP-HPLC Conditions:
    Gilson Semi-Preparative Reverse Phase HPLC system with Unipoint Software
    Column: 50×19 mm Xterra C18, 5 micron column at 50° C.
    Solvent A: Water (0.02% TFA buffer); Solvent B: Acetonitrile (0.02% TFA buffer)
    Solvent Gradient (16 min method): Time 0: 10% B; 2.5 min: 10% B; 12 min: 95% B; 14 min: 95% B; 14.1 min: 10% B; 16 min: 10% B
    Flow rate: 22.5 mL/min
    Detection: 254 nm DAD 2. Analytical LCMS Conditions:
    Hewlett Packard 1100 MSD with ChemStation Software
    Column: 30×2.1 mm Xterra C18 MS, 5 micron particle size at 50° C.
    Solvent A: Water (0.02% formic acid buffer)
    Solvent B: Acetonitrile (0.02% formic acid buffer)
    Gradient: Time 0: 5% B; 3.5 min: 95% B; 5 min: 95% B
    Flow rate 1.0 mL/min
    Injection volume: 5 μL
    Sample concentration: ~2.0 mM
    Detection: 220 nm, 254 nm DAD; API-ES Scanning Mode Positive 150-700; Fragmentor 70 mV The following compounds were prepared using the procedures of Schemes 1-3 described above:

| Example | Compound Name | Calculated MW | LCMS Retention Time (min) | Observed MW |
|---|---|---|---|---|
| 1 | N-{[4-(but-2-ynyloxy)phenyl]sulfonyl}-D-tryptophan | 412 | 2.45 | 413 [M + H] |
| 2 | N-{[4-(but-2-ynyloxy)phenyl]sulfonyl}-L-tryptophan | 412 | 2.39 | 413 [M + H] |

-continued

| Example | Compound Name | Calculated MW | LCMS Retention Time (min) | Observed MW |
|---|---|---|---|---|
| 3 | N-{[4-(but-2-ynyloxy)phenyl]sulfonyl}-5-fluorotryptophan | 430 | 2.60 | 431 [M + H] |
| 4 | N-{[4-(but-2-ynyloxy)phenyl]sulfonyl}-5-methoxytryptophan | 442 | 2.50 | 443 [M + H] |
| 5 | N-{[4-(but-2-ynyloxy)phenyl]sulfonyl}-5-hydroxytryptophan | 428 | 2.14 | 429 [M + H] |
| 6 | N-{[4-(but-2-ynyloxy)phenyl]sulfonyl}-5-methyltryptophan | 426 | 2.69 | 427 [M + H] |
| 7 | N-{[4-(but-2-ynyloxy)phenyl]sulfonyl}-6-fluorotryptophan | 430 | 2.61 | 431 [M + H] |
| 8 | N-{[4-(but-2-ynyloxy)phenyl]sulfonyl}-6-methyltryptophan | 426 | 2.70 | 427 [M + H] |
| 9 | N-{[4-(but-2-ynyloxy)phenyl]sulfonyl}-alpha-methyltryptophan | 426 | 2.72 | 427 [M + H] |
| 10 | N-{[4-(but-2-ynyloxy)phenyl]sulfonyl}-7-methyltryptophan | 426 | 2.67 | 427 [M + H] |
| 11 | N-{[4-(but-2-ynyloxy)phenyl]sulfonyl}-5-hydroxy-L-tryptophan | 428 | 2.13 | 429 [M + H] |
| 12 | N-{[4-(but-2-ynyloxy)phenyl]sulfonyl}-1-propyl-L-tryptophan | 455 | 3.03 | 456 [M + H] |
| 13 | 1-butyl-N-{[4-(but-2-ynyloxy)phenyl]sulfonyl}-L-tryptophan | 469 | 3.19 | 470 [M + H] |
| 14 | N-{[4-(but-2-ynyloxy)phenyl]sulfonyl}-1-isobutyl-L-tryptophan | 469 | 3.17 | 470 [M + H] |
| 15 | 1-allyl-N-{[4-(but-2-ynyloxy)phenyl]sulfonyl}-L-tryptophan | 453 | 2.95 | 454 [M + H] |
| 16 | N-{[4-(but-2-ynyloxy)phenyl]sulfonyl}-1-(3-methylbenzyl)-L-tryptophan | 517 | 3.26 | 518 [M + H] |
| 17 | N-{[4-(but-2-ynyloxy)phenyl]sulfonyl}-1-(4-methylbenzyl)-L-tryptophan | 517 | 3.27 | 518 [M + H] |
| 18 | N-{[4-(but-2-ynyloxy)phenyl]sulfonyl}-1-(4-chlorobenzyl)-L-tryptophan | 537 | 3.30 | 538 [M + H] |
| 19 | N-{[4-(but-2-ynyloxy)phenyl]sulfonyl}-1-(4-methoxybenzyl)-L-tryptophan | 533 | 2.97 | 534 [M + H] |
| 20 | 5-(benzyloxy)-N-{[4-(but-2-ynyloxy)phenyl]sulfonyl}tryptophan | 518 | 2.99 | 519 [M + H] |
| 21 | N-{[4-(but-2-ynyloxy)phenyl]sulfonyl}-1-methyl-D-tryptophan | 426 | 2.76 | 427 [M + H] |
| 22 | N-{[4-(but-2-ynyloxy)phenyl]sulfonyl}-1-pentyl-D-tryptophan | 483 | 3.19 | 484 [M + H] |
| 23 | N-{[4-(but-2-ynyloxy)phenyl]sulfonyl}-1-(cyclohexylmethyl)-D-tryptophan | 509 | 3.31 | 510 [M + H] |
| 24 | N-{[4-(but-2-ynyloxy)phenyl]sulfonyl}-1-(4-phenoxybutyl)-D-tryptophan | 561 | 3.27 | 562 [M + H] |
| 25 | 1-benzyl-N-{[4-(but-2-ynyloxy)phenyl]sulfonyl}-D-tryptophan | 503 | 3.00 | 504 [M + H] |
| 26 | N-{[4-(but-2-ynyloxy)phenyl]sulfonyl}-1-(4-methylbenzyl)-D-tryptophan | 517 | 3.13 | 518 [M + H] |
| 27 | 1-(1,1'-biphenyl-2-ylmethyl)-N-{[4-(but-2-ynyloxy)phenyl]sulfonyl}-D-tryptophan | 579 | 3.34 | 580 [M + H] |

-continued

| Example | Compound Name | Calculated MW | LCMS Retention Time (min) | Observed MW |
|---|---|---|---|---|
| 28 | N-{[4-(but-2-ynyloxy)phenyl]sulfonyl}-1-(4-fluorobenzyl)-D-tryptophan | 521 | 3.02 | 522 [M + H] |
| 29 | N-{[4-(but-2-ynyloxy)phenyl]sulfonyl}-1-(2-naphthylmethyl)-D-tryptophan | 553 | 3.32 | 554 [M + H] |
| 30 | N-{[4-(but-2-ynyloxy)phenyl]sulfonyl}-1-(pyridin-3-ylmethyl)-D-tryptophan | 504 | 2.29 | 505 [M + H] |
| 31 | N-{[4-(but-2-ynyloxy)phenyl]sulfonyl}-1-(cyclopropylmethyl)-D-tryptophan | 467 | 3.02 | 468 [M + H] |
| 32 | N-{[4-(but-2-ynyloxy)phenyl]sulfonyl}-1-(cyclobutylmethyl)-D-tryptophan | 480 | 3.22 | 481 [M + H] |
| 33 | N-{[4-(but-2-ynyloxy)phenyl]sulfonyl}-1-(2-cyclohexylethyl)-D-tryptophan | 523 | 3.44 | 522 [M − H] |
| 34 | N-{[4-(but-2-ynyloxy)phenyl]sulfonyl}-1-(3-methoxybenzyl)-D-tryptophan | 533 | 3.12 | 534 [M + H] |
| 35 | N-{[4-(but-2-ynyloxy)phenyl]sulfonyl}-1-(4-methoxybenzyl)-D-tryptophan | 533 | 2.80 | 532 [M − H] |
| 36 | N-{[4-(but-2-ynyloxy)phenyl]sulfonyl}-1-(3,5-dimethoxybenzyl)-D-tryptophan | 563 | 3.12 | 564 [M + H] |
| 37 | 1-(1,3-benzodioxol-5-ylmethyl)-N-{[4-(but-2-ynyloxy)phenyl]sulfonyl}-D-tryptophan | 547 | 2.92 | 548 [M + H] |
| 38 | N-{[4-(but-2-ynyloxy)phenyl]sulfonyl}-1-[4-(trifluoromethoxy)benzyl]-D-tryptophan | 587 | 3.40 | 588 [M + H] |
| 39 | N-{[4-(but-2-ynyloxy)phenyl]sulfonyl}-1-[2-(trifluoromethyl)benzyl]-D-tryptophan | 570 | 3.37 | 571 [M + H] |
| 40 | N-{[4-(but-2-ynyloxy)phenyl]sulfonyl}-1-[3-(trifluoromethyl)benzyl]-D-tryptophan | 570 | 3.27 | 569 [M − H] |
| 41 | N-{[4-(but-2-ynyloxy)phenyl]sulfonyl}-1-[4-(trifluoromethyl)benzyl]-D-tryptophan | 570 | 3.33 | 571 [M + H] |
| 42 | N-{[4-(but-2-ynyloxy)phenyl]sulfonyl}-1-(4-chlorobenzyl)-D-tryptophan | 537 | 3.56 | 536 [M − H] |
| 43 | N-{[4-(but-2-ynyloxy)phenyl]sulfonyl}-1-(2-cyanobenzyl)-D-tryptophan | 528 | 3.00 | 529 [M + H] |
| 44 | N-{[4-(but-2-ynyloxy)phenyl]sulfonyl}-1-(3-cyanobenzyl)-D-tryptophan | 528 | 2.98 | 529 [M + H] |
| 45 | N-{[4-(but-2-ynyloxy)phenyl]sulfonyl}-1-(4-cyanobenzyl)-D-tryptophan | 528 | 2.98 | 529 [M + H] |
| 46 | 5-bromo-N-{[4-(but-2-ynyloxy)phenyl]sulfonyl}tryptophan | 491 | 2.75 | 490 [M − H] |
| 47 | N-{[4-(but-2-ynyloxy)phenyl]sulfonyl}-1-(4-methoxybenzyl)-5-methyltryptophan | 546 | 2.76 | 545 [M − H] |
| 48 | 1-benzyl-N-{[4-(but-2-ynyloxy)phenyl]sulfonyl}-5-methoxytryptophan | 532 | 2.90 | 533 [M + H] |
| 49 | N-{[4-(but-2-ynyloxy)phenyl]sulfonyl}-5-methoxy-1-(2-methylbenzyl)tryptophan | 546 | 3.02 | 547 [M + H] |
| 50 | N-{[4-(but-2-ynyloxy)phenyl]sulfonyl}-5-methoxy-1-(3-methylbenzyl)tryptophan | 546 | 1.90 | 547 [M + H] |

-continued

| Example | Compound Name | Calculated MW | LCMS Retention Time (min) | Observed MW |
|---|---|---|---|---|
| 51 | N-{[4-(but-2-ynyloxy)phenyl]sulfonyl}-5-methoxy-1-(2-methoxybenzyl)tryptophan | 562 | 1.88 | 563 [M + H] |
| 52 | N-{[4-(but-2-ynyloxy)phenyl]sulfonyl}-5-methoxy-1-(3-methoxybenzyl)tryptophan | 562 | 1.85 | 563 [M + H] |
| 53 | N-{[4-(but-2-ynyloxy)phenyl]sulfonyl}-5-methoxy-1-(4-methoxybenzyl)tryptophan | 562 | 1.85 | 563 [M + H] |
| 54 | N-{[4-(but-2-ynyloxy)phenyl]sulfonyl}-1-(3,5-dimethoxybenzyl)-5-methoxytryptophan | 592 | 1.86 | 593 [M + H] |
| 55 | N-{[4-(but-2-ynyloxy)phenyl]sulfonyl}-5-methoxy-1-[2-(trifluoromethyl)benzyl]tryptophan | 600 | 1.97 | 601 [M + H] |
| 56 | N-{[4-(but-2-ynyloxy)phenyl]sulfonyl}-5-methoxy-1-[3-(trifluoromethyl)benzyl]tryptophan | 600 | 1.94 | 601 [M + H] |
| 57 | N-{[4-(but-2-ynyloxy)phenyl]sulfonyl}-5-methoxy-1-[4-(trifluoromethyl)benzyl]tryptophan | 600 | 1.96 | 601 [M + H] |
| 58 | N-{[4-(but-2-ynyloxy)phenyl]sulfonyl}-1-(2-fluorobenzyl)-5-methoxytryptophan | 550 | 1.86 | 551 [M + H] |
| 59 | N-{[4-(but-2-ynyloxy)phenyl]sulfonyl}-1-(3-fluorobenzyl)-5-methoxytryptophan | 550 | 1.86 | 551 [M + H] |
| 60 | N-{[4-(but-2-ynyloxy)phenyl]sulfonyl}-1-(4-fluorobenzyl)-5-methoxytryptophan | 550 | 1.86 | 551 [M + H] |
| 61 | N-{[4-(but-2-ynyloxy)phenyl]sulfonyl}-1-(3,5-difluorobenzyl)-5-methoxytryptophan | 568 | 1.88 | 569 [M + H] |
| 62 | N-{[4-(but-2-ynyloxy)phenyl]sulfonyl}-1-(4-chlorobenzyl)-5-methoxytryptophan | 567 | 1.92 | 568 [M + H] |
| 63 | N-{[4-(but-2-ynyloxy)phenyl]sulfonyl}-1-(4-isopropylbenzyl)-5-methoxytryptophan | 574 | 2.01 | 575 [M + H] |
| 64 | N-{[4-(but-2-ynyloxy)phenyl]sulfonyl}-1-(2-cyanobenzyl)-5-methoxytryptophan | 557 | 1.81 | 558 [M + H] |
| 65 | 1-(1,3-benzodioxol-5-ylmethyl)-N-{[4-(but-2-ynyloxy)phenyl]sulfonyl}-5-methoxytryptophan | 577 | 1.68 | 578 [M + H] |
| 66 | N-{[4-(but-2-ynyloxy)phenyl]sulfonyl}-5-methoxy-1-(pyridin-3-ylmethyl)tryptophan | 534 | 1.84 | 535 [M + H] |
| 67 | N-{[4-(but-2-ynyloxy)phenyl]sulfonyl}-1-isobutyl-5-methoxytryptophan | 499 | 1.87 | 500 [M + H] |
| 68 | N-{[4-(but-2-ynyloxy)phenyl]sulfonyl}-5-methoxy-1-pentyltryptophan | 513 | 1.98 | 514 [M + H] |
| 69 | N-{[4-(but-2-ynyloxy)phenyl]sulfonyl}-1-(cyclobutylmethyl)-5-methoxytryptophan | 511 | 1.92 | 512 [M + H] |
| 70 | N-{[4-(but-2-ynyloxy)phenyl]sulfonyl}-1-(cyclohexylmethyl)-5-methoxytryptophan | 539 | 1.98 | 540 [M + H] |

-continued

| Example | Compound Name | Calculated MW | LCMS Retention Time (min) | Observed MW |
|---|---|---|---|---|
| 71 | 1-benzyl-N-{[4-(but-2-ynyloxy)phenyl]sulfonyl}-5-chlorotryptophan | 537 | 1.97 | 538 [M + H] |
| 72 | N-{[4-(but-2-ynyloxy)phenyl]sulfonyl}-5-chloro-1-(2-methylbenzyl)tryptophan | 551 | 1.95 | 552 [M + H] |
| 73 | N-{[4-(but-2-ynyloxy)phenyl]sulfonyl}-5-chloro-1-(3-methylbenzyl)tryptophan | 551 | 1.93 | 552 [M + H] |
| 74 | N-{[4-(but-2-ynyloxy)phenyl]sulfonyl}-5-chloro-1-(2-methoxybenzyl)tryptophan | 567 | 1.93 | 568 [M + H] |
| 75 | N-{[4-(but-2-ynyloxy)phenyl]sulfonyl}-5-chloro-1-(3-methoxybenzyl)tryptophan | 567 | 2.03 | 568 [M + H] |
| 76 | N-{[4-(but-2-ynyloxy)phenyl]sulfonyl}-5-chloro-1-(4-methoxybenzyl)tryptophan | 567 | 3.05 | 568 [M + H] |
| 77 | N-{[4-(but-2-ynyloxy)phenyl]sulfonyl}-5-chloro-1-[4-(trifluoromethyl)benzyl]tryptophan | 605 | 3.27 | 606 [M + H] |
| 78 | N-{[4-(but-2-ynyloxy)phenyl]sulfonyl}-5-chloro-1-[4-(trifluoromethoxy)benzyl]tryptophan | 621 | 1.90 | 622 [M + H] |
| 79 | N-{[4-(but-2-ynyloxy)phenyl]sulfonyl}-5-chloro-1-(2-fluorobenzyl)tryptophan | 555 | 1.90 | 556 [M + H] |
| 80 | N-{[4-(but-2-ynyloxy)phenyl]sulfonyl}-5-chloro-1-(3-fluorobenzyl)tryptophan | 555 | 2.41 | 556 [M + H] |
| 81 | N-{[4-(but-2-ynyloxy)phenyl]sulfonyl}-5-chloro-1-(4-chlorobenzyl)tryptophan | 571 | 2.00 | 572 [M + H] |
| 82 | N-{[4-(but-2-ynyloxy)phenyl]sulfonyl}-5-chloro-1-(4-isopropylbenzyl)tryptophan | 579 | 3.42 | 580 [M + H] |
| 83 | 1-(1,3-benzodioxol-5-ylmethyl)-N-{[4-(but-2-ynyloxy)phenyl]sulfonyl}-5-chlorotryptophan | 581 | 1.83 | 582 [M + H] |
| 84 | N-{[4-(but-2-ynyloxy)phenyl]sulfonyl}-5-chloro-1-(pyridin-3-ylmethyl)tryptophan | 538 | 1.79 | 539 [M + H] |
| 85 | N-{[4-(but-2-ynyloxy)phenyl]sulfonyl}-5-chloro-1-isobutyltryptophan | 503 | 1.93 | 504 [M + H] |
| 86 | N-{[4-(but-2-ynyloxy)phenyl]sulfonyl}-5-chloro-1-(cyclobutylmethyl)tryptophan | 515 | 1.95 | 516 [M + H] |
| 87 | N-{[4-(but-2-ynyloxy)phenyl]sulfonyl}-5-chloro-1-(cyclohexylmethyl)tryptophan | 543 | 2.05 | 544 [M + H] |
| 88 | 1-benzyl-N-{[4-(but-2-ynyloxy)phenyl]sulfonyl}-5-chloro-2-methyltryptophan | 551 | 3.32 | 552 [M + H] |
| 89 | N-{[4-(but-2-ynyloxy)phenyl]sulfonyl}-5-chloro-1-(2-methoxybenzyl)-2-methyltryptophan | 581 | 3.37 | 582 [M + H] |
| 90 | N-{[4-(but-2-ynyloxy)phenyl]sulfonyl}-5-chloro-1-(3-methoxybenzyl)-2-methyltryptophan | 581 | 3.32 | 582 [M + H] |
| 91 | N-{[4-(but-2-ynyloxy)phenyl]sulfonyl}-5-chloro-1-(4-methoxybenzyl)-2-methyltryptophan | 581 | 3.31 | 582 [M + H] |
| 92 | N-{[4-(but-2-ynyloxy)phenyl]sulfonyl}-5-chloro-2-methyl-1-(4-methylbenzyl)tryptophan | 565 | 3.43 | 566 [M + H] |

-continued

| Example | Compound Name | Calculated MW | LCMS Retention Time (min) | Observed MW |
|---|---|---|---|---|
| 93 | N-{[4-(but-2-ynyloxy)phenyl]sulfonyl}-5-chloro-2-methyl-1-[4-(trifluoromethyl)benzyl]tryptophan | 619 | 3.50 | 620 [M + H] |
| 94 | N-{[4-(but-2-ynyloxy)phenyl]sulfonyl}-5-chloro-2-methyl-1-[4-(trifluoromethoxy)benzyl]tryptophan | 635 | 3.54 | 636 [M + H] |
| 95 | N-{[4-(but-2-ynyloxy)phenyl]sulfonyl}-5-chloro-1-(4-fluorobenzyl)-2-methyltryptophan | 569 | 3.32 | 570 [M + H] |
| 96 | N-{[4-(but-2-ynyloxy)phenyl]sulfonyl}-5-chloro-1-(4-chlorobenzyl)-2-methyltryptophan | 586 | 3.45 | 587 [M + H] |
| 97 | N-{[4-(but-2-ynyloxy)phenyl]sulfonyl}-5-chloro-1-(4-isopropylbenzyl)-2-methyltryptophan | 593 | 3.65 | 594 [M + H] |
| 98 | N-{[4-(but-2-ynyloxy)phenyl]sulfonyl}-5-chloro-1-(4-cyanobenzyl)-2-methyltryptophan | 576 | 3.17 | 577 [M + H] |
| 99 | N-{[4-(but-2-ynyloxy)phenyl]sulfonyl}-5-chloro-2-methyl-1-(pyridin-3-ylmethyl)tryptophan | 552 | 2.61 | 553 [M + H] |
| 100 | 1-(1,3-benzodioxol-5-ylmethyl)-N-{[4-(but-2-ynyloxy)phenyl]sulfonyl}-5-chloro-2-methyltryptophan | 595 | 3.24 | 596 [M + H] |
| 101 | N-{[4-(but-2-ynyloxy)phenyl]sulfonyl}-5-chloro-1-isobutyl-2-methyltryptophan | 517 | 3.32 | 518 [M + H] |
| 102 | N-{[4-(but-2-ynyloxy)phenyl]sulfonyl}-5-chloro-1-(cyclohexylmethyl)-2-methyltryptophan | 557 | 3.63 | 558 [M + H] |
| 103 | 1-benzyl-N-{[4-(but-2-ynyloxy)phenyl]sulfonyl}-5-carboxytryptophan | 547 | 2.71 | 546 [M − H] |
| 104 | N-{[4-(but-2-ynyloxy)phenyl]sulfonyl}-5-carboxy-1-(2-methylbenzyl)tryptophan | 561 | 2.84 | 560 [M − H] |
| 105 | N-{[4-(but-2-ynyloxy)phenyl]sulfonyl}-5-carboxy-1-(3-methylbenzyl)tryptophan | 561 | 2.84 | 560 [M − H] |
| 106 | N-{[4-(but-2-ynyloxy)phenyl]sulfonyl}-5-carboxy-1-(4-methylbenzyl)tryptophan | 561 | 2.83 | 560 [M − H] |
| 107 | N-{[(4-(but-2-ynyloxy)phenyl]sulfonyl}-5-carboxy-1-(2-methoxybenzyl)tryptophan | 577 | 2.85 | 576 [M − H] |
| 108 | N-{[4-(but-2-ynyloxy)phenyl]sulfonyl}-5-carboxy-1-(3-methoxybenzyl)tryptophan | 577 | 2.67 | 576 [M − H] |
| 109 | N-{[4-(but-2-ynyloxy)phenyl]sulfonyl}-5-carboxy-1-(4-methoxybenzyl)tryptophan | 577 | 2.78 | 576 [M − H] |
| 110 | N-{[4-(but-2-ynyloxy)phenyl]sulfonyl}-5-carboxy-1-(3,5-dimethoxybenzyl)tryptophan | 607 | 2.78 | 608 [M + H] |
| 111 | N-{[4-(but-2-ynyloxy)phenyl]sulfonyl}-5-carboxy-1-[2-(trifluoromethyl)benzyl]tryptophan | 615 | 3.04 | 616 [M + H] |
| 112 | N-{[4-(but-2-ynyloxy)phenyl]sulfonyl}-5-carboxy-1-[3-(trifluoromethyl)benzyl]tryptophan | 615 | 2.93 | 616 [M + H] |
| 113 | N-{[4-(but-2-ynyloxy)phenyl]sulfonyl}-5-carboxy-1-[4-(trifluoromethyl)benzyl]tryptophan | 615 | 3.02 | 616 [M + H] |

-continued

| Example | Compound Name | Calculated MW | LCMS Retention Time (min) | Observed MW |
|---|---|---|---|---|
| 114 | N-{[4-(but-2-ynyloxy)phenyl]sulfonyl}-5-carboxy-1-[4-(trifluoromethoxy)benzyl]tryptophan | 631 | 3.05 | 632 [M + H] |
| 115 | N-{[4-(but-2-ynyloxy)phenyl]sulfonyl}-5-carboxy-1-(2-fluorobenzyl)tryptophan | 565 | 2.75 | 566 [M + H] |
| 116 | N-{[4-(but-2-ynyloxy)phenyl]sulfonyl}-5-carboxy-1-(3-fluorobenzyl)tryptophan | 565 | 2.80 | 566 [M + H] |
| 117 | N-{[4-(but-2-ynyloxy)phenyl]sulfonyl}-5-carboxy-1-(4-fluorobenzyl)tryptophan | 565 | 2.83 | 566 [M + H] |
| 118 | N-{[4-(but-2-ynyloxy)phenyl]sulfonyl}-5-carboxy-1-(3,5-difluorobenzyl)tryptophan | 583 | 2.73 | 584 [M + H] |
| 119 | N-{[4-(but-2-ynyloxy)phenyl]sulfonyl}-5-carboxy-1-(4-chlorobenzyl)tryptophan | 581 | 2.87 | 582 [M + H] |
| 120 | N-{[4-(but-2-ynyloxy)phenyl]sulfonyl}-5-carboxy-1-(4-isopropylbenzyl)tryptophan | 589 | 3.10 | 590 [M + H] |
| 121 | N-{[4-(but-2-ynyloxy)phenyl]sulfonyl}-5-carboxy-1-(2-cyanobenzyl)tryptophan | 572 | 2.38 | 571 [M − H] |
| 122 | N-{[4-(but-2-ynyloxy)phenyl]sulfonyl}-5-carboxy-1-(3-cyanobenzyl)tryptophan | 572 | 2.38 | 571 [M − H] |
| 123 | N-{[4-(but-2-ynyloxy)phenyl]sulfonyl}-5-carboxy-1-(4-cyanobenzyl)tryptophan | 572 | 2.38 | 571 [M − H] |
| 124 | 1-(1,3-benzodioxol-5-ylmethyl)-N-{[4-(but-2-ynyloxy)phenyl]sulfonyl}-5-carboxytryptophan | 591 | 2.77 | 590 [M − H] |
| 125 | N-{[4-(but-2-ynyloxy)phenyl]sulfonyl}-5-carboxy-1-(pyridin-3-ylmethyl)tryptophan | 548 | 1.89 | 549 [M + H] |
| 126 | N-{[4-(but-2-ynyloxy)phenyl]sulfonyl}-5-carboxy-1-(4-carboxybenzyl)tryptophan | 591 | 2.37 | 592 [M + H] |
| 127 | N-{[4-(but-2-ynyloxy)phenyl]sulfonyl}-5-carboxy-1-methyltryptophan | 471 | 2.25 | 470 [M − H] |
| 128 | N-{[4-(but-2-ynyloxy)phenyl]sulfonyl}-5-carboxy-1-ethyltryptophan | 485 | 2.38 | 484 [M − H] |
| 129 | N-{[4-(but-2-ynyloxy)phenyl]sulfonyl}-5-carboxy-1-isobutyltryptophan | 513 | 2.64 | 512 [M − H] |
| 130 | N-{[4-(but-2-ynyloxy)phenyl]sulfonyl}-5-carboxy-1-pentyltryptophan | 527 | 2.80 | 526 [M − H] |
| 131 | N-{[4-(but-2-ynyloxy)phenyl]sulfonyl}-5-carboxy-1-(cyclobutylmethyl)tryptophan | 525 | 2.60 | 524 [M − H] |
| 132 | N-{[4-(but-2-ynyloxy)phenyl]sulfonyl}-5-carboxy-1-(cyclohexylmethyl)tryptophan | 553 | 2.93 | 552 [M − H] |
| 133 | N-{[4-(but-2-ynyloxy)phenyl]sulfonyl}-5-chlorotryptophan | 447 | 1.69 | 448 [M + H] |
| 134 | N-{[4-(but-2-ynyloxy)phenyl]sulfonyl}-2-methyltryptophan | 426 | 1.62 | 427 [M + H] |
| 135 | 1-benzyl-N-{[4-(but-2-ynyloxy)phenyl]sulfonyl}-5-cyanotryptophan | 527 | 1.85 | 528 [M + H] |
| 136 | N-{[4-(but-2-ynyloxy)phenyl]sulfonyl}-5-cyano-1-(4-methylbenzyl)tryptophan | 541 | 2.94 | 542 [M + H] |
| 137 | N-{[4-(but-2-ynyloxy)phenyl]sulfonyl}-5-cyano-1-(2-methoxybenzyl)tryptophan | 557 | 1.91 | 558 [M + H] |

| Example | Compound Name | Calculated MW | LCMS Retention Time (min) | Observed MW |
|---|---|---|---|---|
| 138 | N-{[4-(but-2-ynyloxy)phenyl]sulfonyl}-5-cyano-1-(3-methoxybenzyl)tryptophan | 557 | 1.86 | 558 [M + H] |
| 139 | N-{[4-(but-2-ynyloxy)phenyl]sulfonyl}-5-cyano-1-(4-methoxybenzyl)tryptophan | 557 | 1.85 | 558 [M + H] |
| 140 | N-{[4-(but-2-ynyloxy)phenyl]sulfonyl}-5-cyano-1-[4-(trifluoromethoxy)benzyl]tryptophan | 611 | 1.98 | 612 [M + H] |
| 141 | N-{[4-(but-2-ynyloxy)phenyl]sulfonyl}-5-cyano-1-(4-fluorobenzyl)tryptophan | 545 | 1.86 | 546 [M + H] |
| 142 | N-{[4-(but-2-ynyloxy)phenyl]sulfonyl}-5-cyano-1-(4-isopropylbenzyl)tryptophan | 569 | 2.01 | 570 [M + H] |
| 143 | N-{[4-(but-2-ynyloxy)phenyl]sulfonyl}-5-cyano-1-isobutyltryptophan | 493 | 1.84 | 494 [M + H] |
| 144 | 1-benzyl-N-{[4-(but-2-ynyloxy)phenyl]sulfonyl}-2-methyltryptophan | 516 | 2.54 | 517 [M + H] |
| 145 | N-{[4-(but-2-ynyloxy)phenyl]sulfonyl}-2-methyl-1-(2-methylbenzyl)tryptophan | 530 | 2.57 | 531 [M + H] |
| 146 | N-{[4-(but-2-ynyloxy)phenyl]sulfonyl}-1-(2-methoxybenzyl)-2-methyltryptophan | 546 | 2.55 | 547 [M + H] |
| 147 | N-{[4-(but-2-ynyloxy)phenyl]sulfonyl}-1-(3-methoxybenzyl)-2-methyltryptophan | 546 | 2.53 | 547 [M + H] |
| 148 | N-{[4-(but-2-ynyloxy)phenyl]sulfonyl}-1-(4-methoxybenzyl)-2-methyltryptophan | 546 | 2.51 | 547 [M + H] |
| 149 | N-{[4-(but-2-ynyloxy)phenyl]sulfonyl}-2-methyl-1-[3-(trifluoromethyl)benzyl]tryptophan | 584 | 2.00 | 585 [M + H] |
| 150 | N-{[4-(but-2-ynyloxy)phenyl]sulfonyl}-2-methyl-1-[4-(trifluoromethyl)benzyl]tryptophan | 584 | 2.61 | 585 [M + H] |
| 151 | N-{[4-(but-2-ynyloxy)phenyl]sulfonyl}-2-methyl-1-[4-(trifluoromethoxy)benzyl]tryptophan | 600 | 2.64 | 601 [M + H] |
| 152 | N-{[4-(but-2-ynyloxy)phenyl]sulfonyl}-1-(2-fluorobenzyl)-2-methyltryptophan | 534 | 2.54 | 535 [M + H] |
| 153 | N-{[4-(but-2-ynyloxy)phenyl]sulfonyl}-1-(3-fluorobenzyl)-2-methyltryptophan | 534 | 2.53 | 535 [M + H] |
| 154 | N-{[4-(but-2-ynyloxy)phenyl]sulfonyl}-1-(4-fluorobenzyl)-2-methyltryptophan | 534 | 2.53 | 535 [M + H] |
| 155 | N-{[4-(but-2-ynyloxy)phenyl]sulfonyl}-1-(3,5-difluorobenzyl)-2-methyltryptophan | 552 | 2.55 | 553 [M + H] |
| 156 | N-{[4-(but-2-ynyloxy)phenyl]sulfonyl}-1-(4-chlorobenzyl)-2-methyltryptophan | 550 | 2.61 | 551 [M + H] |
| 157 | N-{[4-(but-2-ynyloxy)phenyl]sulfonyl}-1-(4-isopropylbenzyl)-2-methyltryptophan | 558 | 2.70 | 559 [M + H] |
| 158 | N-{[4-(but-2-ynyloxy)phenyl]sulfonyl}-1-(2-cyanobenzyl)-2-methyltryptophan | 541 | 2.23 | 542 [M + H] |
| 159 | N-{[4-(but-2-ynyloxy)phenyl]sulfonyl}-1-(3-cyanobenzyl)-2-methyltryptophan | 541 | 2.25 | 542 [M + H] |
| 160 | N-{[4-(but-2-ynyloxy)phenyl]sulfonyl}-1-(4-cyanobenzyl)-2-methyltryptophan | 541 | 2.23 | 542 [M + H] |

-continued

| Example | Compound Name | Calculated MW | LCMS Retention Time (min) | Observed MW |
|---|---|---|---|---|
| 161 | 1-(1,3-benzodioxol-5-ylmethyl)-N-{[4-(but-2-ynyloxy)phenyl]sulfonyl}-2-methyltryptophan | 560 | 2.49 | 561 [M + H] |
| 162 | N-{[4-(but-2-ynyloxy)phenyl]sulfonyl}-2-methyl-1-(pyridin-3-ylmethyl)tryptophan | 517 | 2.10 | 518 [M + H] |
| 163 | N-{[4-(but-2-ynyloxy)phenyl]sulfonyl}-1-ethyl-2-methyltryptophan | 454 | 2.40 | 455 [M + H] |
| 164 | N-{[4-(but-2-ynyloxy)phenyl]sulfonyl}-1-isobutyl-2-methyltryptophan | 482 | 2.53 | 483 [M + H] |
| 165 | N-{[4-(but-2-ynyloxy)phenyl]sulfonyl}-1-(cyclobutylmethyl)-2-methyltryptophan | 494 | 2.56 | 495 [M + H] |
| 166 | N-{[4-(but-2-ynyloxy)phenyl]sulfonyl}-1-(cyclohexylmethyl)-2-methyltryptophan | 522 | 3.34 | 523 [M + H] |
| 167 | 1-benzyl-N-{[4-(but-2-ynyloxy)phenyl]sulfonyl}-5-methyltryptophan | 516 | 2.54 | 517 [M + H] |
| 168 | N-{[4-(but-2-ynyloxy)phenyl]sulfonyl}-5-methyl-1-(2-methylbenzyl)tryptophan | 530 | 2.59 | 531 [M + H] |
| 169 | N-{[4-(but-2-ynyloxy)phenyl]sulfonyl}-5-methyl-1-(3-methylbenzyl)tryptophan | 530 | 3.18 | 531 [M + H] |
| 170 | N-{[4-(but-2-ynyloxy)phenyl]sulfonyl}-1-(2-methoxybenzyl)-5-methyltryptophan | 546 | 2.57 | 547 [M + H] |
| 171 | N-{[4-(but-2-ynyloxy)phenyl]sulfonyl}-1-(3-methoxybenzyl)-5-methyltryptophan | 546 | 2.54 | 547 [M + H] |
| 172 | N-{[4-(but-2-ynyloxy)phenyl]sulfonyl}-5-methyl-1-[2-(trifluoromethyl)benzyl]tryptophan | 584 | 2.65 | 585 [M + H] |
| 173 | N-{[4-(but-2-ynyloxy)phenyl]sulfonyl}-5-methyl-1-[3-(trifluoromethyl)benzyl]tryptophan | 584 | 2.61 | 585 [M + H] |
| 174 | N-{[4-(but-2-ynyloxy)phenyl]sulfonyl}-5-methyl-1-[4-(trifluoromethyl)benzyl]tryptophan | 584 | 2.62 | 585 [M + H] |
| 175 | N-{[4-(but-2-ynyloxy)phenyl]sulfonyl}-1-(3-fluorobenzyl)-5-methyltryptophan | 534 | 2.55 | 535 [M + H] |
| 176 | N-{[4-(but-2-ynyloxy)phenyl]sulfonyl}-1-(4-fluorobenzyl)-5-methyltryptophan | 534 | 2.55 | 535 [M + H] |
| 177 | N-{[4-(but-2-ynyloxy)phenyl]sulfonyl}-1-(3,5-difluorobenzyl)-5-methyltryptophan | 552 | 2.56 | 553 [M + H] |
| 178 | N-{[4-(but-2-ynyloxy)phenyl]sulfonyl}-1-(4-chlorobenzyl)-5-methyltryptophan | 551 | 2.61 | 552 [M + H] |
| 179 | N-{[4-(but-2-ynyloxy)phenyl]sulfonyl}-1-(4-isopropylbenzyl)-5-methyltryptophan | 558 | 2.71 | 559 [M + H] |
| 180 | 1-(1,3-benzodioxol-5-ylmethyl)-N-{[4-(but-2-ynyloxy)phenyl]sulfonyl}-5-methyltryptophan | 560 | 2.51 | 561 [M + H] |
| 181 | N-{[4-(but-2-ynyloxy)phenyl]sulfonyl}-5-methyl-1-(pyridin-3-ylmethyl)tryptophan | 517 | 2.15 | 518 [M + H] |
| 182 | N-{[4-(but-2-ynyloxy)phenyl]sulfonyl}-1-ethyl-5-methyltryptophan | 454 | 2.82 | 455 [M + H] |

-continued

| Example | Compound Name | Calculated MW | LCMS Retention Time (min) | Observed MW |
|---|---|---|---|---|
| 183 | N-{[4-(but-2-ynyloxy)phenyl]sulfonyl}-1-isobutyl-5-methyltryptophan | 482 | 2.56 | 483 [M + H] |
| 184 | N-{[4-(but-2-ynyloxy)phenyl]sulfonyl}-5-methyl-1-pentyltryptophan | 496 | 2.64 | 497 [M + H] |
| 185 | 1-benzyl-N-{[4-(but-2-ynyloxy)phenyl]sulfonyl}-5-methoxy-2-methyltryptophan | 547 | 3.13 | 548 [M + H] |
| 186 | N-{[4-(but-2-ynyloxy)phenyl]sulfonyl}-5-methoxy-2-methyl-1-(2-methylbenzyl)tryptophan | 561 | 3.23 | 562 [M + H] |
| 187 | N-{[4-(but-2-ynyloxy)phenyl]sulfonyl}-5-methoxy-2-methyl-1-(3-methylbenzyl)tryptophan | 561 | 3.24 | 562 [M + H] |
| 188 | N-{[4-(but-2-ynyloxy)phenyl]sulfonyl}-5-methoxy-2-methyl-1-(4-methylbenzyl)tryptophan | 561 | 3.25 | 562 [M + H] |
| 189 | N-{[4-(but-2-ynyloxy)phenyl]sulfonyl}-5-methoxy-1-(2-methoxybenzyl)-2-methyltryptophan | 577 | 3.18 | 578 [M + H] |
| 190 | N-{[4-(but-2-ynyloxy)phenyl]sulfonyl}-5-methoxy-1-(3-methoxybenzyl)-2-methyltryptophan | 577 | 3.11 | 578 [M + H] |
| 191 | N-{[4-(but-2-ynyloxy)phenyl]sulfonyl}-5-methoxy-1-(4-methoxybenzyl)-2-methyltryptophan | 577 | 3.10 | 578 [M + H] |
| 192 | N-{[4-(but-2-ynyloxy)phenyl]sulfonyl}-1-(3,5-dimethoxybenzyl)-5-methoxy-2-methyltryptophan | 607 | 3.11 | 608 [M + H] |
| 193 | N-{[4-(but-2-ynyloxy)phenyl]sulfonyl}-5-methoxy-2-methyl-1-[2-(trifluoromethyl)benzyl]tryptophan | 615 | 3.38 | 616 [M + H] |
| 194 | N-{[4-(but-2-ynyloxy)phenyl]sulfonyl}-5-methoxy-2-methyl-1-[3-(trifluoromethoxy)benzyl]tryptophan | 631 | 3.37 | 632 [M + H] |
| 195 | N-{[4-(but-2-ynyloxy)phenyl]sulfonyl}-5-methoxy-2-methyl-1-[4-(trifluoromethyl)benzyl]tryptophan | 615 | 3.33 | 616 [M + H] |
| 196 | N-{[4-(but-2-ynyloxy)phenyl]sulfonyl}-5-methoxy-2-methyl-1-[4-(trifluoromethoxy)benzyl]tryptophan | 631 | 3.40 | 632 [M + H] |
| 197 | N-{[4-(but-2-ynyloxy)phenyl]sulfonyl}-1-(2-fluorobenzyl)-5-methoxy-2-methyltryptophan | 565 | 3.16 | 566 [M + H] |
| 198 | N-{[4-(but-2-ynyloxy)phenyl]sulfonyl}-1-(3-fluorobenzyl)-5-methoxy-2-methyltryptophan | 565 | 3.14 | 566 [M + H] |
| 199 | N-{[4-(but-2-ynyloxy)phenyl]sulfonyl}-1-(4-fluorobenzyl)-5-methoxy-2-methyltryptophan | 565 | 3.15 | 566 [M + H] |
| 200 | N-{[4-(but-2-ynyloxy)phenyl]sulfonyl}-1-(3,5-difluorobenzyl)-5-methoxy-2-methyltryptophan | 583 | 3.10 | 584 [M + H] |
| 201 | N-{[4-(but-2-ynyloxy)phenyl]sulfonyl}-1-(4-chlorobenzyl)-5-methoxy-2-methyltryptophan | 581 | 3.19 | 582 [M + H] |

-continued

| Example | Compound Name | Calculated MW | LCMS Retention Time (min) | Observed MW |
|---------|---------------|---------------|---------------------------|-------------|
| 202 | N-{[4-(but-2-ynyloxy)phenyl]sulfonyl}-1-(4-isopropylbenzyl)-5-methoxy-2-methyltryptophan | 589 | 3.39 | 590 [M + H] |
| 203 | N-{[4-(but-2-ynyloxy)phenyl]sulfonyl}-1-(2-cyanobenzyl)-5-methoxy-2-methyltryptophan | 572 | 2.93 | 573 [M + H] |
| 204 | N-{[4-(but-2-ynyloxy)phenyl]sulfonyl}-1-(3-cyanobenzyl)-5-methoxy-2-methyltryptophan | 572 | 2.88 | 573 [M + H] |
| 205 | N-{[4-(but-2-ynyloxy)phenyl]sulfonyl}-1-(4-cyanobenzyl)-5-methoxy-2-methyltryptophan | 572 | 2.88 | 573 [M + H] |
| 206 | 1-(1,3-benzodioxol-5-ylmethyl)-N-{[4-(but-2-ynyloxy)phenyl]sulfonyl}-5-methoxy-2-methyltryptophan | 591 | 3.05 | 592 [M + H] |
| 207 | N-{[4-(but-2-ynyloxy)phenyl]sulfonyl}-1-(4-carboxybenzyl)-5-methoxy-2-methyltryptophan | 591 | 2.64 | 592 [M + H] |
| 208 | N-{[4-(but-2-ynyloxy)phenyl]sulfonyl}-5-methoxy-1,2-dimethyltryptophan | 471 | 2.66 | 472 [M + H] |
| 209 | N-{[4-(but-2-ynyloxy)phenyl]sulfonyl}-1-ethyl-5-methoxy-2-methyltryptophan | 485 | 2.76 | 486 [M + H] |
| 210 | N-{[4-(but-2-ynyloxy)phenyl]sulfonyl}-1-isobutyl-5-methoxy-2-methyltryptophan | 513 | 3.04 | 514 [M + H] |
| 211 | N-{[4-(but-2-ynyloxy)phenyl]sulfonyl}-5-methoxy-2-methyl-1-pentyltryptophan | 527 | 3.21 | 528 [M + H] |
| 212 | N-{[4-(but-2-ynyloxy)phenyl]sulfonyl}-1-(cyclobutylmethyl)-5-methoxy-2-methyltryptophan | 525 | 3.10 | 526 [M + H] |
| 213 | N-{[4-(but-2-ynyloxy)phenyl]sulfonyl}-1-(cyclohexylmethyl)-5-methoxy-2-methyltryptophan | 553 | 3.34 | 554 [M + H] |
| 214 | N-{[4-(but-2-ynyloxy)phenyl]sulfonyl}-1-(4-hydroxybenzyl)-D-tryptophan | 518 | 2.38 | 517 [M − H] |
| 215 | N-{[4-(but-2-ynyloxy)phenyl]sulfonyl}-1-(4-ethoxybenzyl)-D-tryptophan | 546 | 2.54 | 547 [M + H] |
| 216 | 1-[4-(allyloxy)benzyl]-N-{[4-(but-2-ynyloxy)phenyl]sulfonyl}-D-tryptophan | 558 | 3.08 | 559 [M + H] |
| 217 | N-{[4-(but-2-ynyloxy)phenyl]sulfonyl}-5-methyl-D(or L)-tryptophan | 426 | 2.69 | 427 [M + H] |
| 218 | N-{[4-(but-2-ynyloxy)phenyl]sulfonyl}-5-methyl-L(or D)-tryptophan | 426 | 2.69 | 427 [M + H] |
| 219 | 1-(tert-butoxycarbonyl)-N-{[4-(but-2-ynyloxy)phenyl]sulfonyl}-L-tryptophan | 513 | 3.05 | 512 [M − H] |
| 220 | 1-(tert-butoxycarbonyl)-N-{[4-(but-2-ynyloxy)phenyl]sulfonyl}-D-tryptophan | 513 | 3.06 | 512 [M − H] |
| 221 | N-{[4-(but-2-ynyloxy)phenyl]sulfonyl}-5-methoxy-D(or L)-tryptophan | 442 | 2.50 | 443 [M + H] |
| 222 | N-{[4-(but-2-ynyloxy)phenyl]sulfonyl}-methoxy-L(or D)-tryptophan | 442 | 2.51 | 443 [M + H] |
| 223 | 5-(benzyloxy)-N-{[4-(but-2-ynyloxy)phenyl]sulfonyl}-D(or L)-tryptophan | 519 | 2.99 | 520 [M + H] |

-continued

| Example | Compound Name | Calculated MW | LCMS Retention Time (min) | Observed MW |
|---|---|---|---|---|
| 224 | 5-(benzyloxy)-N-{[4-(but-2-ynyloxy)phenyl]sulfonyl}-L(or D)-tryptophan | 519 | 2.98 | 520 [M + H] |

Exemplary Syntheses of Compounds of the Invention

Procedures for the preparation of compounds of Examples 4, 6, 20, 32, 39, 46 and 47 are shown below.

Preparation of Compound of Example 6

2-(4-BUT-2-YNYLOXY-BENZENESULFONY-LAMINO)-3-(5-METHYL-1H-INDOL-3-YL)-PROPIONIC Acid

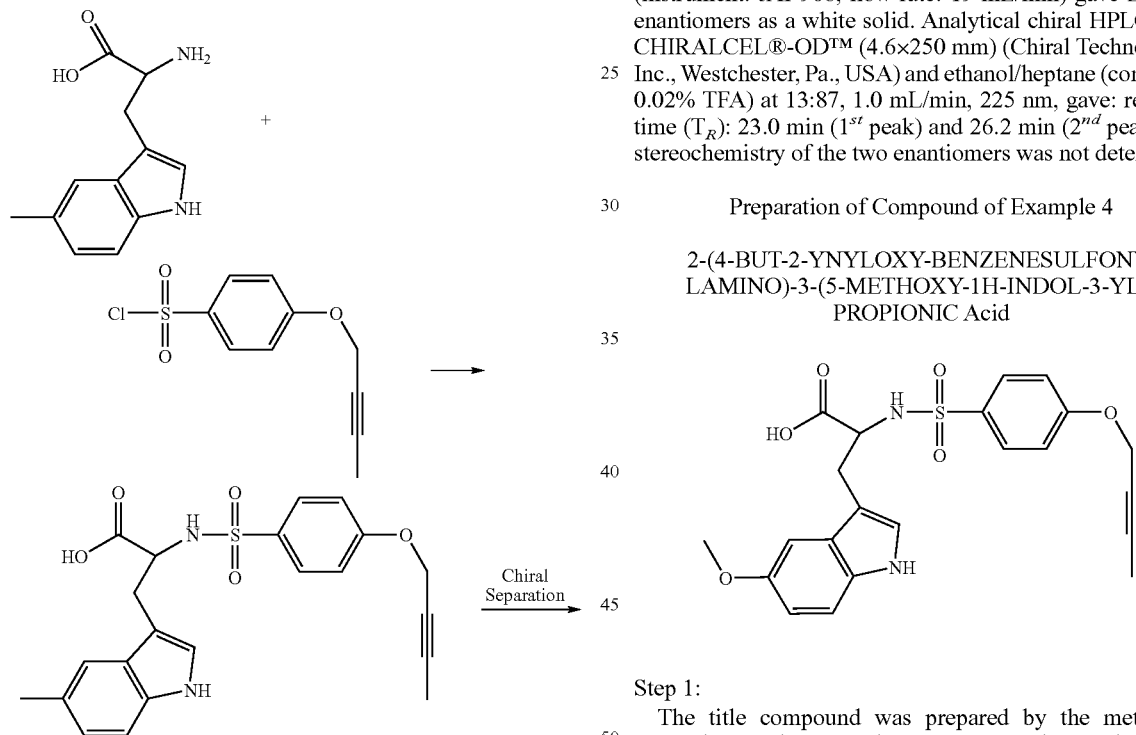

Step 1:

Triethylamine (0.38 mL, 2.75 mmol) was added to a solution of 5-methyl-DL-tryptophan (0.20 g, 0.92 mmol) and 4-but-2-ynyloxy-benzenesulfonyl chloride (0.25 g, 1.01 mmol) in $H_2O$-dioxane (1.6 mL/2.4 mL) at room temperature. The reaction mixture was stirred for 20 hours at room temperature. The mixture was then concentrated and acidified with HCl. The mixture was extracted with ethyl acetate (3×10 mL). The organic solution was washed with $H_2O$ and brine, dried over $Na_2SO_4$, and concentrated. The residue was purified by RP-HPLC to give 0.32 g (81%) of the title compound as a pale yellow solid. Mp=45-46° C.; $^1$H NMR (DMSO-$d_6$): 400 MHz δ 12.54 (bs, 1H), 10.64 (s, 1H), 8.05 (d, J=8.0 Hz, 1H), 7.53 (m, 2H), 7.17 (d, J=8.0 Hz, 1H), 7.00 (m, 2H), 6.95 (m, 2H), 6.86 (dd J=8.0, 4.0 Hz, 1H), 4.78 (q, J=2.4 Hz, 2H), 3.81 (q, J=7.6 Hz, 1H), 3.00 (dd J=14.4, 6.8 Hz, 1H), 2.79 (dd J=14.4, 7.8 Hz, 1H), 2.33 (s, 3H), 1.82 (t, J=2.4 Hz, 3H); HRMS: calcd for $C_{22}H_{23}N_2O_5S$ (ESI+, [M+H]$^{1+}$), 427.1322; found 427.1327; LCMS m/z (ESI) [M+H]$^{1+}$ 427, retention time=2.69 min.

Step 2: Chiral Separation

Preparative HPLC using CHIRALPAK®-OD™ (20×250 mm) (Chiral Technologies, Inc., Westchester, Pa., USA) and 15% isopropyl alcohol in heptane (0.02% TFA) as eluant (instrument: JAI-908, flow rate: 19 mL/min) gave D and L enantiomers as a white solid. Analytical chiral HPLC using CHIRALCEL®-OD™ (4.6×250 mm) (Chiral Technologies, Inc., Westchester, Pa., USA) and ethanol/heptane (containing 0.02% TFA) at 13:87, 1.0 mL/min, 225 nm, gave: retention time ($T_R$): 23.0 min (1$^{st}$ peak) and 26.2 min (2$^{nd}$ peak). The stereochemistry of the two enantiomers was not determined.

Preparation of Compound of Example 4

2-(4-BUT-2-YNYLOXY-BENZENESULFONY-LAMINO)-3-(5-METHOXY-1H-INDOL-3-YL)-PROPIONIC Acid

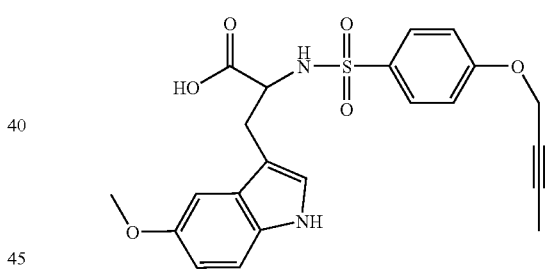

Step 1:

The title compound was prepared by the method of Example 6, using 5-methoxy-DL-tryptophan and 4-but-2-ynyloxy-benzenesulfonyl chloride as starting materials. $^1$H NMR (DMSO-$d_6$): 400 MHz δ 12.55 (bs, 1H), 10.63 (s, 1H), 8.06 (d, J=8.0 Hz, 1H), 7.53 (dd, J=8.0, 4.0 Hz, 2H), 7.18 (d, J=8.0 Hz, 1H), 7.02 (d, J=2.0 Hz, 1H), 6.92 (d, J=8.0 Hz, 2H), 6.82 (d, J=2.0 Hz, 1H), 6.68 (dd, J=8.0, 2.0 Hz, 1H), 4.78 (q, J=2.0 Hz, 2H), 3.87 (q, J=7.6 Hz, 1H), 3.72 (s, 3H), 3.00 (dd J=14.4, 6.4 Hz, 1H), 2.82 (dd J=14.4, 7.6 Hz, 1H), 1.83 (t, J=2.0 Hz, 3H); HRMS: calcd for $C_{22}H_{24}N_2O_6S$ (ESI+, [M+H]$^{1+}$), 443.1271; found 443.1265; LCMS m/z (ESI) [M+H] 443, retention time=2.50 min.

Step 2: Chiral Separation

Preparative HPLC using CHIRALPAK®-OJ™ (20×250 mm) (Chiral Technologies, Inc., Westchester, Pa., USA) and 15% ethanol in heptane (0.1% TFA) as eluant (flow rate: 7 mL/min) gave D and L enantiomers as a white solid. Analytical chiral HPLC using CHIRALCEL®-OJ™ (4.6×250 mm)

(Chiral Technologies, Inc., Westchester, Pa., USA) and ethanol/heptane (containing 0.02% TFA) at 85:15, 1.0 mL/min, 215 nm, gave: retention time ($T_R$): 4.86 min (1st peak) and 6.32 min (2nd peak). The stereochemistry of the two enantiomers was not determined.

Preparation of Compound of Example 20

2-(4-BUT-2-YNYLOXY-BENZENESULFONY-LAMINO)-3-(5-BENZYLOXY-1H-INDOL-3-YL)-PROPIONIC Acid

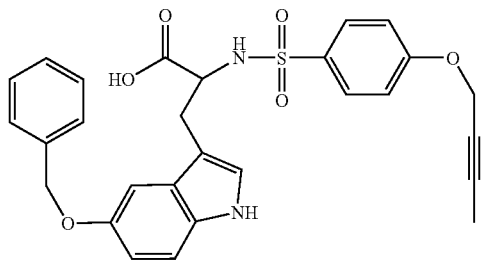

Step 1:

The title compound was prepared by the method of Example 6, using 5-benzyloxy-DL-tryptophan and 4-but-2-ynyloxy-benzenesulfonyl chloride as starting materials. $^1$H NMR (DMSO-$d_6$): 400 MHz δ 12.55 (bs, 1H), 10.64 (s, 1H), 8.05 (d, J=8.0 Hz, 1H), 7.50-7.33 (m, 7H), 7.19 (d, J=12.0 Hz, 1H), 7.03 (d, J=4.0 Hz, 1H), 6.97 (d, J=4.0 Hz, 1H), 6.87 (d, J=8.0 Hz, 2H), 6.76 (dd, J=8.0, 4.0 Hz, 1H), 5.04 (s, 2H), 4.74 (q, J=2.4 Hz, 2H), 3.86 (q, J=8.0 Hz, 1H), 3.00 (dd J=14.4, 6.4 Hz, 1H), 2.83 (dd J=14.4, 8.0 Hz, 1H), 1.82 (t, J=2.4 Hz, 3H); HRMS: calcd for $C_{28}H_{27}N_2O_6S$ (ESI+, [M+H]$^{1+}$), 519.1584; found 519.1588; LCMS m/z (ESI) [M+H] 519, retention time=2.99 min.

Step 2: Chiral Separation

Preparative HPLC using CHIRALPAK®-OJ™ (20×250 mm) (Chiral Technologies, Inc., Westchester, Pa., USA) and 15% ethanol in heptane (0.1% TFA) as eluant (flow rate: 13 mL/min) gave D and L enantiomers as a white solid. Analytical chiral HPLC using CHIRALCEL®-OJ™ (4.6×250 mm) (Chiral Technologies, Inc., Westchester, Pa., USA) and ethanol/heptane (containing 0.02% TFA) at 85:15, 1.0 mL/min, 215 nm, gave: retention time ($T_R$): 6.76 min (1st peak) and 13.1 min (2nd peak). The stereochemistry of the two enantiomers was not determined.

Preparation of Compound of Example 32

2-(4-BUT-2-YNYLOXY-BENZENESULFONY-LAMINO)-3-(1-CYCLOBUTYLMETHYL-1H-INDOL-3-YL)-PROPIONIC Acid

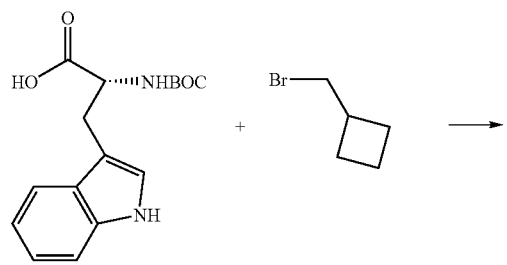

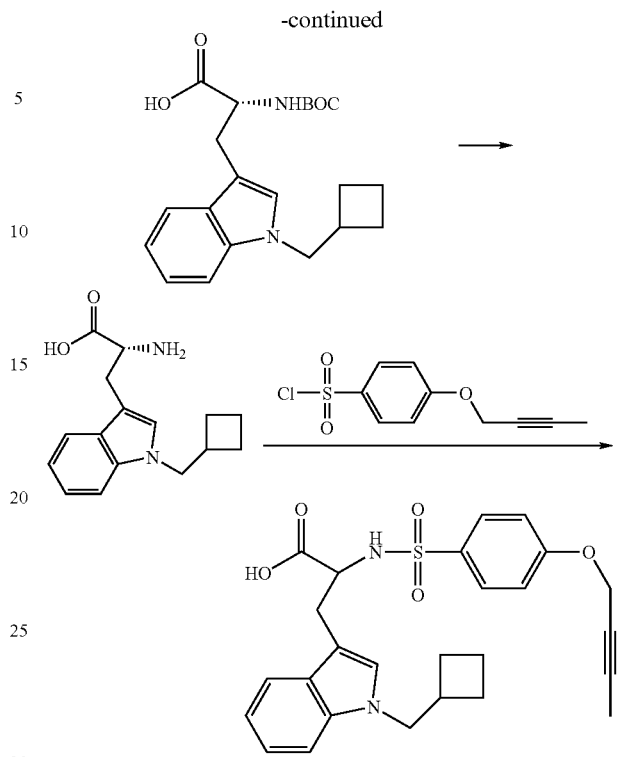

Step 1: Synthesis of N-(tert-butoxycarbonyl)-1-cyclobutylmethyl-D-tryptophan

In a 20 mL vial, NaH (60% in mineral oil) (0.092 g, 2.30 mmol) was added to a solution of N-(tert-butoxycarbonyl)-D-tryptophan (0.200 g, 0.657 mmol) in anhydrous N,N-dimethylformamide (4 mL) at 0° C. The reaction mixture was placed in a shaker for 20 min. at 0° C. (Bromomethyl)cyclobutane (0.074 mL, 0.657 mmol) was added to the solution and allowed to react for 10 hours at 0° C. The reaction mixture was quenched with $H_2O$ and acidified with 1M NaHSO$_4$ until pH=3. The solution was extracted with $CH_2Cl_2$, washed with brine, dried over Na$_2$SO$_4$, and concentrated to give the title compound.

Step 2: Synthesis of 1-cyclobutylmethyl-D-tryptophan

The dried crude product of Step 1 was dissolved in $CH_2Cl_2$-TFA (1 mL/1 mL) and the solution was shaken for 10 hours at room temperature. The solution was concentrated and the resulting product was dissolved in $CH_2Cl_2$. The solution was washed with $H_2O$ and brine, dried over Na$_2$SO$_4$, and concentrated to give the title compound.

Step 3: Synthesis of 2-(4-but-2-ynyloxy-benzene-sulfonylamino)-3-(1-cyclobutylmethyl-1H-indol-3-yl)-propionic Acid Triethylamine (0.275 mL, 1.97 mmol) was added to a solution of crude 1-cyclobutylmethyl-D-tryptophan of Step 2 (0.657 mmol) and 4-but-2-ynyloxy-benzenesulfonyl chloride (0.177 g, 0.723 mmol) in $H_2O$-dioxane (2 mL:3 mL) at room temperature. The reaction mixture was stirred for 20 hours at room temperature. The mixture was then concentrated and acidified with HCl. The mixture was extracted with ethyl acetate (3×10 mL). The organic solution was washed with H₂O and brine, dried over Na₂SO₄, and concentrated. The residue was purified by RP-HPLC to give 0.152 g (48% in 3 steps) of the title compound as a yellow solid. $^1$H NMR (DMSO-d$_6$): 400 MHz δ 12.57 (bs, 1H), 8.07 (d, J=8.4 Hz, 1H), 7.49 (d, J=7.2 Hz, 2H), 7.37 (d, J=8.0 Hz, 1H), 7.29 (d, J=7.6 Hz, 1H), 7.08 (t, J=7.4 Hz, 1H), 7.02 (s, 1H), 6.96-6.88 (m, 3H), 4.77 (q, J=2.4 Hz, 2H), 4.04 (d, J=6.8 Hz, 2H), 3.84 (q, J=6.8 Hz, 1H), 3.02 (dd J=14.4, 6.4 Hz, 1H), 2.82 (dd J=14.4, 8.4 Hz, 1H), 2.67 (p, J=7.6 Hz, 1H), 1.91 (m, 2H), 1.83 (m, 5H), 1.75 (m, 2H); HRMS: calcd for C$_{26}$H$_{29}$N$_2$O$_5$S (ESI+, [M+H]$^{1+}$), 481.1792; found 481.1786; LCMS m/z (ESI) [M+H] 481, retention time=3.22 min.

Preparation of Compound of Example 39

2-(4-BUT-2-YNYLOXY-BENZENESULFONY-LAMINO)-3-[1-(2-TRIFLUOROMETHYLBEN-ZYL)-1H-INDOL-3-YL]-PROPIONIC Acid

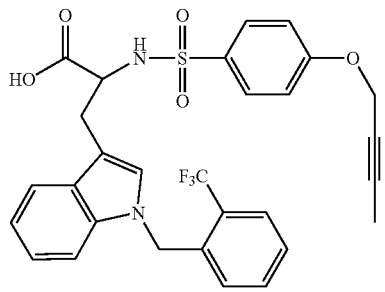

The title compound was prepared by the method of Example 32, using N-(tert-butoxycarbonyl)-D-tryptophan and 2-(trifluoromethyl)benzyl bromide as starting materials. $^1$H NMR (DMSO-d$_6$): 400 MHz δ 12.57 (bs, 1H), 8.13 (d, J=8.4 Hz, 1H), 7.78 (d, J=6.8 Hz, 1H), 7.57 (d, J=8.8 Hz, 2H), 7.43 (m, 2H), 7.37 (d, J=7.6 Hz, 1H), 7.19 (s, 1H), 7.12-6.99 (m, 3H), 6.93 (d, J=8.8 Hz, 2H), 6.44 (d, J=6.4 Hz, 1H), 5.51 (s, 2H), 4.77 (q, J=2.0 Hz, 2H), 3.91 (q, J=7.6 Hz, 1H), 3.08 (dd J=14.4, 7.2 Hz, 1H), 2.88 (dd J=14.4, 7.6 Hz, 1H), 1.82 (t, J=2.4 Hz, 3H); HRMS: calcd for C$_{29}$H$_{26}$F$_3$N$_2$O$_5$S (ESI+, [M+H]$^{1+}$), 571.1509; found 571.1505; LCMS m/z (ESI) [M+H] 571, retention time=3.37 min.

Preparation of Compound of Example 46

3-(5-BROMO-1H-INDOL-3-YL)-2-(4-BUT-2-YNY-LOXY-BENZENESULFONYLAMINO)-PROPI-ONIC Acid

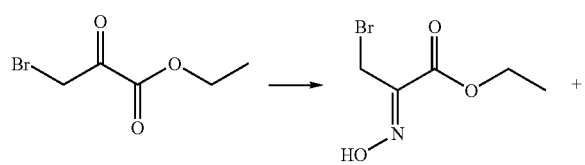

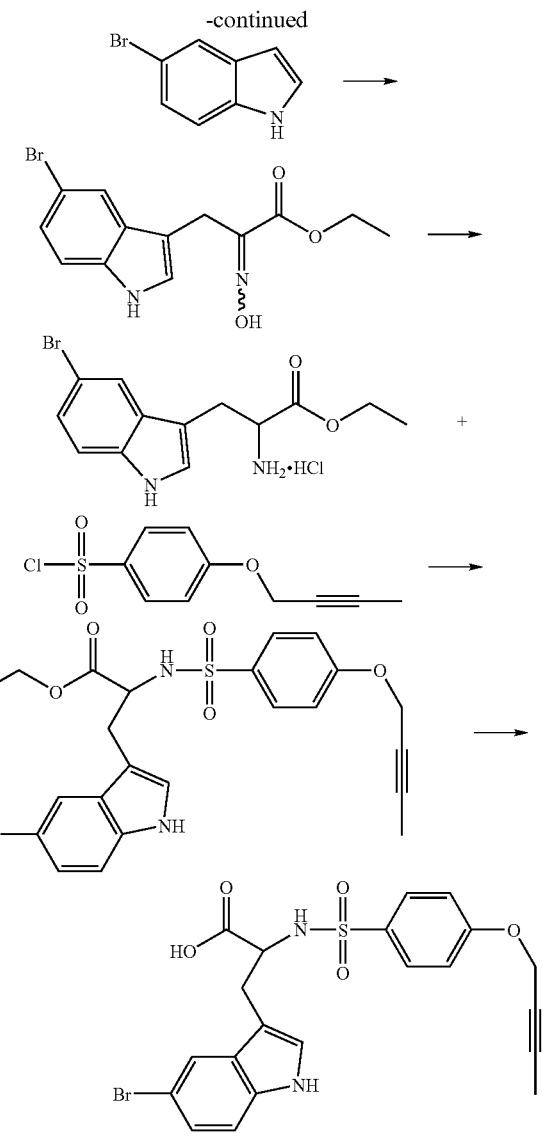

Step 1: Synthesis of
3-bromo-2-hydroxyimino-propionic Acid Ethyl Ester

Gilchrist, T. L. and T. G Roberts, *J. Chem, Soc. Perkin Trans* 1, 1983, 1283-1292, is incorporated herein by reference in its entirety.

A solution of hydroxylamine sulfate (5.00 g, 31 mmol) in water (30 mL) was added to a solution of ethylbrompyruvate (90%) (6.50 g, 30 mmol) in CHCl₃ (10 mL). The two-phase system was rapidly stirred for 24 hours at room temperature. The mixture was extracted with CHCl₃ (3×30 mL). The combined extracts were dried over Na₂SO₄ and concentrated to give 7.00 g of the title compound as a white solid. $^1$H NMR (CDCl₃): 300 MHz δ 10.08 (bs, 1H), 4.38 (q, J=7.2 Hz, 2H), 4.27 (s, 2H), 1.39 (t, J=7.2 Hz, 3H).

Step 2: Synthesis of 2-hydroxyimino-3-(5-bromo-1H-indol-3-yl)-propionic Acid Ethyl Ester A solution of 3-bromo-2-hydroxyimino-propionic acid ethyl ester (3.21 g, 15.3 mmol) in CH₂Cl₂ (20 mL) was slowly added dropwise to a stirring mixture of 5-bromoindole (3.0 g, 15.3 mmol) and $Na_2CO_3$ (8.92 g, 84.2 mmol) in $CH_2Cl_2$ (30 mL) at room temperature. The mixture was stirred for 20 hours, filtered through CELITE® and concentrated to give 4.94 g of the title compound as a crude material. LCMS m/z (ESI) $[M+H]^+$ calcd for $C_{13}H_{14}BrN_2O_3$ ($Br^{79}$) 325.2, found 325.2.

Step 3: Synthesis of 2-amino-3-(5-bromo-1H-indol-3-yl)-propionic Acid Ethyl Ester Zinc dust (3.30 g, 50.4 mmol) was added portionwise to a stirred solution of 2-hydroxyimino-3-(5-bromo-1H-indol-3-yl)-propionic acid ethyl ester (4.10 g, 12.61 mmol) in acetic acid (100 mL) over 30 min. After stirring overnight, the mixture was filtered through CELITE® and concentrated. The residue was dissolved in 1 N HCl and re-evaporated to give 4.30 g of the title compound as a crude material. LCMS m/z (ESI) $[M–HCl+H]^+$ calcd for $C_{13}H_{15}BrN_2O_2$ ($Br^{79}$) 312.2, found 312.2.

Step 4: Synthesis of 2-(4-but-2-ynyloxy-benzenesulfonylamino)-3-(5-bromo-1H-indol-3-yl)-propionic Acid Ethyl Ester Triethylamine (4.81 mL, 34.5 mmol) was added to a mixture of 2-amino-3-(5-bromo-1H-indol-3-yl)-propionic acid ethyl ester (4.00 g, 11.51 mmol) and 4-but-2-ynyloxy-benzenesulfonyl chloride (3.10 g, 12.66 mmol) in $H_2O$-dioxane (40 mL/60 mL) at room temperature. The reaction mixture was stirred for 20 hours at room temperature. The mixture was concentrated and diluted with ethyl acetate. The organic solution was washed with $H_2O$ and brine, dried over $Na_2SO_4$ and concentrated. The residue was purified by flash column chromatography (silica, 40% ethyl acetate in hexanes) to give 3.67 g of the title compound as a pale yellow solid. $^1$H NMR (DMSO-$d_6$): 400 MHz δ 11.05 (s, 1H), 8.31 (d, J=8.8 Hz, 1H), 7.56 (d, J=8.8 Hz, 2H), 7.45 (d, J=1.6 Hz, 1H), 7.27 (d, J=8.4 Hz, 1H), 7.14 (m, 2H), 6.99 (d, J=8.8 Hz, 2H), 4.80 (q, J=2.4 Hz, 2H), 3.88 (q, J=7.6 Hz, 1H), 3.75 (q, J=7.2 Hz, 2H), 3.00 (dd J=14.4, 7.2 Hz, 1H), 2.88 (dd J=14.4, 7.6 Hz, 1H), 1.82 (t, J=2.4 Hz, 3H), 0.92 (t, J=7.2 Hz, 3H); HRMS: calcd for $C_{23}H_{24}BrN_2O_5S$ (ESI+, $Br^{79}$, $[M+H]^{1+}$), 519.0584; found 519.0589.

Step 5: Synthesis of 3-(5-bromo-1H-indol-3-yl)-2-(4-but-2-ynyloxy-benzenesulfonyl amino)-propionic Acid 2-(4-But-2-ynyloxy-benzenesulfonylamino)-3-(5-bromo-1H-indol-3-yl)-propionic acid ethyl ester (0.100 g, 0.193 mmol) was dissolved in 0.5 mL tetrahydrofuran. To the solution was added MeOH (0.5 mL) and 1 N NaOH (0.4 mL, 0.4 mmol). The reaction mixture was placed in a shaker for 10 hours at room temperature. The solution was acidified with 1N HCl and extracted with ethyl acetate (3×3 mL). The organic solution was concentrated and the residue was purified by RP-HPLC to give 0.089 g (94%) of the title compound as a pale yellow solid. $^1$H NMR (DMSO-$d_6$): 400 MHz δ 12.65 (bs, 1H), 11.01 (s, 1H), 8.08 (d, J=8.8 Hz, 1H), 7.48 (m, 3H), 7.26 (d, J=8.8 Hz, 1H), 7.13 (m, 2H), 6.89 (d, J=9.2 Hz, 2H), 4.77 (q, J=2.8 Hz, 2H), 3.82 (q, J=8.4 Hz, 1H), 3.01 (dd J=14.6, 6.4 Hz, 1H), 2.82 (dd J=14.6, 8.0 Hz, 1H), 1.83 (t, J=2.4 Hz, 3H); HRMS: calcd for $C_{21}H_{20}BrN_2O_5S$ (ESI+, $Br^{79}$, $[M+H]^{1+}$), 491.0271; found 491.0287; LCMS m/z (ESI) [M–H] 489 ($Br^{79}$), retention time=2.75 min.

Preparation of Compound of Example 47

2-(4-BUT-2-YNYLOXY-BENZENESULFONYLAMINO)-3-[1-(4-METHOXY-BENZYL)-5-METHYL-1H-INDOL-3-YL]-PROPIONIC Acid

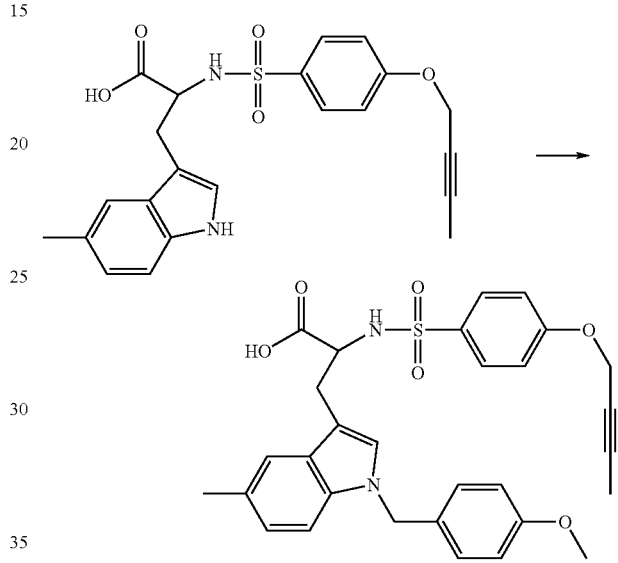

In a 20 mL vial, NaH (60% in mineral oil) (0.033 g, 0.831 mmol) was added to a solution of 2-(4-but-2-ynyloxy-benzenesulfonylamino)-3-(5-methyl-1H-indol-3-yl)-propionic acid (Example 1) (0.100 g, 0.234 mmol) in anhydrous N,N-dimethylformamide (2 mL) at 0° C. The reaction mixture was placed in a shaker for 20 min. at 0° C. 4-Methoxy-benzyl chloride (0.032 mL, 0.234 mmol) was added to the solution and allowed to react for 10 hours at 0° C. The reaction mixture was quenched with $H_2O$ and acidified with HCl. The solution was extracted with EtOAc, washed with $H_2O$ and brine, dried over $Na_2SO_4$, and concentrated. The residue was purified by RP-HPLC to give 0.086 g (67%) of the title compound as a pale yellow solid. $^1$H NMR (DMSO-$d_6$): 400 MHz δ 12.58 (bs, 1H), 8.09 (d, J=8.4 Hz, 1H), 7.53 (d, J=11.6 Hz, 2H), 7.20 (d, J=8.0 Hz, 1H), 7.09 (s, 1H), 7.07 (d, J=8.4 Hz, 2H), 7.00 (s, 1H), 6.92-6.80 (m, 5H), 5.17 (s, 2H), 4.76 (q, J=2.4 Hz, 2H), 3.82 (q, J=8.0 Hz, 1H), 3.69 (s, 3H), 3.00 (dd J=14.4, 6.8 Hz, 1H), 2.79 (dd J=14.4, 7.6 Hz, 1H), 2.32 (s, 3H), 1.82 (t, J=2.4 Hz, 3H); HRMS: calcd for $C_{30}H_{31}N_2O_6S$ (ESI+, $[M+H]^{1+}$), 547.1897; found 547.1896; LCMS m/z (ESI) [M–H] 545, retention time=2.76 min.

The following compounds were prepared according to the procedures of the Synthetic Procedures described above, using the starting materials (SM1/SM2) as described in the Table below.

| Example | Compound Name | Prepared by using same synthetic procedures of Example # | SM1 (indole or tryptophan) | SM2 (alkyl halide, N/A = not applicable) |
|---|---|---|---|---|
| 1 | N-{[4-(but-2-ynyloxy)phenyl]sulfonyl}-D-tryptophan | 6 (step 1) | D-tryptophan | N/A |
| 2 | N-{[4-(but-2-ynyloxy)phenyl]sulfonyl}-L-tryptophan | 6 (step 1) | L-tryptophan | N/A |
| 3 | N-{[4-(but-2-ynyloxy)phenyl]sulfonyl}-5-fluorotryptophan | 6 (step 1) | 5-fluorotryptophan | N/A |
| 4 | N-{[4-(but-2-ynyloxy)phenyl]sulfonyl}-5-methoxytryptophan | 6 (step 1) | 5-methoxytryptophan | N/A |
| 5 | N-{[4-(but-2-ynyloxy)phenyl]sulfonyl}-5-hydroxytryptophan | 6 (step 1) | 5-hydroxytryptophan | N/A |
| 6 | N-{[4-(but-2-ynyloxy)phenyl]sulfonyl}-5-methyltryptophan | 6 (step 1) | 5-methyltryptophan | N/A |
| 7 | N-{[4-(but-2-ynyloxy)phenyl]sulfonyl}-6-fluorotryptophan | 6 (step 1) | 6-fluorotryptophan | N/A |
| 8 | N-{[4-(but-2-ynyloxy)phenyl]sulfonyl}-6-methyltryptophan | 6 (step 1) | 6-methyltryptophan | N/A |
| 9 | N-{[4-(but-2-ynyloxy)phenyl]sulfonyl}-alpha-methyltryptophan | 6 (step 1) | alpha-methyltryptophan | N/A |
| 10 | N-{[4-(but-2-ynyloxy)phenyl]sulfonyl}-7-methyltryptophan | 6 (step 1) | 7-methyltryptophan | N/A |
| 11 | N-{[4-(but-2-ynyloxy)phenyl]sulfonyl}-5-hydroxy-L-tryptophan | 6 (step 1) | 5-hydroxy-L-tryptophan | N/A |
| 12 | N-{[4-(but-2-ynyloxy)phenyl]sulfonyl}-1-propyl-L-tryptophan | 32 | L-tryptophan | n-propyl bromide |
| 13 | 1-butyl-N-{[4-(but-2-ynyloxy)phenyl]sulfonyl}-L-tryptophan | 32 | L-tryptophan | n-butyl bromide |
| 14 | N-{[4-(but-2-ynyloxy)phenyl]sulfonyl}-1-isobutyl-L-tryptophan | 32 | L-tryptophan | 2-methylpropyl bromide |
| 15 | 1-allyl-N-{[4-(but-2-ynyloxy)phenyl]sulfonyl}-L-tryptophan | 32 | L-tryptophan | allyl bromide |
| 16 | N-{[4-(but-2-ynyloxy)phenyl]sulfonyl}-1-(3-methylbenzyl)-L-tryptophan | 32 | L-tryptophan | 3-methylbenzyl bromide |
| 17 | N-{[4-(but-2-ynyloxy)phenyl]sulfonyl}-1-(4-methylbenzyl)-L-tryptophan | 32 | L-tryptophan | 4-methylbenzyl bromide |
| 18 | N-{[4-(but-2-ynyloxy)phenyl]sulfonyl}-1-(4-chlorobenzyl)-L-tryptophan | 32 | L-tryptophan | 4-chlorobenzyl bromide |
| 19 | N-{[4-(but-2-ynyloxy)phenyl]sulfonyl}-1-(4-methoxybenzyl)-L-tryptophan | 32 | L-tryptophan | 4-methoxybenzyl bromide |
| 20 | 5-(benzyloxy)-N-{[4-(but-2-ynyloxy)phenyl]sulfonyl}tryptophan | 20 | 5-benzyloxy-D/L-tryptophan | N/A |
| 21 | N-{[4-(but-2-ynyloxy)phenyl]sulfonyl}-1-methyl-D-tryptophan | 32 | D-tryptophan | iodomethane |
| 22 | N-{[4-(but-2-ynyloxy)phenyl]sulfonyl}-1-pentyl-D-tryptophan | 32 | D-tryptophan | 1-bromo-pentane |
| 23 | N-{[4-(but-2-ynyloxy)phenyl]sulfonyl}-1-(cyclohexylmethyl)-D-tryptophan | 32 | D-tryptophan | bromomethyl cyclohexane |

-continued

| Example | Compound Name | Prepared by using same synthetic procedures of Example # | SM1 (indole or tryptophan) | SM2 (alkyl halide, N/A = not applicable) |
|---|---|---|---|---|
| 24 | N-{[4-(but-2-ynyloxy)phenyl]sulfonyl}-1-(4-phenoxybutyl)-D-tryptophan | 32 | D-tryptophan | 4-phenoxybutyl bromide |
| 25 | 1-benzyl-N-{[4-(but-2-ynyloxy)phenyl]sulfonyl}-D-tryptophan | 32 | D-tryptophan | benzyl bromide |
| 26 | N-{[4-(but-2-ynyloxy)phenyl]sulfonyl}-1-(4-methylbenzyl)-D-tryptophan | 32 | D-tryptophan | 4-methylbenzyl bromide |
| 27 | 1-(1,1'-biphenyl-2-ylmethyl)-N-{[4-(but-2-ynyloxy)phenyl]sulfonyl}-D-tryptophan | 32 | D-tryptophan | 2-phenylbenzyl bromide |
| 28 | N-{[4-(but-2-ynyloxy)phenyl]sulfonyl}-1-(4-fluorobenzyl)-D-tryptophan | 32 | D-tryptophan | 4-fluorobenzyl bromide |
| 29 | N-{[4-(but-2-ynyloxy)phenyl]sulfonyl}-1-(2-naphthylmethyl)-D-tryptophan | 32 | D-tryptophan | 2-bromethyl naphthalene |
| 30 | N-{[4-(but-2-ynyloxy)phenyl]sulfonyl}-1-(pyridin-3-ylmethyl)-D-tryptophan | 32 | D-tryptophan | 3-bromomethyl-pyridine |
| 31 | N-{[4-(but-2-ynyloxy)phenyl]sulfonyl}-1-(cyclopropylmethyl)-D-tryptophan | 32 | D-tryptophan | bromethylcyclopropane |
| 32 | N-{[4-(but-2-ynyloxy)phenyl]sulfonyl}-1-(cyclobutylmethyl)-D-tryptophan | 32 | D-tryptophan | bromethylcyclobutane |
| 33 | N-{[4-(but-2-ynyloxy)phenyl]sulfonyl}-1-(2-cyclohexylethyl)-D-tryptophan | 32 | D-tryptophan | 1-bromo-2-cyclohexylethane |
| 34 | N-{[4-(but-2-ynyloxy)phenyl]sulfonyl}-1-(3-methoxybenzyl)-D-tryptophan | 32 | D-tryptophan | 3-methoxybenzyl chloride |
| 35 | N-{[4-(but-2-ynyloxy)phenyl]sulfonyl}-1-(4-methoxybenzyl)-D-tryptophan | 32 | D-tryptophan | 4-methoxybenzyl chloride |
| 36 | N-{[4-(but-2-ynyloxy)phenyl]sulfonyl}-1-(3,5-dimethoxybenzyl)-D-tryptophan | 32 | D-tryptophan | 3,5-dimethoxybenzyl chloride |
| 37 | 1-(1,3-benzodioxol-5-ylmethyl)-N-{[4-(but-2-ynyloxy)phenyl]sulfonyl}-D-tryptophan | 32 | D-tryptophan | 3,4-methylene dioxybenzyl chloride |
| 38 | N-{[4-(but-2-ynyloxy)phenyl]sulfonyl}-1-[4-(trifluoromethoxy)benzyl]-D-tryptophan | 32 | D-tryptophan | 4-trifluoromethoxy benzyl bromide |
| 39 | N-{[4-(but-2-ynyloxy)phenyl]sulfonyl}-1-[2-(trifluoromethyl)benzyl]-D-tryptophan | 32 | D-tryptophan | 2-trifluoromethyl benzyl bromide |
| 40 | N-{[4-(but-2-ynyloxy)phenyl]sulfonyl}-1-[3-(trifluoromethyl)benzyl]-D-tryptophan | 32 | D-tryptophan | 3-trifluoromethyl benzyl bromide |
| 41 | N-{[4-(but-2-ynyloxy)phenyl]sulfonyl}-1-[4-(trifluoromethyl)benzyl]-D-tryptophan | 32 | D-tryptophan | 4-trifluoromethyl benzyl bromide |

| Example | Compound Name | Prepared by using same synthetic procedures of Example # | SM1 (indole or tryptophan) | SM2 (alkyl halide, N/A = not applicable) |
|---|---|---|---|---|
| 42 | N-{[4-(but-2-ynyloxy)phenyl]sulfonyl}-1-(4-chlorobenzyl)-D-tryptophan | 32 | D-tryptophan | 4-chlorobenzyl chloride |
| 43 | N-{[4-(but-2-ynyloxy)phenyl]sulfonyl}-1-(2-cyanobenzyl)-D-tryptophan | 32 | D-tryptophan | 2-cyanobenzyl bromide |
| 44 | N-{[4-(but-2-ynyloxy)phenyl]sulfonyl}-1-(3-cyanobenzyl)-D-tryptophan | 32 | D-tryptophan | 3-cyanobenzyl bromide |
| 45 | N-{[4-(but-2-ynyloxy)phenyl]sulfonyl}-1-(4-cyanobenzyl)-D-tryptophan | 32 | D-tryptophan | 4-cyanobenzyl bromide |
| 46 | 5-bromo-N-{[4-(but-2-ynyloxy)phenyl]sulfonyl}tryptophan | 46 | 5-methylindole | N/A |
| 47 | N-{[4-(but-2-ynyloxy)phenyl]sulfonyl}-1-(4-methoxybenzyl)-5-methyltryptophan | 47 | 5-methylindole | 4-methoxybenzyl bromide |
| 48 | 1-benzyl-N-{[4-(but-2-ynyloxy)phenyl]sulfonyl}-5-methoxytryptophan | 46 and 47 | 5-methoxyindole | benzyl bromide |
| 49 | N-{[4-(but-2-ynyloxy)phenyl]sulfonyl}-5-methoxy-1-(2-methylbenzyl)tryptophan | 46 and 47 | 5-methoxyindole | 2-methylbenzyl bromide |
| 50 | N-{[4-(but-2-ynyloxy)phenyl]sulfonyl}-5-methoxy-1-(3-methylbenzyl)tryptophan | 46 and 47 | 5-methoxyindole | 3-methylbenzyl bromide |
| 51 | N-{[4-(but-2-ynyloxy)phenyl]sulfonyl}-5-methoxy-1-(2-methoxybenzyl)tryptophan | 46 and 47 | 5-methoxyindole | 2-methoxybenzyl bromide |
| 52 | N-{[4-(but-2-ynyloxy)phenyl]sulfonyl}-5-methoxy-1-(3-methoxybenzyl)tryptophan | 46 and 47 | 5-methoxyindole | 3-methoxybenzyl bromide |
| 53 | N-{[4-(but-2-ynyloxy)phenyl]sulfonyl}-5-methoxy-1-(4-methoxybenzyl)tryptophan | 46 and 47 | 5-methoxyindole | 4-methoxybenzyl bromide |
| 54 | N-{[4-(but-2-ynyloxy)phenyl]sulfonyl}-1-(3,5-dimethoxybenzyl)-5-methoxytryptophan | 46 and 47 | 5-methoxyindole | 3,5-dimethoxybenzyl bromide |
| 55 | N-{[4-(but-2-ynyloxy)phenyl]sulfonyl}-5-methoxy-1-[2-(trifluoromethyl)benzyl]tryptophan | 46 and 47 | 5-methoxyindole | 2-trifluoromethylbenzyl bromide |
| 56 | N-{[4-(but-2-ynyloxy)phenyl]sulfonyl}-5-methoxy-1-[3-(trifluoromethyl)benzyl]tryptophan | 46 and 47 | 5-methoxyindole | 3-trifluoromethylbenzyl bromide |
| 57 | N-{[4-(but-2-ynyloxy)phenyl]sulfonyl}-5-methoxy-1-[4-(trifluoromethyl)benzyl]tryptophan | 46 and 47 | 5-methoxyindole | 4-trifluoromethylbenzyl bromide |
| 58 | N-{[4-(but-2-ynyloxy)phenyl]sulfonyl}-1-(2-fluorobenzyl)-5-methoxytryptophan | 46 and 47 | 5-methoxyindole | 2-fluorobenzyl bromide |
| 59 | N-{[4-(but-2-ynyloxy)phenyl]sulfonyl}-1-(3-fluorobenzyl)-5-methoxytryptophan | 46 and 47 | 5-methoxyindole | 3-fluorobenzyl bromide |
| 60 | N-{[4-(but-2-ynyloxy)phenyl]sulfonyl}-1-(4-fluorobenzyl)-5-methoxytryptophan | 46 and 47 | 5-methoxyindole | 4-fluorobenzyl bromide |

| Example | Compound Name | Prepared by using same synthetic procedures of Example # | SM1 (indole or tryptophan) | SM2 (alkyl halide, N/A = not applicable) |
|---|---|---|---|---|
| 61 | N-{[4-(but-2-ynyloxy)phenyl]sulfonyl}-1-(3,5-difluorobenzyl)-5-methoxytryptophan | 46 and 47 | 5-methoxyindole | 3,5-difluorobenzyl bromide |
| 62 | N-{[4-(but-2-ynyloxy)phenyl]sulfonyl}-1-(4-chlorobenzyl)-5-methoxytryptophan | 46 and 47 | 5-methoxyindole | 4-chlorobenzyl bromide |
| 63 | N-{[4-(but-2-ynyloxy)phenyl]sulfonyl}-1-(4-isopropylbenzyl)-5-methoxytryptophan | 46 and 47 | 5-methoxyindole | 4-isopropylbenzyl bromide |
| 64 | N-{[4-(but-2-ynyloxy)phenyl]sulfonyl}-1-(2-cyanobenzyl)-5-methoxytryptophan | 46 and 47 | 5-methoxyindole | 2-cyanobenzyl bromide |
| 65 | 1-(1,3-benzodioxol-5-ylmethyl)-N-{[4-(but-2-ynyloxy)phenyl]sulfonyl}-5-methoxytryptophan | 46 and 47 | 5-methoxyindole | 5-bromomethyl-benzo[1,3]dioxole |
| 66 | N-{[4-(but-2-ynyloxy)phenyl]sulfonyl}-5-methoxy-1-(pyridin-3-ylmethyl)tryptophan | 46 and 47 | 5-methoxyindole | 3-bromomethyl-pyridine |
| 67 | N-{[4-(but-2-ynyloxy)phenyl]sulfonyl}-1-isobutyl-5-methoxytryptophan | 46 and 47 | 5-methoxyindole | 4-isopropylbenzyl bromide |
| 68 | N-{[4-(but-2-ynyloxy)phenyl]sulfonyl}-5-methoxy-1-pentyltryptophan | 46 and 47 | 5-methoxyindole | 1-bromo-pentane |
| 69 | N-{[4-(but-2-ynyloxy)phenyl]sulfonyl}-1-(cyclobutylmethyl)-5-methoxytryptophan | 46 and 47 | 5-methoxyindole | bromomethyl-cyclobutane |
| 70 | N-{[4-(but-2-ynyloxy)phenyl]sulfonyl}-1-(cyclohexylmethyl)-5-methoxytryptophan | 46 and 47 | 5-methoxyindole | bromomethyl-cyclohexane |
| 71 | 1-benzyl-N-{[4-(but-2-ynyloxy)phenyl]sulfonyl}-5-chlorotryptophan | 46 and 47 | 5-chloroindole | benzyl bromide |
| 72 | N-{[4-(but-2-ynyloxy)phenyl]sulfonyl}-5-chloro-1-(2-methylbenzyl)tryptophan | 46 and 47 | 5-chloroindole | 2-methylbenzyl bromide |
| 73 | N-{[4-(but-2-ynyloxy)phenyl]sulfonyl}-5-chloro-1-(3-methylbenzyl)tryptophan | 46 and 47 | 5-chloroindole | 3-methylbenzyl bromide |
| 74 | N-{[4-(but-2-ynyloxy)phenyl]sulfonyl}-5-chloro-1-(2-methoxybenzyl)tryptophan | 46 and 47 | 5-chloroindole | 2-methoxybenzyl bromide |
| 75 | N-{[4-(but-2-ynyloxy)phenyl]sulfonyl}-5-chloro-1-(3-methoxybenzyl)tryptophan | 46 and 47 | 5-chloroindole | 3-methoxybenzyl bromide |
| 76 | N-{[4-(but-2-ynyloxy)phenyl]sulfonyl}-5-chloro-1-(4-methoxybenzyl)tryptophan | 46 and 47 | 5-chloroindole | 4-methoxybenzyl bromide |
| 77 | N-{[4-(but-2-ynyloxy)phenyl]sulfonyl}-5-chloro-1-[4-(trifluoromethyl)benzyl]tryptophan | 46 and 47 | 5-chloroindole | 4-trifluoromethyl benzyl bromide |
| 78 | N-{[4-(but-2-ynyloxy)phenyl]sulfonyl}-5-chloro-1-[4-(trifluoromethoxy)benzyl]tryptophan | 46 and 47 | 5-chloroindole | 4-trifluoromethoxy benzyl bromide |

-continued

| Example | Compound Name | Prepared by using same synthetic procedures of Example # | SM1 (indole or tryptophan) | SM2 (alkyl halide, N/A = not applicable) |
|---|---|---|---|---|
| 79 | N-{[4-(but-2-ynyloxy)phenyl]sulfonyl}-5-chloro-1-(2-fluorobenzyl)tryptophan | 46 and 47 | 5-chloroindole | 2-fluorobenzyl bromide |
| 80 | N-{[4-(but-2-ynyloxy)phenyl]sulfonyl}-5-chloro-1-(3-fluorobenzyl)tryptophan | 46 and 47 | 5-chloroindole | 3-fluorobenzyl bromide |
| 81 | N-{[4-(but-2-ynyloxy)phenyl]sulfonyl}-5-chloro-1-(4-chlorobenzyl)tryptophan | 46 and 47 | 5-chloroindole | 4-chlorobenzyl bromide |
| 82 | N-{[4-(but-2-ynyloxy)phenyl]sulfonyl}-5-chloro-1-(4-isopropylbenzyl)tryptophan | 46 and 47 | 5-chloroindole | 4-isopropylbenzyl bromide |
| 83 | 1-(1,3-benzodioxol-5-ylmethyl)-N-{[4-(but-2-ynyloxy)phenyl]sulfonyl}-5-chlorotryptophan | 46 and 47 | 5-chloroindole | 5-bromomethyl-benzo[1,3]dioxole |
| 84 | N-{[4-(but-2-ynyloxy)phenyl]sulfonyl}-5-chloro-1-(pyridin-3-ylmethyl)tryptophan | 46 and 47 | 5-chloroindole | 3-bromomethyl-pyridine |
| 85 | N-{[4-(but-2-ynyloxy)phenyl]sulfonyl}-5-chloro-1-isobutyltryptophan | 46 and 47 | 5-chloroindole | 4-isopropylbenzyl bromide |
| 86 | N-{[4-(but-2-ynyloxy)phenyl]sulfonyl}-5-chloro-1-(cyclobutylmethyl)tryptophan | 46 and 47 | 5-chloroindole | bromomethyl-cyclobutane |
| 87 | N-{[4-(but-2-ynyloxy)phenyl]sulfonyl}-5-chloro-1-(cyclohexylmethyl)tryptophan | 46 and 47 | 5-chloroindole | bromomethyl-cyclohexane |
| 88 | 1-benzyl-N-{[4-(but-2-ynyloxy)phenyl]sulfonyl}-5-chloro-2-methyltryptophan | 46 and 47 | 5-chloro-2-methylindole | benzyl bromide |
| 89 | N-{[4-(but-2-ynyloxy)phenyl]sulfonyl}-5-chloro-1-(2-methoxybenzyl)-2-methyltryptophan | 46 and 47 | 5-chloro-2-methylindole | 2-methoxybenzyl bromide |
| 90 | N-{[4-(but-2-ynyloxy)phenyl]sulfonyl}-5-chloro-1-(3-methoxybenzyl)-2-methyltryptophan | 46 and 47 | 5-chloro-2-methylindole | 3-methoxybenzyl bromide |
| 91 | N-{[4-(but-2-ynyloxy)phenyl]sulfonyl}-5-chloro-1-(4-methoxybenzyl)-2-methyltryptophan | 46 and 47 | 5-chloro-2-methylindole | 4-methoxybenzyl bromide |
| 92 | N-{[4-(but-2-ynyloxy)phenyl]sulfonyl}-5-chloro-2-methyl-1-(4-methylbenzyl)tryptophan | 46 and 47 | 5-chloro-2-methylindole | 4-methylbenzyl bromide |
| 93 | N-{[4-(but-2-ynyloxy)phenyl]sulfonyl}-5-chloro-2-methyl-1-[4-(trifluoromethyl)benzyl]tryptophan | 46 and 47 | 5-chloro-2-methylindole | 4-trifluoromethyl benzyl bromide |
| 94 | N-{[4-(but-2-ynyloxy)phenyl]sulfonyl}-5-chloro-2-methyl-1-[4-(trifluoromethoxy)benzyl]tryptophan | 46 and 47 | 5-chloro-2-methylindole | 4-trifluoromethoxy benzyl bromide |
| 95 | N-{[4-(but-2-ynyloxy)phenyl]sulfonyl}-5-chloro-1-(4-fluorobenzyl)-2-methyltryptophan | 46 and 47 | 5-chloro-2-methylindole | 4-fluorobenzyl bromide |

-continued

| Example | Compound Name | Prepared by using same synthetic procedures of Example # | SM1 (indole or tryptophan) | SM2 (alkyl halide, N/A = not applicable) |
|---|---|---|---|---|
| 96 | N-{[4-(but-2-ynyloxy)phenyl]sulfonyl}-5-chloro-1-(4-chlorobenzyl)-2-methyltryptophan | 46 and 47 | 5-chloro-2-methylindole | 4-chlorobenzyl bromide |
| 97 | N-{[4-(but-2-ynyloxy)phenyl]sulfonyl}-5-chloro-1-(4-isopropylbenzyl)-2-methyltryptophan | 46 and 47 | 5-chloro-2-methylindole | 4-isopropylbenzyl bromide |
| 98 | N-{[4-(but-2-ynyloxy)phenyl]sulfonyl}-5-chloro-1-(4-cyanobenzyl)-2-methyltryptophan | 46 and 47 | 5-chloro-2-methylindole | 4-cyanobenzyl bromide |
| 99 | N-{[4-(but-2-ynyloxy)phenyl]sulfonyl}-5-chloro-2-methyl-1-(pyridin-3-ylmethyl)tryptophan | 46 and 47 | 5-chloro-2-methylindole | 3-bromomethyl-pyridine |
| 100 | 1-(1,3-benzodioxol-5-ylmethyl)-N-{[4-(but-2-ynyloxy)phenyl]sulfonyl}-5-chloro-2-methyltryptophan | 46 and 47 | 5-chloro-2-methylindole | 5-bromomethyl-benzo[1,3]dioxole |
| 101 | N-{[4-(but-2-ynyloxy)phenyl]sulfonyl}-5-chloro-1-isobutyl-2-methyltryptophan | 46 and 47 | 5-chloro-2-methylindole | 2-methylpropyl bromide |
| 102 | N-{[4-(but-2-ynyloxy)phenyl]sulfonyl}-5-chloro-1-(cyclohexylmethyl)-2-methyltryptophan | 46 and 47 | 5-chloro-2-methylindole | bromomethyl-cyclohexane |
| 103 | 1-benzyl-N-{[4-(but-2-ynyloxy)phenyl]sulfonyl}-5-carboxytryptophan | 46 and 47 | 1H-Indole-5-carboxylic acid methyl ester | benzyl bromide |
| 104 | N-{[4-(but-2-ynyloxy)phenyl]sulfonyl}-5-carboxy-1-(2-methylbenzyl)tryptophan | 46 and 47 | 1H-Indole-5-carboxylic acid methyl ester | 2-methylbenzyl bromide |
| 105 | N-{[4-(but-2-ynyloxy)phenyl]sulfonyl}-5-carboxy-1-(3-methylbenzyl)tryptophan | 46 and 47 | 1H-Indole-5-carboxylic acid methyl ester | 3-methylbenzyl bromide |
| 106 | N-{[4-(but-2-ynyloxy)phenyl]sulfonyl}-5-carboxy-1-(4-methylbenzyl)tryptophan | 46 and 47 | 1H-Indole-5-carboxylic acid methyl ester | 4-methylbenzyl bromide |
| 107 | N-{[4-(but-2-ynyloxy)phenyl]sulfonyl}-5-carboxy-1-(2-methoxybenzyl)tryptophan | 46 and 47 | 1H-Indole-5-carboxylic acid methyl ester | 2-methoxybenzyl bromide |
| 108 | N-{[4-(but-2-ynyloxy)phenyl]sulfonyl}-5-carboxy-1-(3-methoxybenzyl)tryptophan | 46 and 47 | 1H-Indole-5-carboxylic acid methyl ester | 3-methoxybenzyl bromide |
| 109 | N-{[4-(but-2-ynyloxy)phenyl]sulfonyl}-5-carboxy-1-(4-methoxybenzyl)tryptophan | 46 and 47 | 1H-Indole-5-carboxylic acid methyl ester | 4-methoxybenzyl bromide |
| 110 | N-{[4-(but-2-ynyloxy)phenyl]sulfonyl}-5-carboxy-1-(3,5-dimethoxybenzyl)tryptophan | 46 and 47 | 1H-Indole-5-carboxylic acid methyl ester | 3,5-dimethoxybenzyl bromide |
| 111 | N-{[4-(but-2-ynyloxy)phenyl]sulfonyl}-5-carboxy-1-[2-(trifluoromethyl)benzyl]tryptophan | 46 and 47 | 1H-Indole-5-carboxylic acid methyl ester | 2-trifluoromethyl benzyl bromide |
| 112 | N-{[4-(but-2-ynyloxy)phenyl]sulfonyl}-5-carboxy-1-[3-(trifluoromethyl)benzyl]tryptophan | 46 and 47 | 1H-Indole-5-carboxylic acid methyl ester | 3-trifluoromethyl benzyl bromide |
| 113 | N-{[4-(but-2-ynyloxy)phenyl]sulfonyl}-5-carboxy-1-[4-(trifluoromethyl)benzyl]tryptophan | 46 and 47 | 1H-Indole-5-carboxylic acid methyl ester | 4-trifluoromethyl benzyl bromide |

| Example | Compound Name | Prepared by using same synthetic procedures of Example # | SM1 (indole or tryptophan) | SM2 (alkyl halide, N/A = not applicable) |
|---|---|---|---|---|
| 114 | N-{[4-(but-2-ynyloxy)phenyl]sulfonyl}-5-carboxy-1-[4-(trifluoromethoxy)benzyl]tryptophan | 46 and 47 | 1H-Indole-5-carboxylic acid methyl ester | 4-trifluoromethoxy benzyl bromide |
| 115 | N-{[4-(but-2-ynyloxy)phenyl]sulfonyl}-5-carboxy-1-(2-fluorobenzyl)tryptophan | 46 and 47 | 1H-Indole-5-carboxylic acid methyl ester | 2-fluorobenzyl bromide |
| 116 | N-{[4-(but-2-ynyloxy)phenyl]sulfonyl}-5-carboxy-1-(3-fluorobenzyl)tryptophan | 46 and 47 | 1H-Indole-5-carboxylic acid methyl ester | 3-fluorobenzyl bromide |
| 117 | N-{[4-(but-2-ynyloxy)phenyl]sulfonyl}-5-carboxy-1-(4-fluorobenzyl)tryptophan | 46 and 47 | 1H-Indole-5-carboxylic acid methyl ester | 4-fluorobenzyl bromide |
| 118 | N-{[4-(but-2-ynyloxy)phenyl]sulfonyl}-5-carboxy-1-(3,5-difluorobenzyl)tryptophan | 46 and 47 | 1H-Indole-5-carboxylic acid methyl ester | 3,5-difluorobenzyl bromide |
| 119 | N-{[4-(but-2-ynyloxy)phenyl]sulfonyl}-5-carboxy-1-(4-chlorobenzyl)tryptophan | 46 and 47 | 1H-Indole-5-carboxylic acid methyl ester | 4-chlorobenzyl bromide |
| 120 | N-{[4-(but-2-ynyloxy)phenyl]sulfonyl}-5-carboxy-1-(4-isopropylbenzyl)tryptophan | 46 and 47 | 1H-Indole-5-carboxylic acid methyl ester | 4-isopropylbenzyl bromide |
| 121 | N-{[4-(but-2-ynyloxy)phenyl]sulfonyl}-5-carboxy-1-(2-cyanobenzyl)tryptophan | 46 and 47 | 1H-Indole-5-carboxylic acid methyl ester | 2-cyanobenzyl bromide |
| 122 | N-{[4-(but-2-ynyloxy)phenyl]sulfonyl}-5-carboxy-1-(3-cyanobenzyl)tryptophan | 46 and 47 | 1H-Indole-5-carboxylic acid methyl ester | 3-cyanobenzyl bromide |
| 123 | N-{[4-(but-2-ynyloxy)phenyl]sulfonyl}-5-carboxy-1-(4-cyanobenzyl)tryptophan | 46 and 47 | 1H-Indole-5-carboxylic acid methyl ester | 4-cyanobenzyl bromide |
| 124 | 1-(1,3-benzodioxol-5-ylmethyl)-N-{[4-(but-2-ynyloxy)phenyl]sulfonyl}-5-carboxytryptophan | 46 and 47 | 1H-Indole-5-carboxylic acid methyl ester | 5-bromomethyl-benzo[1,3]dioxole |
| 125 | N-{[4-(but-2-ynyloxy)phenyl]sulfonyl}-5-carboxy-1-(pyridin-3-ylmethyl)tryptophan | 46 and 47 | 1H-Indole-5-carboxylic acid methyl ester | 3-bromomethyl-pyridine |
| 126 | N-{[4-(but-2-ynyloxy)phenyl]sulfonyl}-5-carboxy-1-(4-carboxybenzyl)tryptophan | 46 and 47 | 1H-Indole-5-carboxylic acid methyl ester | 4-Chloromethyl-benzoic acid |
| 127 | N-{[4-(but-2-ynyloxy)phenyl]sulfonyl}-5-carboxy-1-methyltryptophan | 46 and 47 | 1H-Indole-5-carboxylic acid methyl ester | iodomethane |
| 128 | N-{[4-(but-2-ynyloxy)phenyl]sulfonyl}-5-carboxy-1-ethyltryptophan | 46 and 47 | 1H-Indole-5-carboxylic acid methyl ester | ethyl bromide |
| 129 | N-{[4-(but-2-ynyloxy)phenyl]sulfonyl}-5-carboxy-1-isobutyltryptophan | 46 and 47 | 1H-Indole-5-carboxylic acid methyl ester | 2-methylpropyl bromide |
| 130 | N-{[4-(but-2-ynyloxy)phenyl]sulfonyl}-5-carboxy-1-pentyltryptophan | 46 and 47 | 1H-Indole-5-carboxylic acid methyl ester | 1-bromo-pentane |
| 131 | N-{[4-(but-2-ynyloxy)phenyl]sulfonyl}-5-carboxy-1-(cyclobutylmethyl)tryptophan | 46 and 47 | 1H-Indole-5-carboxylic acid methyl ester | bromomethyl-cyclobutane |

-continued

| Example | Compound Name | Prepared by using same synthetic procedures of Example # | SM1 (indole or tryptophan) | SM2 (alkyl halide, N/A = not applicable) |
|---|---|---|---|---|
| 132 | N-{[4-(but-2-ynyloxy)phenyl]sulfonyl}-5-carboxy-1-(cyclohexylmethyl)tryptophan | 46 and 47 | 1H-Indole-5-carboxylic acid methyl ester | bromomethylcyclohexane |
| 133 | N-{[4-(but-2-ynyloxy)phenyl]sulfonyl}-5-chlorotryptophan | 46 | 5-chloroindole | N/A |
| 134 | N-{[4-(but-2-ynyloxy)phenyl]sulfonyl}-2-methyltryptophan | 46 | 2-methylindole | N/A |
| 135 | 1-benzyl-N-{[4-(but-2-ynyloxy)phenyl]sulfonyl}-5-cyanotryptophan | 46 and 47 | 5-cyanoindole | benzyl bromide |
| 136 | N-{[4-(but-2-ynyloxy)phenyl]sulfonyl}-5-cyano-1-(4-methylbenzyl)tryptophan | 46 and 47 | 5-cyanoindole | 4-methylbenzyl bromide |
| 137 | N-{[4-(but-2-ynyloxy)phenyl]sulfonyl}-5-cyano-1-(2-methoxybenzyl)tryptophan | 46 and 47 | 5-cyanoindole | 2-methoxybenzyl bromide |
| 138 | N-{[4-(but-2-ynyloxy)phenyl]sulfonyl}-5-cyano-1-(3-methoxybenzyl)tryptophan | 46 and 47 | 5-cyanoindole | 3-methoxybenzyl bromide |
| 139 | N-{[4-(but-2-ynyloxy)phenyl]sulfonyl}-5-cyano-1-(4-methoxybenzyl)tryptophan | 46 and 47 | 5-cyanoindole | 4-methoxybenzyl bromide |
| 140 | N-{[4-(but-2-ynyloxy)phenyl]sulfonyl}-5-cyano-1-[4-(trifluoromethoxy)benzyl]tryptophan | 46 and 47 | 5-cyanoindole | 4-trifluoromethoxybenzyl bromide |
| 141 | N-{[4-(but-2-ynyloxy)phenyl]sulfonyl}-5-cyano-1-(4-fluorobenzyl)tryptophan | 46 and 47 | 5-cyanoindole | 4-fluorobenzyl bromide |
| 142 | N-{[4-(but-2-ynyloxy)phenyl]sulfonyl}-5-cyano-1-(4-isopropylbenzyl)tryptophan | 46 and 47 | 5-cyanoindole | 4-isopropylbenzyl bromide |
| 143 | N-{[4-(but-2-ynyloxy)phenyl]sulfonyl}-5-cyano-1-isobutyltryptophan | 46 and 47 | 5-cyanoindole | 2-methylpropylbromide |
| 144 | 1-benzyl-N-{[4-(but-2-ynyloxy)phenyl]sulfonyl}-2-methyltryptophan | 46 and 47 | 2-methylindole | benzyl bromide |
| 145 | N-{[4-(but-2-ynyloxy)phenyl]sulfonyl}-2-methyl-1-(2-methylbenzyl)tryptophan | 46 and 47 | 2-methylindole | 2-methylbenzyl bromide |
| 146 | N-{[4-(but-2-ynyloxy)phenyl]sulfonyl}-1-(2-methoxybenzyl)-2-methyltryptophan | 46 and 47 | 2-methylindole | 2-methoxybenzyl bromide |
| 147 | N-{[4-(but-2-ynyloxy)phenyl]sulfonyl}-1-(3-methoxybenzyl)-2-methyltryptophan | 46 and 47 | 2-methylindole | 3-methoxybenzyl bromide |
| 148 | N-{[4-(but-2-ynyloxy)phenyl]sulfonyl}-1-(4-methoxybenzyl)-2-methyltryptophan | 46 and 47 | 2-methylindole | 4-methoxybenzyl bromide |
| 149 | N-{[4-(but-2-ynyloxy)phenyl]sulfonyl}-2-methyl-1-[3-(trifluoromethyl)benzyl]tryptophan | 46 and 47 | 2-methylindole | 3-trifluoromethylbenzyl bromide |
| 150 | N-{[4-(but-2-ynyloxy)phenyl]sulfonyl}-2-methyl-1-[4-(trifluoromethyl)benzyl]tryptophan | 46 and 47 | 2-methylindole | 4-trifluoromethylbenzyl bromide |

-continued

| Example | Compound Name | Prepared by using same synthetic procedures of Example # | SM1 (indole or tryptophan) | SM2 (alkyl halide, N/A = not applicable) |
|---|---|---|---|---|
| 151 | N-{[4-(but-2-ynyloxy)phenyl]sulfonyl}-2-methyl-1-[4-(trifluoromethoxy)benzyl]tryptophan | 46 and 47 | 2-methylindole | 4-trifluoromethoxybenzyl bromide |
| 152 | N-{[4-(but-2-ynyloxy)phenyl]sulfonyl}-1-(2-fluorobenzyl)-2-methyltryptophan | 46 and 47 | 2-methylindole | 2-fluorobenzyl bromide |
| 153 | N-{[4-(but-2-ynyloxy)phenyl]sulfonyl}-1-(3-fluorobenzyl)-2-methyltryptophan | 46 and 47 | 2-methylindole | 3-fluorobenzyl bromide |
| 154 | N-{[4-(but-2-ynyloxy)phenyl]sulfonyl}-1-(4-fluorobenzyl)-2-methyltryptophan | 46 and 47 | 2-methylindole | 4-fluorobenzyl bromide |
| 155 | N-{[4-(but-2-ynyloxy)phenyl]sulfonyl}-1-(3,5-difluorobenzyl)-2-methyltryptophan | 46 and 47 | 2-methylindole | 3,5-difluorobenzyl bromide |
| 156 | N-{[4-(but-2-ynyloxy)phenyl]sulfonyl}-1-(4-chlorobenzyl)-2-methyltryptophan | 46 and 47 | 2-methylindole | 4-chlorobenzyl bromide |
| 157 | N-{[4-(but-2-ynyloxy)phenyl]sulfonyl}-1-(4-isopropylbenzyl)-2-methyltryptophan | 46 and 47 | 2-methylindole | 4-isopropylbenzyl bromide |
| 158 | N-{[4-(but-2-ynyloxy)phenyl]sulfonyl}-1-(2-cyanobenzyl)-2-methyltryptophan | 46 and 47 | 2-methylindole | 2-cyanobenzyl bromide |
| 159 | N-{[4-(but-2-ynyloxy)phenyl]sulfonyl}-1-(3-cyanobenzyl)-2-methyltryptophan | 46 and 47 | 2-methylindole | 3-cyanobenzyl bromide |
| 160 | N-{[4-(but-2-ynyloxy)phenyl]sulfonyl}-1-(4-cyanobenzyl)-2-methyltryptophan | 46 and 47 | 2-methylindole | 4-cyanobenzyl bromide |
| 161 | 1-(1,3-benzodioxol-5-ylmethyl)-N-{[4-(but-2-ynyloxy)phenyl]sulfonyl}-2-methyltryptophan | 46 and 47 | 2-methylindole | 5-bromomethyl-benzo[1,3]dioxole |
| 162 | N-{[4-(but-2-ynyloxy)phenyl]sulfonyl}-2-methyl-1-(pyridin-3-ylmethyl)tryptophan | 46 and 47 | 2-methylindole | 3-bromomethyl-pyridine |
| 163 | N-{[4-(but-2-ynyloxy)phenyl]sulfonyl}-1-ethyl-2-methyltryptophan | 46 and 47 | 2-methylindole | ethyl bromide |
| 164 | N-{[4-(but-2-ynyloxy)phenyl]sulfonyl}-1-isobutyl-2-methyltryptophan | 46 and 47 | 2-methylindole | 2-methylpropyl bromide |
| 165 | N-{[4-(but-2-ynyloxy)phenyl]sulfonyl}-1-(cyclobutylmethyl)-2-methyltryptophan | 46 and 47 | 2-methylindole | bromomethyl-cyclobutane |
| 166 | N-{[4-(but-2-ynyloxy)phenyl]sulfonyl}-1-(cyclohexylmethyl)-2-methyltryptophan | 46 and 47 | 2-methylindole | bromomethyl-cyclohexane |
| 167 | 1-benzyl-N-{[4-(but-2-ynyloxy)phenyl]sulfonyl}-5-methyltryptophan | 46 and 47 | 5-methylindole | benzyl bromide |
| 168 | N-{[4-(but-2-ynyloxy)phenyl]sulfonyl}-5-methyl-1-(2-methylbenzyl)tryptophan | 46 and 47 | 5-methylindole | 2-methylbenzyl bromide |

| Example | Compound Name | Prepared by using same synthetic procedures of Example # | SM1 (indole or tryptophan) | SM2 (alkyl halide, N/A = not applicable) |
|---|---|---|---|---|
| 169 | N-{[4-(but-2-ynyloxy)phenyl]sulfonyl}-5-methyl-1-(3-methylbenzyl)tryptophan | 46 and 47 | 5-methylindole | 3-metrhylbenzyl bromide |
| 170 | N-{[4-(but-2-ynyloxy)phenyl]sulfonyl}-1-(2-methoxybenzyl)-5-methyltryptophan | 46 and 47 | 5-methylindole | 2-methoxybenzyl bromide |
| 171 | N-{[4-(but-2-ynyloxy)phenyl]sulfonyl}-1-(3-methoxybenzyl)-5-methyltryptophan | 46 and 47 | 5-methylindole | 3-methoxybenzyl bromide |
| 172 | N-{[4-(but-2-ynyloxy)phenyl]sulfonyl}-5-methyl-1-[2-(trifluoromethyl)benzyl]tryptophan | 46 and 47 | 5-methylindole | 2-trifluoromethyl benzyl bromide |
| 173 | N-{[4-(but-2-ynyloxy)phenyl]sulfonyl}-5-methyl-1-[3-(trifluoromethyl)benzyl]tryptophan | 46 and 47 | 5-methylindole | 3-trifluoromethyl benzyl bromide |
| 174 | N-{[4-(but-2-ynyloxy)phenyl]sulfonyl}-5-methyl-1-[4-(trifluoromethyl)benzyl]tryptophan | 46 and 47 | 5-methylindole | 4-trifluoromethyl benzyl bromide |
| 175 | N-{[4-(but-2-ynyloxy)phenyl]sulfonyl}-1-(3-fluorobenzyl)-5-methyltryptophan | 46 and 47 | 5-methylindole | 3-fluorobenzyl bromide |
| 176 | N-{[4-(but-2-ynyloxy)phenyl]sulfonyl}-1-(4-fluorobenzyl)-5-methyltryptophan | 46 and 47 | 5-methylindole | 4-fluorobenzyl bromide |
| 177 | N-{[4-(but-2-ynyloxy)phenyl]sulfonyl}-1-(3,5-difluorobenzyl)-5-methyltryptophan | 46 and 47 | 5-methylindole | 3,5-difluorobenzyl bromide |
| 178 | N-{[4-(but-2-ynyloxy)phenyl]sulfonyl}-1-(4-chlorobenzyl)-5-methyltryptophan | 46 and 47 | 5-methylindole | 4-chlorobenzyl bromide |
| 179 | N-{[4-(but-2-ynyloxy)phenyl]sulfonyl}-1-(4-isopropylbenzyl)-5-methyltryptophan | 46 and 47 | 5-methylindole | 4-isopropylbenzyl bromide |
| 180 | 1-(1,3-benzodioxol-5-ylmethyl)-N-{[4-(but-2-ynyloxy)phenyl]sulfonyl}-5-methyltryptophan | 46 and 47 | 5-methylindole | 5-bromomethyl-benzo[1,3]dioxole |
| 181 | N-{[4-(but-2-ynyloxy)phenyl]sulfonyl}-5-methyl-1-(pyridin-3-ylmethyl)tryptophan | 46 and 47 | 5-methylindole | 3-bromomethyl-pyridine |
| 182 | N-{[4-(but-2-ynyloxy)phenyl]sulfonyl}-1-ethyl-5-methyltryptophan | 46 and 47 | 5-methylindole | ethyl bromide |
| 183 | N-{[4-(but-2-ynyloxy)phenyl]sulfonyl}-1-isobutyl-5-methyltryptophan | 46 and 47 | 5-methylindole | 2-methylpropyl bromide |
| 184 | N-{[4-(but-2-ynyloxy)phenyl]sulfonyl}-5-methyl-1-pentyltryptophan | 46 and 47 | 5-methylindole | 1-bromo-pentane |
| 185 | 1-benzyl-N-{[4-(but-2-ynyloxy)phenyl]sulfonyl}-5-methoxy-2-methyltryptophan | 46 and 47 | 5-methoxy-2-methylindole | benzyl bromide |
| 186 | N-{[4-(but-2-ynyloxy)phenyl]sulfonyl}-5-methoxy-2-methyl-1-(2-methylbenzyl)tryptophan | 46 and 47 | 5-methoxy-2-methylindole | 2-methylbenzyl bromide |

-continued

| Example | Compound Name | Prepared by using same synthetic procedures of Example # | SM1 (indole or tryptophan) | SM2 (alkyl halide, N/A = not applicable) |
|---|---|---|---|---|
| 187 | N-{[4-(but-2-ynyloxy)phenyl]sulfonyl}-5-methoxy-2-methyl-1-(3-methylbenzyl)tryptophan | 46 and 47 | 5-methoxy-2-methylindole | 3-methylbenzyl bromide |
| 188 | N-{[4-(but-2-ynyloxy)phenyl]sulfonyl}-5-methoxy-2-methyl-1-(4-methylbenzyl)tryptophan | 46 and 47 | 5-methoxy-2-methylindole | 4-methylbenzyl bromide |
| 189 | N-{[4-(but-2-ynyloxy)phenyl]sulfonyl}-5-methoxy-1-(2-methoxybenzyl)-2-methyltryptophan | 46 and 47 | 5-methoxy-2-methylindole | 2-methoxybenzyl bromide |
| 190 | N-{[4-(but-2-ynyloxy)phenyl]sulfonyl}-5-methoxy-1-(3-methoxybenzyl)-2-methyltryptophan | 46 and 47 | 5-methoxy-2-methylindole | 3-methoxybenzyl bromide |
| 191 | N-{[4-(but-2-ynyloxy)phenyl]sulfonyl}-5-methoxy-1-(4-methoxybenzyl)-2-methyltryptophan | 46 and 47 | 5-methoxy-2-methylindole | 4-methoxybenzyl bromide |
| 192 | N-{[4-(but-2-ynyloxy)phenyl]sulfonyl}-1-(3,5-dimethoxybenzyl)-5-methoxy-2-methyltryptophan | 46 and 47 | 5-methoxy-2-methylindole | 3,5-dimethoxy benzyl bromide |
| 193 | N-{[4-(but-2-ynyloxy)phenyl]sulfonyl}-5-methoxy-2-methyl-1-[2-(trifluoromethyl)benzyl]tryptophan | 46 and 47 | 5-methoxy-2-methylindole | 2-trifluoromethyl benzyl bromide |
| 194 | N-{[4-(but-2-ynyloxy)phenyl]sulfonyl}-5-methoxy-2-methyl-1-[3-(trifluoromethoxy)benzyl]tryptophan | 46 and 47 | 5-methoxy-2-methylindole | 3-trifluoromethoxy benzyl bromide |
| 195 | N-{[4-(but-2-ynyloxy)phenyl]sulfonyl}-5-methoxy-2-methyl-1-[4-(trifluoromethyl)benzyl]tryptophan | 46 and 47 | 5-methoxy-2-methylindole | 4-trifluoromethyl benzyl bromide |
| 196 | N-{[4-(but-2-ynyloxy)phenyl]sulfonyl}-5-methoxy-2-methyl-1-[4-(trifluoromethoxy)benzyl]tryptophan | 46 and 47 | 5-methoxy-2-methylindole | 4-trifluoromethoxy benzyl bromide |
| 197 | N-{[4-(but-2-ynyloxy)phenyl]sulfonyl}-1-(2-fluorobenzyl)-5-methoxy-2-methyltryptophan | 46 and 47 | 5-methoxy-2-methylindole | 2-fluorobenzyl bromide |
| 198 | N-{[4-(but-2-ynyloxy)phenyl]sulfonyl}-1-(3-fluorobenzyl)-5-methoxy-2-methyltryptophan | 46 and 47 | 5-methoxy-2-methylindole | 3-fluorobenzyl bromide |
| 199 | N-{[4-(but-2-ynyloxy)phenyl]sulfonyl}-1-(4-fluorobenzyl)-5-methoxy-2-methyltryptophan | 46 and 47 | 5-methoxy-2-methylindole | 4-fluorobenzyl bromide |
| 200 | N-{[4-(but-2-ynyloxy)phenyl]sulfonyl}-1-(3,5-difluorobenzyl)-5-methoxy-2-methyltryptophan | 46 and 47 | 5-methoxy-2-methylindole | 3,5-difluorobenzyl bromide |
| 201 | N-{[4-(but-2-ynyloxy)phenyl]sulfonyl}-1-(4-chlorobenzyl)-5-methoxy-2-methyltryptophan | 46 and 47 | 5-methoxy-2-methylindole | 4-chlorobenzyl bromide |

| Example | Compound Name | Prepared by using same synthetic procedures of Example # | SM1 (indole or tryptophan) | SM2 (alkyl halide, N/A = not applicable) |
|---|---|---|---|---|
| 202 | N-{[4-(but-2-ynyloxy)phenyl]sulfonyl}-1-(4-isopropylbenzyl)-5-methoxy-2-methyltryptophan | 46 and 47 | 5-methoxy-2-methylindole | 4-isopropylbenzyl bromide |
| 203 | N-{[4-(but-2-ynyloxy)phenyl]sulfonyl}-1-(2-cyanobenzyl)-5-methoxy-2-methyltryptophan | 46 and 47 | 5-methoxy-2-methylindole | 2-cyanobenzyl bromide |
| 204 | N-{[4-(but-2-ynyloxy)phenyl]sulfonyl}-1-(3-cyanobenzyl)-5-methoxy-2-methyltryptophan | 46 and 47 | 5-methoxy-2-methylindole | 3-cyanobenzyl bromide |
| 205 | N-{[4-(but-2-ynyloxy)phenyl]sulfonyl}-1-(4-cyanobenzyl)-5-methoxy-2-methyltryptophan | 46 and 47 | 5-methoxy-2-methylindole | 4-cyanobenzyl bromide |
| 206 | 1-(1,3-benzodioxol-5-ylmethyl)-N-{[4-(but-2-ynyloxy)phenyl]sulfonyl}-5-methoxy-2-methyltryptophan | 46 and 47 | 5-methoxy-2-methylindole | 5-bromomethyl-benzo[1,3]dioxole |
| 207 | N-{[4-(but-2-ynyloxy)phenyl]sulfonyl}-1-(4-carboxybenzyl)-5-methoxy-2-methyltryptophan | 46 and 47 | 5-methoxy-2-methylindole | 4-bromomethyl-benzoic acid |
| 208 | N-{[4-(but-2-ynyloxy)phenyl]sulfonyl}-5-methoxy-1,2-dimethyltryptophan | 46 and 47 | 5-methoxy-2-methylindole | iodomethane |
| 209 | N-{[4-(but-2-ynyloxy)phenyl]sulfonyl}-1-ethyl-5-methoxy-2-methyltryptophan | 46 and 47 | 5-methoxy-2-methylindole | iodoethane |
| 210 | N-{[4-(but-2-ynyloxy)phenyl]sulfonyl}-1-isobutyl-5-methoxy-2-methyltryptophan | 46 and 47 | 5-methoxy-2-methylindole | 2-methylpropyl bromide |
| 211 | N-{[4-(but-2-ynyloxy)phenyl]sulfonyl}-5-methoxy-2-methyl-1-pentyltryptophan | 46 and 47 | 5-methoxy-2-methylindole | 1-bromo-pentane |
| 212 | N-{[4-(but-2-ynyloxy)phenyl]sulfonyl}-1-(cyclobutylmethyl)-5-methoxy-2-methyltryptophan | 46 and 47 | 5-methoxy-2-methylindole | bromomethyl-cyclobutane |
| 213 | N-{[4-(but-2-ynyloxy)phenyl]sulfonyl}-1-(cyclohexylmethyl)-5-methoxy-2-methyltryptophan | 46 and 47 | 5-methoxy-2-methylindole | bromomethyl-cyclohexane |
| 214 | N-{[4-(but-2-ynyloxy)phenyl]sulfonyl}-1-(4-hydroxybenzyl)-D-tryptophan | 6 (step 1) and 7 | indole | p-hydroxybenzyl bromide |
| 215 | N-{[4-(but-2-ynyloxy)phenyl]sulfonyl}-1-(4-ethoxybenzyl)-D-tryptophan | 6 (step 1) and 7 | indole | p-ethoxybenzyl bromide |
| 216 | 1-[4-(allyloxy)benzyl]-N-{[4-(but-2-ynyloxy)phenyl]sulfonyl}-D-tryptophan | 6 (step 1) and 7 | indole | p-allylbenzyl bromide |
| 217 | N-{[4-(but-2-ynyloxy)phenyl]sulfonyl}-5-methyl-D(or L)-tryptophan | 6 (step 2) | 5-methyl tryptophan | N/A |

-continued

| Example | Compound Name | Prepared by using same synthetic procedures of Example # | SM1 (indole or tryptophan) | SM2 (alkyl halide, N/A = not applicable) |
|---|---|---|---|---|
| 218 | N-{[4-(but-2-ynyloxy)phenyl]sulfonyl}-5-methyl-L(or D)-tryptophan | 6 (step 2) | 5-methyl tryptophan | N/A |
| 219 | 1-(tert-butoxycarbonyl)-N-{[4-(but-2-ynyloxy)phenyl]sulfonyl}-L-tryptophan | 6 (step 1) | 1-tert-butoxy carbonyl-L-tryptophan | N/A |
| 220 | 1-(tert-butoxycarbonyl)-N-{[4-(but-2-ynyloxy)phenyl]sulfonyl}-D-tryptophan | 6 (step 1) | 1-tert-butoxy carbonyl-D-tryptophan | N/A |
| 221 | N-{[4-(but-2-ynyloxy)phenyl]sulfonyl}-5-methoxy-D(or L)-tryptophan | 4 (step 2) | 5-methoxy tryptophan | N/A |
| 222 | N-{[4-(but-2-ynyloxy)phenyl]sulfonyl}-methoxy-L(or D)-tryptophan | 4 (step 2) | 5-methoxy tryptophan | N/A |
| 223 | 5-(benzyloxy)-N-{[4-(but-2-ynyloxy)phenyl]sulfonyl}-D(or L)-tryptophan | 20 (step 2) | 5-benzyloxy-tryptophan | N/A |
| 224 | 5-(benzyloxy)-N-{[4-(but-2-ynyloxy)phenyl]sulfonyl}-L(or D)-tryptophan | 20 (step 2) | 5-benzyloxy-tryptophan | N/A |

Determination of Activity

Standard pharmacological test procedures are readily available to determine the ability of compounds of the invention to inhibit TACE. Generally, TACE inhibition is determined by the ability to inhibit TACE mediated cleavage of a TNF-α precursor (pro-TNF protein), or a TACE substrate (such as pro-TNF peptide) that contains the same scissile amide bond as that of the TNF-α precursor. The inhibition is generally reported as the percentage of inhibition of the cleavage of the TNF-α precursor (or a TACE substrate), or as the $IC_{50}$ (the concentration required for 50% inhibition). Some exemplary standard pharmacological test procedures for TACE inhibition are provided in (a) Jin, G., et al. (2002) *Analytical Biochemistry* 302: 269-275; (b) Newton, R C, et al. (2001) *Ann Rheum Dis*. 60: iii25-iii32; and (c) Knight, C. G., et al. *FEBS Lett*. (1992) 296: 263-266, each of which is hereby incorporated by reference in its entirety.

Biological Assays of Compounds of the Invention

TACE FRET Assay Using TACE Cat

The procedure is essentially as described in Jin, G. et al., *Analytical Biochemistry* (2002) 302: 269-275, incorporated by reference herein in its entirety. The basic measurement of the assay is the percentage of inhibition of the cleavage of the fluorogenic pro-TNF peptide by TACE or the $IC_{50}$ determination by a fitting with the model-39 of LSW data analysis tool, which processes data according to the equation $y=((B*K^n)+(100*x^n))/(K^n+x^n)$, a sigmoidal curve with Hill slope, B to 100. "K" is the $IC_{50}$. Generally, "n" and "B" are floated, noting that n (Hill slope) should be close to 1 and B (background offset) to 0.

Pro-TNF-α substrate peptide Abz-LAQAVRSSSR-Dpa (AnaSpec, San Jose, Calif., WARC-1) was prepared as a 2 mM stock solution in the TACE assay buffer (50 mM Tris-HCl, pH 7.4, 25 mM NaCl, 4% Glycerol, 0.005% Brij 35).

The catalytic domain of the recombinant TACE protein was expressed and purified. The TACE protein (1 ug/ml) was pretreated with the inhibitors at various concentrations for 10 min. at room temperature. The reaction was initiated by the addition of the substrate peptide. The increase in fluorescence was monitored at an Excitation of 320 nM and an Emission of 420 nM over a period of 10 min. The initial rate (slope) of the reaction was determined using a fluorescence plate reader (Molecular Devices, Spectra Max Gemini XS).

Compounds with $IC_{50}$ or % inhibition at 1 µM in TACE FRET assay are shown in the following Table 1.

TABLE 1

TACE FRET assay

| Example | Conc. (µM) | TACE Inhibition (%) | TACE $IC_{50}$ (µM) |
|---|---|---|---|
| 35 | | | 0.08 |
| 218 | | | 0.14 |
| 221 | | | 0.14 |
| 91 | | | 0.19 |
| 185 | | | 0.20 |
| 190 | | | 0.26 |
| 188 | | | 0.27 |
| 186 | | | 0.28 |
| 6 | | | 0.28 |
| 201 | | | 0.29 |
| 197 | | | 0.30 |
| 199 | | | 0.32 |
| 198 | | | 0.34 |
| 4 | | | 0.36 |
| 206 | | | 0.36 |
| 224 | | | 0.37 |
| 193 | | | 0.45 |
| 205 | | | 0.47 |
| 204 | | | 0.48 |
| 216 | | | 0.54 |
| 20 | | | 0.75 |

TABLE 1-continued

TACE FRET assay

| Example | Conc. (µM) | TACE Inhibition (%) | TACE IC$_{50}$ (µM) |
|---|---|---|---|
| 27 | | | 0.97 |
| 36 | | | 0.98 |
| 19 | | | 1.19 |
| 69 | | | 1.19 |
| 67 | | | 1.23 |
| 24 | | | 1.25 |
| 68 | | | 1.32 |
| 21 | | | 1.40 |
| 65 | | | 1.50 |
| 3 | | | 1.56 |
| 8 | | | 1.57 |
| 5 | | | 1.61 |
| 23 | | | 1.71 |
| 70 | | | 1.87 |
| 28 | | | 1.90 |
| 56 | | | 2.07 |
| 25 | | | 2.15 |
| 58 | | | 2.24 |
| 52 | | | 2.24 |
| 40 | | | 2.30 |
| 22 | | | 2.31 |
| 1 | | | 2.53 |
| 7 | | | 2.96 |
| 42 | | | 3.45 |
| 26 | | | 3.59 |
| 220 | | | 3.67 |
| 45 | | | 4.04 |
| 41 | | | 4.40 |
| 223 | | | 6.98 |
| 2 | | | 8.20 |
| 222 | | | 10.11 |
| 194 | 1 | 80.79 | |
| 200 | 1 | 80.51 | |
| 192 | 1 | 79.96 | |
| 187 | 1 | 78.82 | |
| 195 | 1 | 78.26 | |
| 191 | 1 | 77.47 | |
| 189 | 1 | 75.58 | |
| 133 | 1 | 73.86 | |
| 196 | 1 | 72.82 | |
| 211 | 1 | 72.24 | |
| 158 | 1 | 72.13 | |
| 209 | 1 | 69.80 | |
| 215 | 1 | 69.46 | |
| 101 | 1 | 68.50 | |
| 202 | 1 | 66.99 | |
| 210 | 1 | 66.62 | |
| 90 | 1 | 65.20 | |
| 134 | 1 | 64.21 | |
| 92 | 1 | 63.95 | |
| 95 | 1 | 63.58 | |
| 88 | 1 | 62.83 | |
| 207 | 1 | 62.08 | |
| 208 | 1 | 61.79 | |
| 98 | 1 | 60.95 | |
| 213 | 1 | 60.49 | |
| 212 | 1 | 59.50 | |
| 136 | 1 | 57.82 | |
| 102 | 1 | 56.94 | |
| 203 | 1 | 56.75 | |
| 96 | 1 | 56.49 | |
| 153 | 1 | 55.87 | |
| 100 | 1 | 55.64 | |
| 155 | 1 | 54.33 | |
| 93 | 1 | 53.77 | |
| 89 | 1 | 53.59 | |
| 154 | 1 | 52.70 | |
| 152 | 1 | 51.70 | |
| 149 | 1 | 50.47 | |
| 145 | 1 | 49.53 | |
| 94 | 1 | 47.36 | |
| 59 | 1 | 44.39 | |
| 148 | 1 | 44.08 | |
| 60 | 1 | 43.49 | |
| 156 | 1 | 43.30 | |
| 64 | 1 | 40.87 | |
| 61 | 1 | 39.52 | |
| 62 | 1 | 39.33 | |
| 49 | 1 | 38.85 | |
| 51 | 1 | 38.28 | |
| 54 | 1 | 37.95 | |
| 87 | 1 | 37.44 | |
| 48 | 1 | 37.24 | |
| 146 | 1 | 35.89 | |
| 150 | 1 | 35.64 | |
| 147 | 1 | 35.59 | |
| 157 | 1 | 34.24 | |
| 85 | 1 | 32.94 | |
| 143 | 1 | 32.39 | |
| 57 | 1 | 32.13 | |
| 55 | 1 | 31.34 | |
| 83 | 1 | 31.07 | |
| 50 | 1 | 30.59 | |
| 53 | 1 | 30.58 | |
| 77 | 1 | 29.75 | |
| 135 | 1 | 29.60 | |
| 141 | 1 | 29.59 | |
| 138 | 1 | 29.41 | |
| 63 | 1 | 28.18 | |
| 73 | 1 | 28.03 | |
| 72 | 1 | 27.48 | |
| 80 | 1 | 27.12 | |
| 139 | 1 | 25.08 | |
| 75 | 1 | 24.97 | |
| 151 | 1 | 24.34 | |
| 97 | 1 | 21.90 | |
| 144 | 1 | 18.84 | |
| 76 | 1 | 18.32 | |
| 140 | 1 | 15.98 | |
| 86 | 1 | 15.71 | |
| 74 | 1 | 15.04 | |
| 121 | 1 | 14.75 | |
| 81 | 1 | 13.92 | |
| 137 | 1 | 12.10 | |
| 119 | 1 | 11.73 | |
| 105 | 1 | 11.00 | |
| 117 | 1 | 10.89 | |
| 111 | 1 | 10.74 | |
| 114 | 1 | 10.35 | |
| 124 | 1 | 10.17 | |
| 120 | 1 | 10.02 | |
| 108 | 1 | 9.93 | |
| 116 | 1 | 9.72 | |
| 132 | 1 | 9.55 | |
| 214 | 1 | 8.77 | |
| 126 | 1 | 8.36 | |
| 142 | 1 | 8.34 | |
| 79 | 1 | 8.27 | |
| 110 | 1 | 8.02 | |
| 109 | 1 | 7.93 | |
| 78 | 1 | 7.39 | |
| 107 | 1 | 7.34 | |
| 125 | 1 | 6.23 | |
| 103 | 1 | 6.16 | |
| 118 | 1 | 5.98 | |
| 104 | 1 | 5.79 | |
| 106 | 1 | 5.53 | |
| 112 | 1 | 5.51 | |
| 82 | 1 | 5.26 | |
| 115 | 1 | 4.29 | |
| 122 | 1 | −0.34 | |
| 128 | 1 | −0.60 | |
| 71 | 1 | −1.19 | |
| 131 | 1 | −1.21 | |
| 113 | 1 | −2.04 | |
| 123 | 1 | −2.56 | |

TABLE 1-continued

TACE FRET assay

| Example | Conc. (μM) | TACE Inhibition (%) | TACE IC$_{50}$ (μM) |
|---|---|---|---|
| 127 | 1 | −3.22 | |
| 129 | 1 | −4.96 | |
| 130 | 1 | −5.71 | |

Human Whole Blood Assay for LPS-Induced TNF-A Secretion

The procedure is essentially as described in Newton, R. C., et al., (2001) *Ann Rheum Dis.* 60, iii25-iii32, incorporated by reference herein in its entirety. The basic measurement of the assay is the percentage of inhibition of TNF-α secretion and the IC$_{50}$ determination by a fitting with the model-39 of LSW data analysis tool.

Three hundred fifty microliters (350 μl) of fresh human blood drawn from healthy volunteers were pre-incubated with compounds for one hour at the various concentrations at 37° C. with turning. Generally, the final DMSO concentrations should be kept below 0.2%. At the end of the incubation, LPS (Sigma, L2262) was added to the blood at 100 ng/ml and the samples were further incubated for 4 hours or overnight at 37° C. with constant rotation. At the end of the incubation period, 650 μl of serum-free medium was added to the blood samples and the samples were centrifuged at 1500 rpm for 15 minutes. Five hundred microliters (500 μl) of supernate were collected and frozen at −80° C.

The TNF-α and other proinflammatory cytokines were detected by ELISA assay according to the manufacturer's instruction (Biosource International, Inc., Camarillo, Calif.). Table 2 shows the results for a compound of the invention.

TABLE 2

TNF-α Secretion in Human Whole Blood

| Example | IC$_{50}$ (μM) |
|---|---|
| 218 | >50 |

Cell-Based Assay for Inhibition of TNF-A Secretion in Raw Cells

The basic measurement of the assay is the percentage of inhibition of TNF-α secretion and the IC$_{50}$ determination by a fitting with the model-39 of LSW data analysis tool.

Raw 264.7 cells (ATCC Cat No. TIB-71) are maintained in DMEM medium containing 10% of serum, P/S, and Glutamine. Cells are split twice a week by scraping and 1 to 10 or 20 dilutions. For testing compounds, cells are cultured to confluence and are seeded the day before the experiment in 24 well culture dishes at 0.5 to 1 million/ml/well. On the next morning, the medium from the overnight culture is replaced with the fresh growth medium. The compounds are added at various concentrations at the 0.2% of final DMSO concentrations (10 μl of a 20% DMSO solution containing testing compounds is added to each well). The cells are pre-incubated with compounds for 1 hour. LPS (Sigma, L2262) is added to cells at a final concentration of 100 ng/ml (10 μl of a 10 μM LPS solution freshly diluted from a 1 mg/ml LPS stock solution in PBS is added to each well) and cells are further incubated for 4 hours at 37° C. One milliliter (1 ml) of the supernatant was collected, cells are spun down and the supernatants are frozen at −80° C. until use.

The TNF-α and other proinflammatory cytokines were detected by ELISA assay according to the manufacturer's instruction (Biosource International, Inc., Camarillo, Calif.) (For IL-1b measurement in Raw cells, one round of freeze and thaw of the cells was required.)

Results for representative compounds of the invention are shown in Table 3.

TABLE 3

TNF-α Secretion in Raw Cells

| Example | Conc. Lo (μM) | Conc. Hi (μM) | IC$_{50}$ (μM) |
|---|---|---|---|
| 24 | | | >60 |
| 27 | | | >60 |
| 35 | | | >60 |
| 199 | 0.016 | 40 | >60 |
| 218 | | | 7.11 |
| 221 | | | 57 |

In-Vitro Fluorescence Assay of MMP-1 Activity

A continuous assay was used in which the substrate is a synthetic peptide containing a fluorescent group (7-methoxy-coumarin; Mca) that is quenched by energy transfer to a 2,4-dinitrophenyl group. See Knight, C. G. et al., *FEBS Lett.* (1992) 296: 263-266, incorporated herein by reference in its entirety. When the peptide was cleaved by MMP, a large increase in fluorescence was observed. The source of enzyme in the assay was the recombinant human catalytic domain of MMP-1. See Zhang, Y et al., *Journal of Pharmacology and Experimental Therapeutics (JPET)* (2004) 309:348-355, incorporated by reference in its entirety. The substrate used was Mca-PQGL-(3-[2,4-dinitrophenyl]-L-2,3-diaminopropionyl)-AR-OH (denoted as Wammp-5, custom synthesized by AnaSpec, Inc., San Jose, Calif.). The assay buffer consisted of 50 mM Hepes (pH 7.4), 100 mM NaCl, 5 mM CaCl$_2$, and 0.005% Brij-35. Each well of black polystyrene 96-well plates contained a 200 μl reaction mixture consisting of assay buffer, purified MMP (final concentration of 25 ng/ml, prepared by diluting with the assay buffer), and varied concentrations of inhibitor (prepared by serially diluting a given inhibitor in DMSO in 96-well polypropylene plate). The plates were then incubated at 30° C. for 15 minutes. The enzymatic reactions were initiated by adding the substrate to a final concentration of 20 μM, and mixing 10 times with a pipette. The final DMSO concentration in the assay was 6.0%. The initial rate of the cleavage reaction was determined at 30° C. with a fluorescence plate reader (excitation filter of 330 nm and emission filter of 395 nm) immediately after substrate addition.

Plots of the inhibitor concentration versus the percent inhibition were fit to the following equation: $y=(a-d)/[1+(x/c)^b]+d$, a general sigmoidal curve with Hill slope, a to d. x is the inhibitor concentration under test. "y" is the percent inhibition. "a" is the limiting response as x approaches zero. As x increases without bound, y tends toward its limit d. "c" is the inflection point (IC$_{50}$) for the curve. That is, y is halfway between the lower and upper asymptotes when x=c. "b" is the slope factor or Hill coefficient.

Results for representative compounds of the invention are shown in Table 4.

TABLE 4

MMP-1 FRET Assay

| Example | Conc. (μM) | MMP-1 Inhibition (%) |
|---|---|---|
| 218 | 160 | 30 |
| 4 | 1000 | 33 |
| 35 | 33 | 14 |
| 47 | 67 | 30 |
| 221 | 83 | 9 |
| 224 | 83 | 19 |

In-Vitro Fluorescence Assay of MMP-13 Activity

The procedure is essentially the same as for the in-vitro fluorescence assay of MMP-1 activity, except that the source of enzyme in the assay was the recombinant human catalytic domain of MMP-13 (165 amino acids, residues 104-268, 19 kDa). See Zhang, Y et al., *Journal of Pharmacology and Experimental Therapeutics* (*JPET*) (2004) 309:348-355, incorporated by reference in its entirety.

Results for representative compounds of the invention are shown in Table 5.

TABLE 5

MMP-13 FRET Assay

| Example | Conc. (μM) | MMP-13 Inhibition (%) | MMP-13 $IC_{50}$ (μM) |
|---|---|---|---|
| 4 | 15 | 50 | |
| 6 | | | 6.87 |
| 20 | | | 15.3 |
| 28 | | | 17 |
| 35 | | | 4.56 |
| 218 | | | 1.81 |
| 47 | 3 | 50 | |
| 221 | | | 13.6 |
| 224 | | | 4.44 |

In-Vitro Fluorescence Assay of MMP-14 Activity

The procedure is essentially the same as for the in-vitro fluorescence assay of MMP-1 activity, except that the source of enzyme in the assay was the recombinant human catalytic domain of MMP-14 (177 amino acids corresponding to Tyr89-Gly265 of mature human enzyme; 20 kDa) purchased from Chemicon International, Inc. (Temecula, Calif.; catalog number CC1041).

Results for representative compounds of the invention are shown in Table 6.

TABLE 6

MMP-14 FRET Assay

| Example | MMP-14 $IC_{50}$ (μM) |
|---|---|
| 218 | 6.82 |
| 4 | 22.7 |
| 35 | 13 |
| 47 | 11.6 |
| 221 | 20.7 |
| 224 | 19.7 |

In-Vitro Fluorescence Assay of MMP-2 Activity

The procedure is essentially the same as for the in-vitro fluorescence assay of MMP-1 activity, except that the source of enzyme in the assay was the recombinant human MMP-2 (66 kDa) purchased from Oncogene Research Products (catalog number PF023 from Calbiochem, San Diego, Calif.).

Results for representative compounds of the invention are shown in Table 7.

TABLE 7

MMP-2 FRET Assay

| Example | MMP-2 $IC_{50}$ (μM) |
|---|---|
| 4 | 7.84 |
| 6 | 1.16 |
| 20 | 7.85 |
| 28 | 3.97 |
| 35 | 1.44 |
| 218 | 0.27 |
| 47 | 0.66 |
| 221 | 1.27 |
| 224 | 2.45 |

It is intended that each of the patents, applications, and printed publications, including books, mentioned herein be hereby incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A compound of the Formula I:

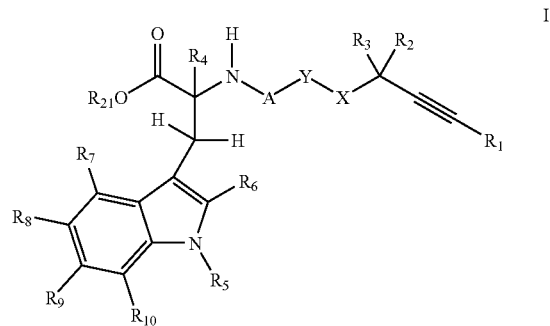

wherein:

$R_1$ is H, aryl, $C_{1-8}$ alkyl, $C_{2-8}$ alkenyl, $C_{2-8}$ alkynyl, $C_{3-8}$ cycloalkyl, aralkyl, heteroalkyl, halogen, hydroxyalkyl, alkoxy, alkenyloxy, alkynyloxy, perfluoroalkoxy, or alkoxy-alkyl; wherein each of said aryl, $C_{1-8}$ alkyl, $C_{2-8}$ alkenyl, $C_{2-8}$ alkynyl, $C_{3-8}$ cycloalkyl or aralkyl is optionally substituted with up to four independently selected $R_{14}$ groups;

$R_2$, $R_3$ and $R_4$ are each, independently, H, $C_{1-8}$ alkyl, halogen, CN, CCH, OH, or $OR_1$;

$R_5$, $R_6$, $R_7$, $R_8$, $R_9$ and $R_{10}$ are each, independently, H, aryl, $C_{1-8}$ alkyl, $C_{2-8}$ alkenyl, $C_{2-8}$ alkynyl, $C_{3-8}$ cycloalkyl, aralkyl, heteroalkyl, halogen, CN, hydroxyalkyl, alkoxy, alkenyloxy, alkynyloxy, perfluoroalkoxy, alkoxy-alkyl, $NR_{11}R_{11}$, $COOR_{11}$, or $OR_{11}$;

wherein each of said aryl, heteroalkyl, $C_{1-8}$ alkyl, $C_{2-8}$ alkenyl, $C_{2-8}$ alkynyl, $C_{3-8}$ cycloalkyl, or aralkyl is optionally substituted with up to four independently selected $R_{15}$ groups;

wherein one or more than one of the pairs $R_4$ and $R_6$, $R_4$ and $R_7$, $R_5$ and $R_6$, $R_5$ and $R_{10}$, $R_7$ and $R_8$, $R_8$ and $R_9$ or $R_9$ and $R_{10}$, together with the carbon atom or atoms to which they attached, can form a cycloalkyl ring having 3-8 carbon atoms;

$R_{11}$ is H, aryl, aralkyl, $C_{1-8}$ alkyl, $C_{3-8}$ cycloalkyl, halogen, hydroxyalkyl, alkoxy-alkyl, $C_{1-8}$ alkanoyl, $COOR_1$, $COR_1$, $SO_2$—$C_{1-8}$ alkyl, $SO_2$-aryl, or CO—$NHR_1$;

wherein each of said aryl, aralkyl, $C_{1-8}$ alkyl, $C_{3-8}$ cycloalkyl, $SO_2$—$C_{1-8}$ alkyl, and $SO_2$-aryl is optionally substituted with up to four independently selected $R_{16}$ groups;

each $R_{14}$, $R_{15}$ and $R_{16}$ is, independently, halogen, $C_{1-6}$ alkyl, $C_{2-8}$ alkenyl, $C_{2-8}$ alkynyl, $C_{3-8}$ cycloalkyl, —$OR_{17}$, CN, $COR_{12}$, $C_{1-6}$ haloalkyl, $C_{1-6}$ perhaloalkyl, $C_{1-6}$ haloalkoxy, $C_{1-6}$ perhaloalkoxy, $C_{1-6}$ perfluoroalkyl, —O—$C_{1-6}$ perfluoroalkyl, $CONR_{12}R_{13}$, —OPO$(OR_{12a})OR_{13a}$, —PO$(OR_{12a})R_{13}$, —OC(O)$OR_{12a}$, —O—$C_{1-6}$ alkyl-$NR_{12}R_{13}$, —OC(O)$NR_{12}R_{13}$, —C(O)$NR_{12}CR_{13a}$, —$COOR_{12a}$, —$SO_3H$, —$NR_{12}R_{13}$, —$N(R_{20})(C_{1-6}$ alkyl)$NR_{12}$, —$N(R_{20})COR_{13}$, —$N(R_{20})COOR_{13a}$, —$SO_2NR_{12}R_{13}$, $NO_2$, —$N(R_{20})SO_2R_{13}$, —$N(R_{20})CONR_{12}R_{13}$, —$N(R_{20})C(=NR_{13})NR_{12}R_{13}$, —$N(R_{20})C(=NR_{13})N(SO_2R_{12})R_{13}$, —$N(R_{20})C(=NR_{13})N(C=OR_{12})R_{13}$, —$SO_2NHCN$, —$SO_2NHCONR_{12}R_{13}$, aryl, phenyl, $CH_2$—$OR_{22}$, —$SR_{22}$, —$CH_2$—$SR_{22}$, —$SO_2NR_{12}R_{13}$, —C(=$NR_{22}$)—, —C(NCN)$R_{22}$—, —$CSN(R_{22})_2$, —C(NH)N($R_{22})_2$, $NO_2$, $NO_3$, azido, hydrazino, hydroxylamino, disulfide, urea, guanidine, or —S(O)$_n$ $R_{12}$ wherein n is 0, 1 or 2;

each $R_{12}$ and $R_{13}$ is, independently, H, OH, $C_{1-8}$ alkyl, $C_{3-8}$ cycloalkyl, aryl, alkoxy, alkenyloxy, alkynyloxy, perfluoroalkoxy, alkoxy-alkyl, or aralkyl;

each $R_{12a}$ and $R_{13a}$ is, independently, H, $C_{1-8}$ alkyl, $C_{2-8}$ alkenyl, $C_{2-8}$ alkynyl, $C_{1-3}$ perfluoroalkyl, $C_{3-8}$ cycloalkyl, aryl, alkoxy-alkyl, or aralkyl;

each $R_{20}$ is, independently, H or $C_{1-6}$ alkyl;

each $R_{17}$ is, independently, H, $C_{1-8}$ alkyl, $C_{2-8}$ alkenyl, $C_{2-8}$ alkynyl, $C_{3-8}$ cycloalkyl, aryl, alkoxy-alkyl, or aralkyl;

$R_{21}$ is H or $C_{1-8}$ alkyl;

each $R_{22}$ is, independently, H or $C_{1-3}$ alkyl;

A is $SO_2$ or —P(O)—$R_{10}$;

X is O, NH, $CH_2$ or S; and

Y is aryl;

with the proviso that A and X are not bonded to adjacent atoms of Y;

or a pharmaceutically acceptable salt or prodrug thereof.

2. A compound of claim 1 or pharmaceutically acceptable salt or prodrug thereof wherein A is $SO_2$.

3. A compound of claim 1 or pharmaceutically acceptable salt or prodrug thereof wherein X is O.

4. A compound of claim 1 or pharmaceutically acceptable salt or prodrug thereof wherein Y is phenyl.

5. A compound of claim 1 or pharmaceutically acceptable salt or prodrug thereof wherein $R_1$ is H or $C_{1-6}$ alkyl.

6. A compound of claim 1 or pharmaceutically acceptable salt or prodrug thereof wherein $R_2$ and $R_3$ are each H.

7. A compound of claim 1 or pharmaceutically acceptable salt or prodrug thereof wherein $R_7$ is H.

8. A compound of claim 1 or pharmaceutically acceptable salt or prodrug thereof wherein $R_2$, $R_3$ and $R_7$ are each H.

9. A compound of claim 1 or pharmaceutically acceptable salt or prodrug thereof wherein $R_1$ is H or $C_{1-6}$ alkyl; $R_2$, $R_3$ and $R_7$ are each H; A is $SO_2$; and X is O.

10. A compound of claim 9 or pharmaceutically acceptable salt or prodrug thereof wherein Y is phenyl.

11. A compound of claim 1, wherein the compound is a compound of the Formula II:

or a pharmaceutically acceptable salt thereof or prodrug thereof.

12. A compound of claim 11 wherein:

$R_5$ is H, $C_{1-6}$ alkyl, $C_{2-8}$ alkenyl, arylalkyl, cycloalkylalkyl, $CO_2R_{11}$, or aryloxyalkyl, wherein said arylalkyl is optionally substituted with up to four substituents independently selected from the group consisting of $C_{1-6}$ alkyl, halogen, $C_{1-8}$ alkoxy, aryl, phenyl, $C_{1-3}$ haloalkyl, $C_{1-3}$ perhaloalkyl, $C_{1-3}$ haloalkoxy, $C_{1-3}$ perhaloalkoxy, CN, alkenyloxy, $CO_2H$ and OH;

$R_6$ is H or $C_{1-6}$ alkyl;

$R_8$ is H, $C_{1-6}$ alkyl, $C_{1-6}$ alkoxy, OH, arylalkoxy, halogen, $CO_2H$ or CN;

$R_9$ is H, halogen or $C_{1-6}$ alkyl;

$R_{10}$ is H or $C_{1-6}$ alkyl; and $R_{11}$ is $C_{1-6}$ alkyl;

or a pharmaceutically acceptable salt thereof or prodrug thereof.

13. A compound of claim 12 or pharmaceutically acceptable salt or prodrug thereof wherein $R_4$ is H.

14. A compound of claim 12 or pharmaceutically acceptable salt or prodrug thereof wherein $R_5$ is H or arylalkyl, wherein said arylalkyl is optionally substituted with up to three $C_{1-3}$ alkoxy groups.

15. A compound of claim 12 or pharmaceutically acceptable salt or prodrug thereof wherein $R_6$ is H or methyl.

16. A compound of claim 12 or pharmaceutically acceptable salt or prodrug thereof wherein $R_8$ is H, halogen, $C_{1-3}$ alkyl, or $C_{1-3}$ alkoxy.

17. A compound of claim 12 or pharmaceutically acceptable salt or prodrug thereof wherein $R_9$ is H.

18. A compound of claim 12 or pharmaceutically acceptable salt or prodrug thereof wherein $R_{10}$ is H.

19. A compound of claim 12 or pharmaceutically acceptable salt or prodrug thereof wherein $R_9$ and $R_{10}$ are each H.

20. A compound of claim 12 or pharmaceutically acceptable salt or prodrug thereof wherein $R_4$, $R_9$ and $R_{10}$ are each H.

21. A compound of claim 12 or pharmaceutically acceptable salt or prodrug thereof wherein $R_4$, $R_9$ and $R_{10}$ are each H; $R_5$ is H or arylalkyl, wherein said arylalkyl is optionally substituted with up to three $C_{1-3}$ alkoxy groups; $R_6$ is H or methyl; and $R_8$ is H, halogen, $C_{1-3}$ alkyl, or $C_{1-3}$ alkoxy.

22. A compound of claim 12 or pharmaceutically acceptable salt or prodrug thereof wherein $R_4$, $R_9$ and $R_{10}$ are each H; $R_5$ is H or benzyl, wherein said benzyl is optionally substituted with up to three methoxy groups; $R_6$ is H or methyl; and $R_8$ is H, halogen, methyl or methoxy.

23. A compound of claim 1 that is selected from compounds 1-29, 31-36, 38-64, 67-82, 85-98, 101-123, 126-160, 163-179, 182-205, and 207-224 below:

1. N-{[4-(but-2-ynyloxy)phenyl]sulfonyl}-D-tryptophan
2. N-{[4-(but-2-ynyloxy)phenyl]sulfonyl}-L-tryptophan
3. N-{[4-(but-2-ynyloxy)phenyl]sulfonyl}-5-fluorotryptophan
4. N-{[4-(but-2-ynyloxy)phenyl]sulfonyl}-5-methoxytryptophan
5. N-{[4-(but-2-ynyloxy)phenyl]sulfonyl}-5-hydroxytryptophan
6. N-{[4-(but-2-ynyloxy)phenyl]sulfonyl}-5-methyltryptophan
7. N-{[4-(but-2-ynyloxy)phenyl]sulfonyl}-6-fluorotryptophan
8. N-{[4-(but-2-ynyloxy)phenyl]sulfonyl}-6-methyltryptophan
9. N-{[4-(but-2-ynyloxy)phenyl]sulfonyl}-alpha-methyltryptophan
10. N-{[4-(but-2-ynyloxy)phenyl]sulfonyl}-7-methyltryptophan
11. N-{[4-(but-2-ynyloxy)phenyl]sulfonyl}-5-hydroxy-L-tryptophan
12. N-{[4-(but-2-ynyloxy)phenyl]sulfonyl}-1-propyl-L-tryptophan
13. 1-butyl-N-{[4-(but-2-ynyloxy)phenyl]sulfonyl}-L-tryptophan
14. N-{[4-(but-2-ynyloxy)phenyl]sulfonyl}-1-isobutyl-L-tryptophan
15. 1-allyl-N-{[4-(but-2-ynyloxy)phenyl]sulfonyl}-L-tryptophan
16. N-{[4-(but-2-ynyloxy)phenyl]sulfonyl}-1-(3-methylbenzyl)-L-tryptophan
17. N-{[4-(but-2-ynyloxy)phenyl]sulfonyl}-1-(4-methylbenzyl)-L-tryptophan
18. N-{[4-(but-2-ynyloxy)phenyl]sulfonyl}-1-(4-chlorobenzyl)-L-tryptophan
19. N-{[4-(but-2-ynyloxy)phenyl]sulfonyl}-1-(4-methoxybenzyl)-L-tryptophan
20. 5-(benzyloxy)-N-{[4-(but-2-ynyloxy)phenyl]sulfonyl}tryptophan
21. N-{[4-(but-2-ynyloxy)phenyl]sulfonyl}-1-methyl-D-tryptophan
22. N-{[4-(but-2-ynyloxy)phenyl]sulfonyl}-1-pentyl-D-tryptophan
23. N-{[4-(but-2-ynyloxy)phenyl]sulfonyl}-1-(cyclohexylmethyl)-D-tryptophan
24. N-{[4-(but-2-ynyloxy)phenyl]sulfonyl}-1-(4-phenoxybutyl)-D-tryptophan
25. 1-benzyl-N-{[4-(but-2-ynyloxy)phenyl]sulfonyl}-D-tryptophan
26. N-{[4-(but-2-ynyloxy)phenyl]sulfonyl}-1-(4-methylbenzyl)-D-tryptophan
27. 1-(1,1'-biphenyl-2-ylmethyl)-N-{[4-(but-2-ynyloxy)phenyl]sulfonyl}-D-tryptophan
28. N-{[4-(but-2-ynyloxy)phenyl]sulfonyl}-1-(4-fluorobenzyl)-D-tryptophan
29. N-{[4-(but-2-ynyloxy)phenyl]sulfonyl}-1-(2-naphthylmethyl)-D-tryptophan
31. N-{[4-(but-2-ynyloxy)phenyl]sulfonyl}-1-(cyclopropylmethyl)-D-tryptophan
32. N-{[4-(but-2-ynyloxy)phenyl]sulfonyl}-1-(cyclobutylmethyl)-D-tryptophan
33. N-{[4-(but-2-ynyloxy)phenyl]sulfonyl}-1-(2-cyclohexylethyl)-D-tryptophan
34. N-{[4-(but-2-ynyloxy)phenyl]sulfonyl}-1-(3-methoxybenzyl)-D-tryptophan
35. N-{[4-(but-2-ynyloxy)phenyl]sulfonyl}-1-(4-methoxybenzyl)-D-tryptophan
36. N-{[4-(but-2-ynyloxy)phenyl]sulfonyl}-1-(3,5-dimethoxybenzyl)-D-tryptophan
38. N-{[4-(but-2-ynyloxy)phenyl]sulfonyl}-1-[4-(trifluoromethoxy)benzyl]-D-tryptophan
39. N-{[4-(but-2-ynyloxy)phenyl]sulfonyl}-1-[2-(trifluoromethyl)benzyl]-D-tryptophan
40. N-{[4-(but-2-ynyloxy)phenyl]sulfonyl}-1-[3-(trifluoromethyl)benzyl]-D-tryptophan
41. N-{[4-(but-2-ynyloxy)phenyl]sulfonyl}-1-[4-(trifluoromethyl)benzyl]-D-tryptophan
42. N-{[4-(but-2-ynyloxy)phenyl]sulfonyl}-1-(4-chlorobenzyl)-D-tryptophan
43. N-{[4-(but-2-ynyloxy)phenyl]sulfonyl}-1-(2-cyanobenzyl)-D-tryptophan
44. N-{[4-(but-2-ynyloxy)phenyl]sulfonyl}-1-(3-cyanobenzyl)-D-tryptophan
45. N-{[4-(but-2-ynyloxy)phenyl]sulfonyl}-1-(4-cyanobenzyl)-D-tryptophan
46. 5-bromo-N-{[4-(but-2-ynyloxy)phenyl]sulfonyl}tryptophan
47. N-{[4-(but-2-ynyloxy)phenyl]sulfonyl}-1-(4-methoxybenzyl)-5-methyltryptophan
48. 1-benzyl-N-{[4-(but-2-ynyloxy)phenyl]sulfonyl}-5-methoxytryptophan
49. N-{[4-(but-2-ynyloxy)phenyl]sulfonyl}-5-methoxy-1-(2-methylbenzyl)tryptophan
50. N-{[4-(but-2-ynyloxy)phenyl]sulfonyl}-5-methoxy-1-(3-methylbenzyl)tryptophan
51. N-{[4-(but-2-ynyloxy)phenyl]sulfonyl}-5-methoxy-1-(2-methoxybenzyl)tryptophan
52. N-{[4-(but-2-ynyloxy)phenyl]sulfonyl}-5-methoxy-1-(3-methoxybenzyl)tryptophan
53. N-{[4-(but-2-ynyloxy)phenyl]sulfonyl}-5-methoxy-1-(4-methoxybenzyl)tryptophan
54. N-{[4-(but-2-ynyloxy)phenyl]sulfonyl}-1-(3,5-dimethoxybenzyl)-5-methoxytryptophan
55. N-{[4-(but-2-ynyloxy)phenyl]sulfonyl}-5-methoxy-1-[2-(trifluoromethyl)benzyl]tryptophan
56. N-{[4-(but-2-ynyloxy)phenyl]sulfonyl}-5-methoxy-1-[3-(trifluoromethyl)benzyl]tryptophan
57. N-{[4-(but-2-ynyloxy)phenyl]sulfonyl}-5-methoxy-1-[4-(trifluoromethyl)benzyl]tryptophan
58. N-{[4-(but-2-ynyloxy)phenyl]sulfonyl}-1-(2-fluorobenzyl)-5-methoxytryptophan
59. N-{[4-(but-2-ynyloxy)phenyl]sulfonyl}-1-(3-fluorobenzyl)-5-methoxytryptophan
60. N-{[4-(but-2-ynyloxy)phenyl]sulfonyl}-1-(4-fluorobenzyl)-5-methoxytryptophan
61. N-{[4-(but-2-ynyloxy)phenyl]sulfonyl}-1-(3,5-difluorobenzyl)-5-methoxytryptophan
62. N-{[4-(but-2-ynyloxy)phenyl]sulfonyl}-1-(4-chlorobenzyl)-5-methoxytryptophan
63. N-{[4-(but-2-ynyloxy)phenyl]sulfonyl}-1-(4-isopropylbenzyl)-5-methoxytryptophan
64. N-{[4-(but-2-ynyloxy)phenyl]sulfonyl}-1-(2-cyanobenzyl)-5-methoxytryptophan
67. N-{[4-(but-2-ynyloxy)phenyl]sulfonyl}-1-isobutyl-5-methoxytryptophan 68. N-{[4-(but-2-ynyloxy)phenyl]sulfonyl}-5-methoxy-1-pentyltryptophan
69. N-{[4-(but-2-ynyloxy)phenyl]sulfonyl}-1-(cyclobutylmethyl)-5-methoxytryptophan
70. N-{[4-(but-2-ynyloxy)phenyl]sulfonyl}-1-(cyclohexylmethyl)-5-methoxytryptophan
71. 1-benzyl-N-{[4-(but-2-ynyloxy)phenyl]sulfonyl}-5-chlorotryptophan
72. N-{[4-(but-2-ynyloxy)phenyl]sulfonyl}-5-chloro-1-(2-methylbenzyl)tryptophan
73. N-{[4-(but-2-ynyloxy)phenyl]sulfonyl}-5-chloro-1-(3-methylbenzyl)tryptophan
74. N-{[4-(but-2-ynyloxy)phenyl]sulfonyl}-5-chloro-1-(2-methoxybenzyl)tryptophan
75. N-{[4-(but-2-ynyloxy)phenyl]sulfonyl}-5-chloro-1-(3-methoxybenzyl)tryptophan
76. N-{[4-(but-2-ynyloxy)phenyl]sulfonyl}-5-chloro-1-(4-methoxybenzyl)tryptophan
77. N-{[4-(but-2-ynyloxy)phenyl]sulfonyl}-5-chloro-1-[4-(trifluoromethyl)benzyl]tryptophan
78. N-{[4-(but-2-ynyloxy)phenyl]sulfonyl}-5-chloro-1-[4-(trifluoromethoxy)benzyl]tryptophan
79. N-{[4-(but-2-ynyloxy)phenyl]sulfonyl}-5-chloro-1-(2-fluorobenzyl)tryptophan
80. N-{[4-(but-2-ynyloxy)phenyl]sulfonyl}-5-chloro-1-(3-fluorobenzyl)tryptophan
81. N-{[4-(but-2-ynyloxy)phenyl]sulfonyl}-5-chloro-1-(4-chlorobenzyl)tryptophan
82. N-{[4-(but-2-ynyloxy)phenyl]sulfonyl}-5-chloro-1-(4-isopropylbenzyl)tryptophan
85. N-{[4-(but-2-ynyloxy)phenyl]sulfonyl}-5-chloro-1-isobutyltryptophan
86. N-{[4-(but-2-ynyloxy)phenyl]sulfonyl}-5-chloro-1-(cyclobutylmethyl)tryptophan
87. N-{[4-(but-2-ynyloxy)phenyl]sulfonyl}-5-chloro-1-(cyclohexylmethyl)tryptophan
88. 1-benzyl-N-{[4-(but-2-ynyloxy)phenyl]sulfonyl}-5-chloro-2-methyltryptophan
89. N-{[4-(but-2-ynyloxy)phenyl]sulfonyl}-5-chloro-1-(2-methoxybenzyl)-2-methyltryptophan
90. N-{[4-(but-2-ynyloxy)phenyl]sulfonyl}-5-chloro-1-(3-methoxybenzyl)-2-methyltryptophan
91. N-{[4-(but-2-ynyloxy)phenyl]sulfonyl}-5-chloro-1-(4-methoxybenzyl)-2-methyltryptophan
92. N-{[4-(but-2-ynyloxy)phenyl]sulfonyl}-5-chloro-2-methyl-1-(4-methylbenzyl)tryptophan
93. N-{[4-(but-2-ynyloxy)phenyl]sulfonyl}-5-chloro-2-methyl-1-[4-(trifluoromethyl)benzyl]tryptophan
94. N-{[4-(but-2-ynyloxy)phenyl]sulfonyl}-5-chloro-2-methyl-1-[4-(trifluoromethoxy)benzyl]tryptophan
95. N-{[4-(but-2-ynyloxy)phenyl]sulfonyl}-5-chloro-1-(4-fluorobenzyl)-2-methyltryptophan
96. N-{[4-(but-2-ynyloxy)phenyl]sulfonyl}-5-chloro-1-(4-chlorobenzyl)-2-methyltryptophan
97. N-{[4-(but-2-ynyloxy)phenyl]sulfonyl}-5-chloro-1-(4-isopropylbenzyl)-2-methyltryptophan
98. N-{[4-(but-2-ynyloxy)phenyl]sulfonyl}-5-chloro-1-(4-cyanobenzyl)-2-methyltryptophan
101. N-{[4-(but-2-ynyloxy)phenyl]sulfonyl}-5-chloro-1-isobutyl-2-methyltryptophan
102. N-{[4-(but-2-ynyloxy)phenyl]sulfonyl}-5-chloro-1-(cyclohexylmethyl)-2-methyltryptophan
103. 1-benzyl-N-{[4-(but-2-ynyloxy)phenyl]sulfonyl}-5-carboxytryptophan
104. N-{[4-(but-2-ynyloxy)phenyl]sulfonyl}-5-carboxy-1-(2-methylbenzyl)tryptophan
105. N-{[4-(but-2-ynyloxy)phenyl]sulfonyl}-5-carboxy-1-(3-methylbenzyl)tryptophan
106. N-{[4-(but-2-ynyloxy)phenyl]sulfonyl}-5-carboxy-1-(4-methylbenzyl)tryptophan
107. N-{[4-(but-2-ynyloxy)phenyl]sulfonyl}-5-carboxy-1-(2-methoxybenzyl)tryptophan
108. N-{[4-(but-2-ynyloxy)phenyl]sulfonyl}-5-carboxy-1-(3-methoxybenzyl)tryptophan
109. N-{[4-(but-2-ynyloxy)phenyl]sulfonyl}-5-carboxy-1-(4-methoxybenzyl)tryptophan
110. N-{[4-(but-2-ynyloxy)phenyl]sulfonyl}-5-carboxy-1-(3,5-dimethoxybenzyl)tryptophan
111. N-{[4-(but-2-ynyloxy)phenyl]sulfonyl}-5-carboxy-1-[2-(trifluoromethyl)benzyl]tryptophan
112. N-{[4-(but-2-ynyloxy)phenyl]sulfonyl}-5-carboxy-1-[3-(trifluoromethyl)benzyl]tryptophan
113. N-{[4-(but-2-ynyloxy)phenyl]sulfonyl}-5-carboxy-1-[4-(trifluoromethyl)benzyl]tryptophan
114. N-{[4-(but-2-ynyloxy)phenyl]sulfonyl}-5-carboxy-1-[4-(trifluoromethoxy)benzyl]tryptophan
115. N-{[4-(but-2-ynyloxy)phenyl]sulfonyl}-5-carboxy-1-(2-fluorobenzyl)tryptophan
116. N-{[4-(but-2-ynyloxy)phenyl]sulfonyl}-5-carboxy-1-(3-fluorobenzyl)tryptophan
117. N-{[4-(but-2-ynyloxy)phenyl]sulfonyl}-5-carboxy-1-(4-fluorobenzyl)tryptophan
118. N-{[4-(but-2-ynyloxy)phenyl]sulfonyl}-5-carboxy-1-(3,5-difluorobenzyl)tryptophan
119. N-{[4-(but-2-ynyloxy)phenyl]sulfonyl}-5-carboxy-1-(4-chlorobenzyl)tryptophan
120. N-{[4-(but-2-ynyloxy)phenyl]sulfonyl}-5-carboxy-1-(4-isopropylbenzyl)tryptophan
121. N-{[4-(but-2-ynyloxy)phenyl]sulfonyl}-5-carboxy-1-(2-cyanobenzyl)tryptophan
122. N-{[4-(but-2-ynyloxy)phenyl]sulfonyl}-5-carboxy-1-(3-cyanobenzyl)tryptophan
123. N-{[4-(but-2-ynyloxy)phenyl]sulfonyl}-5-carboxy-1-(4-cyanobenzyl)tryptophan
126. N-{[4-(but-2-ynyloxy)phenyl]sulfonyl}-5-carboxy-1-(4-carboxybenzyl)tryptophan
127. N-{[4-(but-2-ynyloxy)phenyl]sulfonyl}-5-carboxy-1-methyltryptophan
128. N-{[4-(but-2-ynyloxy)phenyl]sulfonyl}-5-carboxy-1-ethyltryptophan
129. N-{[4-(but-2-ynyloxy)phenyl]sulfonyl}-5-carboxy-1-isobutyltryptophan
130. N-{[4-(but-2-ynyloxy)phenyl]sulfonyl}-5-carboxy-1-pentyltryptophan
131. N-{[4-(but-2-ynyloxy)phenyl]sulfonyl}-5-carboxy-1-(cyclobutylmethyl)tryptophan
132. N-{[4-(but-2-ynyloxy)phenyl]sulfonyl}-5-carboxy-1-(cyclohexylmethyl)tryptophan
133. N-{[4-(but-2-ynyloxy)phenyl]sulfonyl}-5-chlorotryptophan
134. N-{[4-(but-2-ynyloxy)phenyl]sulfonyl}-2-methyltryptophan
135. 1-benzyl-N-{[4-(but-2-ynyloxy)phenyl]sulfonyl}-5-cyanotryptophan
136. N-{[4-(but-2-ynyloxy)phenyl]sulfonyl}-5-cyano-1-(4-methylbenzyl)tryptophan
137. N-{[4-(but-2-ynyloxy)phenyl]sulfonyl}-5-cyano-1-(2-methoxybenzyl)tryptophan
138. N-{[4-(but-2-ynyloxy)phenyl]sulfonyl}-5-cyano-1-(3-methoxybenzyl)tryptophan
139. N-{[4-(but-2-ynyloxy)phenyl]sulfonyl}-5-cyano-1-(4-methoxybenzyl)tryptophan 140. N-{[4-(but-2-ynyloxy)phenyl]sulfonyl}-5-cyano-1-[4-(trifluoromethoxy)benzyl]tryptophan
141. N-{[4-(but-2-ynyloxy)phenyl]sulfonyl}-5-cyano-1-(4-fluorobenzyl)tryptophan
142. N-{[4-(but-2-ynyloxy)phenyl]sulfonyl}-5-cyano-1-(4-isopropylbenzyl)tryptophan
143. N-{[4-(but-2-ynyloxy)phenyl]sulfonyl}-5-cyano-1-isobutyltryptophan
144. 1-benzyl-N-{[4-(but-2-ynyloxy)phenyl]sulfonyl}-2-methyltryptophan
145. N-{[4-(but-2-ynyloxy)phenyl]sulfonyl}-2-methyl-1-(2-methylbenzyl)tryptophan
146. N-{[4-(but-2-ynyloxy)phenyl]sulfonyl}-1-(2-methoxybenzyl)-2-methyltryptophan
147. N-{[4-(but-2-ynyloxy)phenyl]sulfonyl}-1-(3-methoxybenzyl)-2-methyltryptophan
148. N-{[4-(but-2-ynyloxy)phenyl]sulfonyl}-1-(4-methoxybenzyl)-2-methyltryptophan
149. N-{[4-(but-2-ynyloxy)phenyl]sulfonyl}-2-methyl-1-[3-(trifluoromethyl)benzyl]tryptophan
150. N-{[4-(but-2-ynyloxy)phenyl]sulfonyl}-2-methyl-1-[4-(trifluoromethyl)benzyl]tryptophan
151. N-{[4-(but-2-ynyloxy)phenyl]sulfonyl}-2-methyl-1-[4-(trifluoromethoxy)benzyl]tryptophan
152. N-{[4-(but-2-ynyloxy)phenyl]sulfonyl}-1-(2-fluorobenzyl)-2-methyltryptophan
153. N-{[4-(but-2-ynyloxy)phenyl]sulfonyl}-1-(3-fluorobenzyl)-2-methyltryptophan
154. N-{[4-(but-2-ynyloxy)phenyl]sulfonyl}-1-(4-fluorobenzyl)-2-methyltryptophan
155. N-{[4-(but-2-ynyloxy)phenyl]sulfonyl}-1-(3,5-difluorobenzyl)-2-methyltryptophan
156. N-{[4-(but-2-ynyloxy)phenyl]sulfonyl}-1-(4-chlorobenzyl)-2-methyltryptophan
157. N-{[4-(but-2-ynyloxy)phenyl]sulfonyl}-1-(4-isopropylbenzyl)-2-methyltryptophan
158. N-{[4-(but-2-ynyloxy)phenyl]sulfonyl}-1-(2-cyanobenzyl)-2-methyltryptophan
159. N-{[4-(but-2-ynyloxy)phenyl]sulfonyl}-1-(3-cyanobenzyl)-2-methyltryptophan
160. N-{[4-(but-2-ynyloxy)phenyl]sulfonyl}-1-(4-cyanobenzyl)-2-methyltryptophan
163. N-{[4-(but-2-ynyloxy)phenyl]sulfonyl}-1-ethyl-2-methyltryptophan
164. N-{[4-(but-2-ynyloxy)phenyl]sulfonyl}-1-isobutyl-2-methyltryptophan
165. N-{[4-(but-2-ynyloxy)phenyl]sulfonyl}-1-(cyclobutylmethyl)-2-methyltryptophan
166. N-{[4-(but-2-ynyloxy)phenyl]sulfonyl}-1-(cyclohexylmethyl)-2-methyltryptophan
167. 1-benzyl-N-{[4-(but-2-ynyloxy)phenyl]sulfonyl}-5-methyltryptophan
168. N-{[4-(but-2-ynyloxy)phenyl]sulfonyl}-5-methyl-1-(2-methylbenzyl)tryptophan
169. N-{[4-(but-2-ynyloxy)phenyl]sulfonyl}-5-methyl-1-(3-methylbenzyl)tryptophan
170. N-{[4-(but-2-ynyloxy)phenyl]sulfonyl}-1-(2-methoxybenzyl)-5-methyltryptophan
171. N-{[4-(but-2-ynyloxy)phenyl]sulfonyl}-1-(3-methoxybenzyl)-5-methyltryptophan
172. N-{[4-(but-2-ynyloxy)phenyl]sulfonyl}-5-methyl-1-[2-(trifluoromethyl)benzyl]tryptophan
173. N-{[4-(but-2-ynyloxy)phenyl]sulfonyl}-5-methyl-1-[3-(trifluoromethyl)benzyl]tryptophan
174. N-{[4-(but-2-ynyloxy)phenyl]sulfonyl}-5-methyl-1-[4-(trifluoromethyl)benzyl]tryptophan
175. N-{[4-(but-2-ynyloxy)phenyl]sulfonyl}-1-(3-fluorobenzyl)-5-methyltryptophan
176. N-{[4-(but-2-ynyloxy)phenyl]sulfonyl}-1-(4-fluorobenzyl)-5-methyltryptophan
177. N-{[4-(but-2-ynyloxy)phenyl]sulfonyl}-1-(3,5-difluorobenzyl)-5-methyltryptophan
178. N-{[4-(but-2-ynyloxy)phenyl]sulfonyl}-1-(4-chlorobenzyl)-5-methyltryptophan
179. N-{[4-(but-2-ynyloxy)phenyl]sulfonyl}-1-(4-isopropylbenzyl)-5-methyltryptophan
182. N-{[4-(but-2-ynyloxy)phenyl]sulfonyl}-1-ethyl-5-methyltryptophan
183. N-{[4-(but-2-ynyloxy)phenyl]sulfonyl}-1-isobutyl-5-methyltryptophan
184. N-{[4-(but-2-ynyloxy)phenyl]sulfonyl}-5-methyl-1-pentyltryptophan
185. 1-benzyl-N-{[4-(but-2-ynyloxy)phenyl]sulfonyl}-5-methoxy-2-methyltryptophan
186. N-{[4-(but-2-ynyloxy)phenyl]sulfonyl}-5-methoxy-2-methyl-1-(2-methylbenzyl)tryptophan
187. N-{[4-(but-2-ynyloxy)phenyl]sulfonyl}-5-methoxy-2-methyl-1-(3-methylbenzyl)tryptophan
188. N-{[4-(but-2-ynyloxy)phenyl]sulfonyl}-5-methoxy-2-methyl-1-(4-methylbenzyl)tryptophan
189. N-{[4-(but-2-ynyloxy)phenyl]sulfonyl}-5-methoxy-1-(2-methoxybenzyl)-2-methyltryptophan
190. N-{[4-(but-2-ynyloxy)phenyl]sulfonyl}-5-methoxy-1-(3-methoxybenzyl)-2-methyltryptophan
191. N-{[4-(but-2-ynyloxy)phenyl]sulfonyl}-5-methoxy-1-(4-methoxybenzyl)-2-methyltryptophan
192. N-{[4-(but-2-ynyloxy)phenyl]sulfonyl}-1-(3,5-dimethoxybenzyl)-5-methoxy-2-methyltryptophan
193. N-{[4-(but-2-ynyloxy)phenyl]sulfonyl}-5-methoxy-2-methyl-1-[2-(trifluoromethyl)benzyl]tryptophan
194. N-{[4-(but-2-ynyloxy)phenyl]sulfonyl}-5-methoxy-2-methyl-1-[3-(trifluoromethoxy)benzyl]tryptophan
195. N-{[4-(but-2-ynyloxy)phenyl]sulfonyl}-5-methoxy-2-methyl-1-[4-(trifluoromethyl)benzyl]tryptophan
196. N-{[4-(but-2-ynyloxy)phenyl]sulfonyl}-5-methoxy-2-methyl-1-[4-(trifluoromethoxy)benzyl]tryptophan
197. N-{[4-(but-2-ynyloxy)phenyl]sulfonyl}-1-(2-fluorobenzyl)-5-methoxy-2-methyltryptophan
198. N-{[4-(but-2-ynyloxy)phenyl]sulfonyl}-1-(3-fluorobenzyl)-5-methoxy-2-methyltryptophan
199. N-{[4-(but-2-ynyloxy)phenyl]sulfonyl}-1-(4-fluorobenzyl)-5-methoxy-2-methyltryptophan
200. N-{[4-(but-2-ynyloxy)phenyl]sulfonyl}-1-(3,5-difluorobenzyl)-5-methoxy-2-methyltryptophan
201. N-{[4-(but-2-ynyloxy)phenyl]sulfonyl}-1-(4-chlorobenzyl)-5-methoxy-2-methyltryptophan
202. N-{[4-(but-2-ynyloxy)phenyl]sulfonyl}-1-(4-isopropylbenzyl)-5-methoxy-2-methyltryptophan
203. N-{[4-(but-2-ynyloxy)phenyl]sulfonyl}-1-(2-cyanobenzyl)-5-methoxy-2-methyltryptophan
204. N-{[4-(but-2-ynyloxy)phenyl]sulfonyl}-1-(3-cyanobenzyl)-5-methoxy-2-methyltryptophan
205. N-{[4-(but-2-ynyloxy)phenyl]sulfonyl}-1-(4-cyanobenzyl)-5-methoxy-2-methyltryptophan
207. N-{[4-(but-2-ynyloxy)phenyl]sulfonyl}-1-(4-carboxybenzyl)-5-methoxy-2-methyltryptophan
208. N-{[4-(but-2-ynyloxy)phenyl]sulfonyl}-5-methoxy-1,2-dimethyltryptophan
209. N-{[4-(but-2-ynyloxy)phenyl]sulfonyl}-1-ethyl-5-methoxy-2-methyltryptophan
210. N-{[4-(but-2-ynyloxy)phenyl]sulfonyl}-1-isobutyl-5-methoxy-2-methyltryptophan 211. N-{[4-(but-2-ynyloxy)phenyl]sulfonyl}-5-methoxy-2-methyl-1-pentyltryptophan
212. N-{[4-(but-2-ynyloxy)phenyl]sulfonyl}-1-(cyclobutylmethyl)-5-methoxy-2-methyltryptophan
213. N-{[4-(but-2-ynyloxy)phenyl]sulfonyl}-1-(cyclohexylmethyl)-5-methoxy-2-methyltryptophan
214. N-{[4-(but-2-ynyloxy)phenyl]sulfonyl}-1-(4-hydroxybenzyl)-D-tryptophan
215. N-{[4-(but-2-ynyloxy)phenyl]sulfonyl}-1-(4-ethoxybenzyl)-D-tryptophan
216. 1-[4-(allyloxy)benzyl]-N-{[4-(but-2-ynyloxy)phenyl]sulfonyl}-D-tryptophan
217. N-{[4-(but-2-ynyloxy)phenyl]sulfonyl}-5-methyl-D (or L)-tryptophan
218. N-{[4-(but-2-ynyloxy)phenyl]sulfonyl}-5-methyl-L (or D)-tryptophan
219. 1-(tert-butoxycarbonyl)-N-{[4-(but-2-ynyloxy)phenyl]sulfonyl}-L-tryptophan
220. 1-(tert-butoxycarbonyl)-N-{[4-(but-2-ynyloxy)phenyl]sulfonyl}-D-tryptophan
221. N-{[4-(but-2-ynyloxy)phenyl]sulfonyl}-5-methoxy-D(or L)-tryptophan
222. N-{[4-(but-2-ynyloxy)phenyl]sulfonyl}-methoxy-L (or D)-tryptophan
223. 5-(benzyloxy)-N-{[4-(but-2-ynyloxy)phenyl]sulfon}-D(or L)-tryptophan
224. 5-(benzyloxy)-N-{[4-(but-2-ynyloxy)phenyl]sulfon}-L(or D)-tryptophan;

or a pharmaceutically acceptable salt thereof, or prodrug thereof.

24. A compound of claim 1 that is selected from:
N-{[4-(but-2-ynyloxy)phenyl]sulfonyl}-1-(4-methoxybenzyl)-D-tryptophan;
N-{[4-(but-2-ynyloxy)phenyl]sulfonyl}-5-methyl(or D)-L-tryptophan;
N-{[4-(but-2-ynyloxy)phenyl]sulfonyl}-5-methoxy-D(or L)-tryptophan;
N-{[4-(but-2-ynyloxy)phenyl]sulfonyl}-5-chloro-1-(4-methoxybenzyl)-2-methyltryptophan; or
1-benzyl-N-{[4-(but-2-ynyloxy)phenyl]sulfonyl}-5-methoxy-2-methyltryptophan;

or a pharmaceutically acceptable salt thereof or prodrug thereof.

25. A method of treating a disease or disorder in a mammal comprising providing to the mammal in need thereof an effective amount of a compound of claim 1, wherein the disease or disorder is rheumatoid arthritis, juvenile rheumatoid arthritis, ulcerative colitis, or Crohn's disease.

* * * * *

UNITED STATES PATENT AND TRADEMARK OFFICE
CERTIFICATE OF CORRECTION

PATENT NO.       : 7,576,222 B2  
APPLICATION NO.  : 11/318701  
DATED            : August 18, 2009  
INVENTOR(S)      : Park et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 405 days.

Signed and Sealed this

Seventh Day of September, 2010

David J. Kappos
*Director of the United States Patent and Trademark Office*